(12) United States Patent
Lin et al.

(10) Patent No.: US 8,404,738 B2
(45) Date of Patent: Mar. 26, 2013

(54) 4-AMINO-N-HYDROXY-BENZAMIDES FOR THE TREATMENT OF CANCER

(75) Inventors: Xianfeng Lin, Shanghai (CN); Zongxing Qiu, Shanghai (CN); Guozhi Tang, Shanghai (CN); Jason Christopher Wong, Shanghai (CN); Zhenshan Zhang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/351,283

(22) Filed: Jan. 17, 2012

(65) Prior Publication Data
US 2012/0190700 A1 Jul. 26, 2012

(30) Foreign Application Priority Data
Jan. 21, 2011 (WO) ................ PCT/CN2011/070464

(51) Int. Cl.
*A61K 31/4015* (2006.01)
*A61P 35/00* (2006.01)
*C07D 207/273* (2006.01)
*C07D 207/48* (2006.01)
*C07D 207/14* (2006.01)

(52) U.S. Cl. ........ 514/423; 514/426; 514/428; 514/429; 514/617; 562/622; 564/168; 548/543; 548/557

(58) Field of Classification Search .................. None
See application file for complete search history.

(56) References Cited

FOREIGN PATENT DOCUMENTS

| WO | WO 03/076430 | * | 9/2003 |
|----|--------------|---|--------|
| WO | 2005/108367 | | 11/2005 |
| WO | 2006/016680 | | 2/2006 |
| WO | 2008/055068 | | 5/2008 |
| WO | 2009/129335 | | 10/2009 |

OTHER PUBLICATIONS (International Search Report PCT/EP2012/050665 Jul. 3, 2012).

* cited by examiner

*Primary Examiner* — Sreeni Padmanabhan
*Assistant Examiner* — Irina Neagu
(74) *Attorney, Agent, or Firm* — George W. Johnston; Patricia S. Rocha-Tramaloni

(57) ABSTRACT

The present invention provides compounds of formula

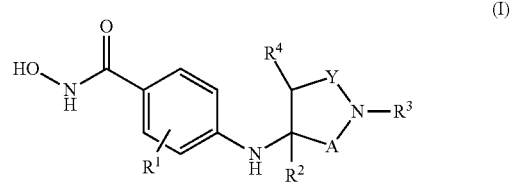

(I)

or pharmaceutically acceptable salts, esters or stereoisomers thereof, wherein $R^1$ to $R^4$, A and Y have the meanings given herein, as well as methods for making those compounds and their use as medicament, in particular as medicament for the treatment of cancer.

21 Claims, No Drawings

4-AMINO-N-HYDROXY-BENZAMIDES FOR THE TREATMENT OF CANCER

PRIORITY TO RELATED APPLICATION(S)

This application claims the benefit of International Patent Application No. PCT/CN2011/070464, filed Jan. 21, 2011, which is hereby incorporated by reference in its entirety.

BACKGROUND OF THE INVENTION

Histone deacetylases (HDACs) are one of the major classes of post-translational regulators and have been implicated in pro-growth, anti-apoptotic, and anti-differentiation roles in various cancer types. As the key enzymatic components of multiprotein complexes, histone deacetylases (HDACs) are responsible for deacetylation of lysine residues in histone and nonhistone protein substrates. Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., *Blood* 2000, 96, 1490-1495).

HDAC proteins comprise a family of 18 members in humans with homologies to yeast HDACs, Rpd3, Hda1, and Sir2. Based on their sequence similarity, cellular localization tendencies, tissue expression patterns, and enzymatic mechanisms, the HDACs can thus be divided into four classes. The class I HDACs (HDACs 1, 2, 3, and 8), homologous to Rpd3, localize primarily in the nucleus and appear to be ubiquitously expressed in most tissues. The class II HDACs (HDACs 4, 5, 6, 7, 9, 10), homologous to Hda1, are able to shuttle between the nucleus and the cytoplasm depending on a variety of regulatory signals and cellular state, and are expressed in a more limited number of cell types. These HDACs can be further subdivided into class IIa (HDACs 4, 5, 7, 9), and class IIb (HDACs 6, 10). HDAC11 is the sole member of class IV histone deacetylase. Class I, II, and IV HDACs are all zinc-dependent deacetylases. In contrast, the class III HDACs, homologous to Sir2, are NAD+-dependent deacetylases that are mechanistically distinct from the class I and II HDACs and are not inhibited by classical HDAC inhibitors such as trichostatin A, trapoxin B, or MS-275.

Given their association with cancer formation, class I and II HDAC proteins have emerged as attractive targets for anti-cancer therapy. The class I HDACs in particular have been closely associated with anti-proliferative effects against tumor cells. For example, pharmacological inhibition of HDACs 1-3 leads to induction of the cyclin-dependent kinase inhibitor p21 and concomitant cell cycle arrest. Several HDAC inhibitor (HDACi) drugs are in various stages of clinical trials, with SAHA (suberoylanilide hydroxamic acid, Vorinostat) and Romidepsin (FK228) gaining FDA approval in 2006 and 2009 respectively, for the treatment of cutaneous T-cell lymphoma (CTCL). Recently, the expression of HDAC8 (and not any other HDAC isoforms) was shown to significantly and independently correlate with the disease stage and poor survival of neuroblastoma (NB), which is a neoplasm of the peripheral autonomic nervous system that represents the second most common malignancy of childhood. Furthermore, knockdown of HDAC8 by siRNA led to NB cell differentiation and inhibited cell growth while its overexpression blocked retinoic acid-induced NB differentiation (*Clinical Cancer Research* 2009, 15, 91-99). HDAC8 is therefore a potential drug target for the differentiation therapy of minimal residual disease in NB. In addition, a possible correlation between HDAC8 and acute myeloid leukemia (AML) has also been suggested (*Bioorg. Med. Chem. Lett.* 2007, 17, 2874).

Unlike class I HDACs which are predominantly nuclear enzymes, class IIa enzymes shuttle between the nucleus and cytoplasm, and are known to associate with the HDAC3/SMRT/N-CoR complex and MEF2 and as such have important roles in regulating muscle cell gene expression (reviewed in *Oncogene* 2007, 26, 5450-5467) and the immune response (*Biochemical Pharmacology* 2007, 74, 465-476). The IIb subclass enzymes uniquely feature two deacetylase domains, and are primarily cytoplasmic. Significantly, HDAC6 operates on a variety of substrates other than histone proteins, and is involved in processing Lys40 of the mitotic spindle protein α-tubulin. HDAC6 also has a dynein motor binding domain to enable HDAC6 to shuttle cargo along the microtubule, and a zinc finger ubiquitin-binding domain at the C-terminus. Through its ubiquitin-binding activity, HDAC6 is able to mediate the recruitment of autophagic material to aggresomes for degradation, thus decreasing the cytotoxic effects of these aggregates (*Cell* 2003, 115, 727-738). Inhibition of HDAC6 activity by the specific inhibitor, tubacin, can increase accumulation of acetylated α-tubulin and inhibit cell motility without affecting microtubule stability per se (*J. Am. Chem. Soc.* 2003, 125, 5586-5587, *Proc. Nat. Acad. Sci. USA* 2003, 4389-4394).

Multiple myeloma (MM) is a plasma cell malignancy characterized by complex heterogeneous cytogenetic abnormalities and infiltration of malignant cells into the bone marrow, leading to bone disease, hypercalcemia, cytopenia, renal dysfunction, hyperviscosity and peripheral neuropathy. Standard proteasome inhibitor-based therapies have achieved remarkable response rates in MM, however combination therapies with new targeted drugs are still needed due to the development of drug resistance and poor long-term survival. It was recently demonstrated that concomitant proteasome and HDAC6 inhibition can lead to synergistic anti-proliferative effects in MM cells, most likely due to the role of HDAC6 in mediating aggresome function and the ensuing misfolded protein stress that develops as a result of dual proteasome/aggresome inhibition (*Proc. Nat. Acad. Sci. USA* 2005, 102, 8567-8572). HDAC6 is therefore an attractive novel target for the development of new MM combination therapies.

The compounds according to this invention are inhibitors of HDAC6 or HDAC8 and therefore show anti-proliferative and differentiation-inducing activities, which result in inhibition of tumor cell proliferation and induction of apoptosis. Pan HDAC inhibitors have broad spectrum preclinical activity against a wide range of cancer types, yet also possess non-specific cytotoxicity which may limit their clinical application. In contrast, HDAC inhibitors targeted toward specific isoforms, especially HDAC6 and HDAC8, typically show lower non-specific cytotoxicity and can be suitable for the treatment of certain cancer subtypes. The compounds of the present invention show enhanced selectivity toward HDAC6 or HDAC8 compared with the pan HDAC inhibitor SAHA, as assessed by both enzymatic and in-cell assays.

Based on different zinc binding groups, four major classes of HDAC inhibitors have been extensively described in the literature: (1) hydroxamic acids; (2) ortho-aminoanilides; (3) thiols or their prodrugs; (4) carboxylic acids and their analogues (reviewed in *J. Med. Chem.* 2003, 46, 5097-5116). In general, the hydroxamic acids such as SAHA, LBH589, PXD101, JNJ26481585 and ITF2357 display broad inhibitory activity against most HDAC isoforms in the submicromolar range (*J. Med. Chem.* 2007, 50, 4405). On the other hand, the ortho-aminoanilides exemplified by MS275 and its aryl substituted analog show high potency and class I activity confined primarily to the HDAC 1, 2, 3 subtypes. The thiol prodrug FK228 (depsipeptide/Romidepsin) also has been reported to have similar class I selectivity, although the drug's developer, Gloucester pharmaceuticals, has claimed that the molecule is a pan-HDAC inhibitor (Mitchell Keegan, *Discovery On Target HDAC Inhibitor Conference* 2007). In contrast, the fatty acid class are the least potent of the HDAC inhibitors, with enzyme inhibitory values in the high micromolar ranges.

Limited reports confined to the realm of hydroxamic acid-based molecules have been published describing compounds with HDAC6 and/or HDAC8 selectivity. Tubacin is the prototype HDAC6 selective inhibitor with a bulky capping group contacting the rim region of HDAC6. Kozikowski et al. have described potent HDAC6-selective triazolylphenyl capped hydroxamates and related phenylisoxazole capped hydroxamate inhibitors with greater than 50 fold selectivity over HDAC1 and HDAC3 (*J. Med. Chem.* 2008, 51, 3437 and *J. Med. Chem.* 2008, 51, 4370). In all instances, the inhibitors have rigid and bulky capping groups as selectivity elements and those capping groups are linked with zinc binding hydroxamic acids through flexible aliphatic chains. In a different approach, Envivo Pharmaceuticals disclosed 1,2,3,4-tetrahydroisoquinoline hydroxamates for potential treatment of neurodegenerative diseases (WO2005/108367), but their HDAC isoform selectivity has yet to be clarified. Most recently, Smil et. al. from MethylGene Inc. reported chiral 3,4-dihydroquinoxalin-2(1H)-one and piperazine-2,5-dione aryl hydroxamates with selectivity (up to 40-fold) for human HDAC6 over other class I/IIa HDACs.

SUMMARY OF THE INVENTION

The invention relates to novel anti-tumor agents and pharmaceutically acceptable salts thereof, and processes for the manufacture of these novel compounds and medicaments containing them. The compounds of the invention have anti-proliferative and differentiation-inducing activity, which results in inhibition of tumor cell proliferation and induction of apoptosis. The invention also relates to the use of such compounds for the treatment of diseases such as cancer and for the manufacture of corresponding medicaments.

DETAILED DESCRIPTION OF THE INVENTION

The invention relates in particular to (i) a compound of formula (I)

wherein
$R^1$ is hydrogen, alkyl or halogen;
$R^2$ is hydrogen, alkyl, hydroxyalkyl, alkoxyalkyl, aminoalkyl, alkylaminoalkyl or dialkylaminoalkyl;
$R^3$ is phenyl, unsubstituted or substituted once, or twice or three times by halogen, alkyl, alkoxy, alkylsulfonyl, cyano, trifluoromethyl, phenyl, phenoxy, pyrrolyl, imidazolyl, oxazolyl or dialkylaminoalkoxy;

naphthalenyl, unsubstituted or once or twice substituted by halogen, alkyl, alkoxy, alkylsulfonyl, cyano, trifluoromethyl, dialkylamino or dialkylaminoalkyl;
quinolinyl, unsubstituted or once or twice substituted by alkyl, alkoxy, alkylsulfonyl, cyano, trifluoromethyl, dialkylamino or dialkylaminoalkyl;
cycloalkyl;
phenylalkyl, wherein phenyl can be unsubstituted or once or twice substituted by halogen, alkoxy, phenyl, alkyl, cyano, alkylsulfonyl, trifluoromethyl, phenoxy, pyrrolyl, imidazolyl, oxazolyl or dialkylaminoalkoxy;
naphthalenylalkyl, wherein naphthalenyl can be unsubstituted or once or twice substituted by halogen, alkoxy, phenyl, alkyl, cyano, alkylsulfonyl, trifluoromethyl, phenoxy, pyrrolyl, imidazolyl, oxazolyl or dialkylaminoalkoxy;
phenylcycloalkyl, wherein phenyl can be unsubstituted or once or twice substituted by halogen, alkoxy, phenyl, alkyl, cyano, alkylsulfonyl, trifluoromethyl, phenoxy, pyrrolyl, imidazolyl, oxazolyl or dialkylaminoalkoxy;
pyrimidinyl, wherein pyrimidinyl can be unsubstituted or once or twice substituted by alkoxy, phenyl, alkyl, cyano, alkylsulfonyl, trifluoromethyl, phenoxy, pyrrolyl, imidazolyl, oxazolyl or dialkylaminoalkoxy;
phenylsulfonyl, wherein phenyl can be unsubstituted or once or twice substituted by halogen, phenyl, alkoxy, alkyl, cyano, alkylsulfonyl, trifluoromethyl, phenoxy, pyrrolyl, imidazolyl, oxazolyl or dialkylaminoalkoxy; or
phenylcarbonyl, wherein phenyl can be unsubstituted or once or twice substituted by halogen, alkoxy, phenyl, alkyl, cyano, alkylsulfonyl, trifluoromethyl, phenoxy, pyrrolyl, imidazolyl, oxazolyl or dialkylaminoalkoxy;
$R^4$ is hydrogen or alkyl;
Y is —$CH_2$— or —C=O;
or
$R^4$ and Y, together with the carbon atom to which $R^4$ is attached, may form a phenyl ring or pyridinyl ring, which may be unsubstituted or further substituted by halogen; provided that $R^2$ is alkyl.
A is —C=O, —$CH_2$— or —CH-alkyl, provided that A and Y are not —C=O at the same time;
or a pharmaceutically acceptable salt, ester or stereoisomers thereof.

The invention also relates to a process for the manufacture of these novel compounds and medicaments containing them.

The compounds of the present invention employ rigid tetrahydronaphthylene, 1,2,3,4-tetrahydroquinoline and chroman as linker between the zinc-binding hydroxamic acid group and rim-binding capping groups. They demonstrate submicromolar to micromolar inhibition of HDAC6 or HDAC8 based on their in-cell tubulin acetylation induction activity (HDAC6 in-cell assay) and enzymatic inhibition of HDAC8. Compounds from the present invention are able to induce obvious NB cell differentiation. Compounds from the present invention also demonstrate synergy when combined with bortezomib in cell growth inhibition of MM cell lines. As a surrogate for in-cell HDAC1/2/3 inhibition, p21 induction was used as a counterscreen to evaluate the selectivity of the compounds in the present invention toward HDAC6 or HDAC8 over HDACs 1, 2, and 3. In contrast to positive controls MS275 and SAHA, none of the compounds of the present invention showed significant or comparable p21 induction activity at 3 μM, 10 μM, and 30 μM concentrations. The compounds of the present invention are potent and selective HDAC6 or HDAC8 inhibitors that could be particularly suitable for the treatment of multiple myeloma and neuroblastoma, based upon the emerging biology of HDAC6 and HDAC8 in these two cancer types.

It has been found that the compounds of the present invention are HDAC6 or HDAC8 inhibitors which have anti-proliferative and differentiation-inducing activity, resulting in inhibition of tumor cell proliferation and induction of apoptosis. These compounds are therefore useful for the treatment of diseases such as neuroblastoma and multiple myeloma in humans or animals.

As used herein, the term "alkyl", alone or in combination, signifies a saturated, linear- or branched, mono- or bivalent hydrocarbon containing 1 to 8, preferably 1 to 6, more preferably 1 to 4 carbon atoms, for example methyl, ethyl, propyl, isopropyl, 1-butyl, 2-butyl and tert-butyl. Preferred "alkyl" groups are methyl, ethyl, propyl and butyl, more preferably methyl, ethyl, isopropyl and tert-butyl.

The term "alkoxy", alone or in combination, signifies a group alkyl-O—, wherein the "alkyl" is as defined above; for example methoxy, ethoxy, propoxy, isopropoxy, n-butoxy, i-butoxy, 2-butoxy and t-butoxy. Preferred "alkoxy" groups are methoxy and ethoxy and more preferably methoxy.

The term "cycloalkyl", alone or in combination, refers to a saturated, mono- or bivalent cyclic hydrocarbon containing from 3 to 7 carbon atoms, preferably from 3 to 6 carbon atoms, for example, cyclopropyl, cyclobutyl, cyclopentyl, cyclohexyl and cycloheptyl. Preferred "cycloalkyl" groups are cyclopropyl, cyclopentyl and cyclohexyl.

The term "halogen" means fluorine, chlorine, bromine or iodine. "Halogen" is preferably fluorine, chlorine or bromine.

The term "carbonyl", alone or in combination, refers to the group —C(O)—.

The term "amino", alone or in combination, refers to primary (—NH$_2$), secondary (—NH—) or tertiary amino (—N—).

The term "hydroxy", alone or in combination, refers to the group —OH.

The term "sulfonyl", alone or in combination, refers to the group —S(O)$_2$—.

The terms "phenylalkyl", "naphthalenylalkyl", "phenylcycloalkyl", "phenylsulfonyl" or "phenylcarbonyl" mean that the aromatic groups, i.e. phenyl or naphthalenyl, are attached via an alkyl, cycloalkyl, sulfonyl or carbonyl group as a bridging group, wherein the terms "alkyl" and "cycloalkyl" have the meanings given above.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as acetate esters, propionate esters, benzoate esters and pivalate esters. Additionally, any physiologically acceptable equivalents of the compounds of general formula (I), similar to the metabolically labile esters, which are capable of producing the parent compounds of general formula (I) in vivo, are within the scope of this invention. Preferred are the acetyl, propionyl, and benzoyl esters of the compounds of formula (I).

Compounds of the general formula (I) which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Another embodiment of present invention is (ii) a compound of formula (I) or a pharmaceutically acceptable salt, ester or stereoisomers thereof, wherein
$R^1$ is hydrogen or halogen;
$R^2$ is hydrogen or alkyl;
$R^3$ is phenyl, unsubstituted or substituted once, or twice or three times by halogen, alkyl, alkoxy, alkylsulfonyl, cyano, trifluoromethyl, phenyl, phenoxy, pyrrolyl, imidazonyl, oxazolyl or dialkylaminoalkoxy;
naphthalenyl;
quinolinyl;
cycloalkyl;
phenylalkyl, wherein phenyl can be unsubstituted or once or twice substituted by halogen, alkoxy or phenyl;
naphthalenylalkyl;
phenylcycloalkyl;
pyrimidinyl;
phenylsulfonyl, wherein phenyl can be unsubstituted or once or twice substituted by halogen or phenyl; or phenylcarbonyl, wherein phenyl can be unsubstituted or once or twice substituted by halogen or alkoxy;
$R^4$ is hydrogen or alkyl; and all remaining substituents have the significances given before.

Another particular embodiment of the invention is (iii) a compound of formula (I) or a pharmaceutically acceptable salt, ester or stereoisomers thereof, wherein R1 is hydrogen, fluoro or chloro; and all remaining substituents have the significances given before.

Another particular embodiment of the invention is (iv) a compound of formula (I) or a pharmaceutically acceptable salt, ester or stereoisomers thereof, wherein $R^2$ is hydrogen, methyl or ethyl; and all remaining substituents have the significances given before.

Further particular embodiment of the invention is (v) a compound of formula (I) or a pharmaceutically acceptable salt, ester or stereoisomers thereof, wherein $R^2$ is hydrogen or methyl; and all remaining substituents have the significances given before.

Another particular embodiment of the invention is (vi) a compound of formula (I) or a pharmaceutically acceptable salt, ester or stereoisomers thereof, wherein $R^3$ is phenyl, unsubstituted or substituted once, or twice or three times by fluoro, chloro, methoxy, methyl, isopropyl, isopropoxy, butyl, tert-butyl, methylsulfonyl, cyano, trifluoromethyl, phenoxy, phenyl, pyrrolyl, imidazonyl, oxazolyl or dimethylaminoethoxy; naphthalenyl; quinolinyl; cyclohexyl; phenylmethyl; phenylethyl; phenylisopropyl; chlorophenylmethyl; methoxyphenylmethyl; chlorophenylisopropyl; phenylphenylisopropyl; naphthalenylisopropyl; phenylcyclobutyl; phenylcyclopentanyl; phenylcyclohexyl; pyrimidinyl; phenylsulfonyl; fluorophenylsulfonyl, chlorophenylsulfonyl, phenylphenylsulfonyl, phenylcarbonyl; fluorophenylcarbonyl or methoxyphenylcarbonyl; and all remaining substituents have the significances given before.

Further particular embodiment of the invention is (vii) a compound of formula (I) or a pharmaceutically acceptable salt, ester or stereoisomers thereof, wherein $R^3$ is phenyl, unsubstituted or once substituted by dimethylaminoethoxy, once or twice substituted by fluoro, chloro or cyano; quinolinyl; phenylmethyl; phenylethyl; phenylisopropyl; chlorophenylisopropyl; phenylcyclobutyl; phenylcyclohexyl; pyrimidinyl; fluorophenylsulfonyl; fluorophenylcarbonyl or chlorophenylmethyl; and all remaining substituents have the significances given before.

Another particular embodiment of the invention is (viii) a compound of formula (I) or a pharmaceutically acceptable salt, ester or stereoisomers thereof, wherein $R^4$ is hydrogen or methyl; and all remaining substituents have the significances given before.

Further embodiment of the invention is (ix) a compound of formula (I) or a pharmaceutically acceptable salt, ester or stereoisomers thereof, wherein Y is —CH$_2$— or —C=O; and all remaining substituents have the significances given before.

Further particular embodiment of the invention is (x) a compound of formula (I) or a pharmaceutically acceptable salt, ester or stereoisomers thereof, wherein $R^4$ and Y, together with the carbon atom to which $R^4$ is attached, form a phenyl ring or pyridinyl ring, which may be unsubstituted or substituted by fluoro provided that $R^2$ is alkyl; and all remaining substituents have the significances given before.

Another particular embodiment of the invention is (xi) a compound of formula (I) or a pharmaceutically acceptable salt, ester or stereoisomers thereof, wherein A is —C=O, —CH$_2$— or —CH—CH$_3$; provided that A and Y are not —C=O at the same time; and all remaining substituents have the significances given before.

Particular compounds of formula (I) or a pharmaceutically acceptable salt, ester or stereoisomers thereof, according to the invention can be selected from N-Hydroxy-4-(5-oxo-1-phenyl-pyrrolidin-3-ylamino)-benzamide;
4-[1-(2-Fluoro-phenyl)-2-oxo-pyrrolidin-3-ylamino]-N-hydroxy-benzamide;
4-[1-(3-Fluoro-phenyl)-2-oxo-pyrrolidin-3-ylamino]-N-hydroxy-benzamide;
4-[1-(4-Fluoro-phenyl)-2-oxo-pyrrolidin-3-ylamino]-N-hydroxy-benzamide;
4-[1-(2-Chloro-phenyl)-2-oxo-pyrrolidin-3-ylamino]-N-hydroxy-benzamide;
4-[1-(3-Chloro-phenyl)-2-oxo-pyrrolidin-3-ylamino]-N-hydroxy-benzamide;
4-[1-(4-Chloro-phenyl)-2-oxo-pyrrolidin-3-ylamino]-N-hydroxy-benzamide;
N-Hydroxy-4-[1-(3-methoxy-phenyl)-2-oxo-pyrrolidin-3-ylamino]-benzamide;
N-Hydroxy-4-[1-(3-isopropoxy-phenyl)-2-oxo-pyrrolidin-3-ylamino]-benzamide;
N-Hydroxy-4-[1-(4-isopropoxy-phenyl)-2-oxo-pyrrolidin-3-ylamino]-benzamide;
N-Hydroxy-4-[2-oxo-1-(3-trifluoromethyl-phenyl)-pyrrolidin-3-ylamino]-benzamide;
N-Hydroxy-4-[2-oxo-1-(4-trifluoromethyl-phenyl)-pyrrolidin-3-ylamino]-benzamide;
N-Hydroxy-4-[1-(3-isopropyl-phenyl)-2-oxo-pyrrolidin-3-ylamino]-benzamide;
N-Hydroxy-4-[1-(4-isopropyl-phenyl)-2-oxo-pyrrolidin-3-ylamino]-benzamide;
4-[1-(4-Butyl-phenyl)-2-oxo-pyrrolidin-3-ylamino]-N-hydroxy-benzamide;
4-[1-(4-tert-Butyl-phenyl)-2-oxo-pyrrolidin-3-ylamino]-N-hydroxy-benzamide;
N-Hydroxy-4-[1-(4-methanesulfonyl-phenyl)-2-oxo-pyrrolidin-3-ylamino]-benzamide;
4-[1-(3-Cyano-phenyl)-2-oxo-pyrrolidin-3-ylamino]-N-hydroxy-benzamide;
4-[1-(4-Cyano-phenyl)-2-oxo-pyrrolidin-3-ylamino]-N-hydroxy-benzamide;
4-[1-(3-Chloro-4-fluoro-phenyl)-2-oxo-pyrrolidin-3-ylamino]-N-hydroxy-benzamide;
4-[1-(3-Chloro-5-fluoro-phenyl)-2-oxo-pyrrolidin-3-ylamino]-N-hydroxy-benzamide;
4-[1-(5-Chloro-2-fluoro-phenyl)-2-oxo-pyrrolidin-3-ylamino]-N-hydroxy-benzamide;
4-[1-(2,4-Dichloro-phenyl)-2-oxo-pyrrolidin-3-ylamino]-N-hydroxy-benzamide;
4-[1-(2,3-Dichloro-phenyl)-2-oxo-pyrrolidin-3-ylamino]-N-hydroxy-benzamide;
4-[1-(3,4-Dichloro-phenyl)-2-oxo-pyrrolidin-3-ylamino]-N-hydroxy-benzamide;
4-[1-(3,5-Dichloro-phenyl)-2-oxo-pyrrolidin-3-ylamino]-N-hydroxy-benzamide;
4-[1-(2,6-Dichloro-phenyl)-2-oxo-pyrrolidin-3-ylamino]-N-hydroxy-benzamide;
4-[1-(4-Fluoro-2,6-dimethyl-phenyl)-2-oxo-pyrrolidin-3-ylamino]-N-hydroxy-benzamide;
4-[1-(4-Chloro-3-hydroxymethyl-phenyl)-2-oxo-pyrrolidin-3-ylamino]-N-hydroxy-benzamide;
N-Hydroxy-4-[2-oxo-1-(3-phenoxy-phenyl)-pyrrolidin-3-ylamino]-benzamide;
N-Hydroxy-4-[2-oxo-1-(4-phenoxy-phenyl)-pyrrolidin-3-ylamino]-benzamide;
4-(1-Biphenyl-3-yl-2-oxo-pyrrolidin-3-ylamino)-N-hydroxy-benzamide;
N-Hydroxy-4-[2-oxo-1-(3-pyrrol-1-yl-phenyl)-pyrrolidin-3-ylamino]-benzamide;
N-Hydroxy-4-[1-(4-imidazol-1-yl-phenyl)-2-oxo-pyrrolidin-3-ylamino]-benzamide;
N-Hydroxy-4-[1-(3-oxazol-5-yl-phenyl)-2-oxo-pyrrolidin-3-ylamino]-benzamide;
4-{1-[3-(2-Dimethylamino-ethoxy)-phenyl]-2-oxo-pyrrolidin-3-ylamino}-N-hydroxy-benzamide;
N-Hydroxy-4-(1-naphthalen-1-yl-2-oxo-pyrrolidin-3-ylamino)-benzamide;
N-Hydroxy-4-(1-naphthalen-2-yl-2-oxo-pyrrolidin-3-ylamino)-benzamide;
N-Hydroxy-4-(2-oxo-1-quinolin-8-yl-pyrrolidin-3-ylamino)-benzamide;
N-Hydroxy-4-(2-oxo-1-quinolin-5-yl-pyrrolidin-3-ylamino)-benzamide;
4-(1-Cyclohexyl-2-oxo-pyrrolidin-3-ylamino)-N-hydroxy-benzamide;
4-(1-Benzyl-5-oxo-pyrrolidin-3-ylamino)-N-hydroxy-benzamide;

N-Hydroxy-4-(2-oxo-1-phenethyl-pyrrolidin-3-ylamino)-benzamide;
N-Hydroxy-4-[5-oxo-1-(R-1-phenyl-ethyl)-pyrrolidin-3-ylamino]-benzamide;
N-Hydroxy-4-[1-(4-methoxy-benzyl)-2-oxo-pyrrolidin-3-ylamino]-benzamide;
N-Hydroxy-4-[1-(1-methyl-1-phenyl-ethyl)-2-oxo-pyrrolidin-3-ylamino]-benzamide;
4-{1-[1-(2-Chloro-phenyl)-1-methyl-ethyl]-2-oxo-pyrrolidin-3-ylamino}-N-hydroxy-benzamide;
4-{1-[1-(3-Chloro-phenyl)-1-methyl-ethyl]-2-oxo-pyrrolidin-3-ylamino}-N-hydroxy-benzamide;
4-{1-[1-(4-Chloro-phenyl)-1-methyl-ethyl]-2-oxo-pyrrolidin-3-ylamino}-N-hydroxy-benzamide;
4-[1-(1-Biphenyl-4-yl-1-methyl-ethyl)-2-oxo-pyrrolidin-3-ylamino]-N-hydroxy-benzamide;
N-Hydroxy-4-[1-(1-methyl-1-naphthalen-1-yl-ethyl)-2-oxo-pyrrolidin-3-ylamino]-benzamide;
N-Hydroxy-4-[1-(1-methyl-1-naphthalen-2-yl-ethyl)-2-oxo-pyrrolidin-3-ylamino]-benzamide;
N-Hydroxy-4-[2-oxo-1-(1-phenyl-cyclobutyl)-pyrrolidin-3-ylamino]-benzamide;
N-Hydroxy-4-[2-oxo-1-(1-phenyl-cyclopentyl)-pyrrolidin-3-ylamino]-benzamide;
N-Hydroxy-4-[2-oxo-1-(1-phenyl-cyclohexyl)-pyrrolidin-3-ylamino]-benzamide;
N-Hydroxy-4-(3-methyl-2-oxo-1-phenyl-pyrrolidin-3-ylamino)-benzamide;
4-[1-(3-Fluoro-phenyl)-3-methyl-2-oxo-pyrrolidin-3-ylamino]-N-hydroxy-benzamide;
4-[1-(3-Chloro-phenyl)-3-methyl-2-oxo-pyrrolidin-3-ylamino]-N-hydroxy-benzamide;
4-[1-(4-Chloro-phenyl)-3-methyl-2-oxo-pyrrolidin-3-ylamino]-N-hydroxy-benzamide;
N-Hydroxy-4-(3-methyl-2-oxo-1-quinolin-3-yl-pyrrolidin-3-ylamino)-benzamide;
N-Hydroxy-4-(3-methyl-2-oxo-1-quinolin-8-yl-pyrrolidin-3-ylamino)-benzamide;
N-Hydroxy-4-(3-methyl-2-oxo-1-quinolin-6-yl-pyrrolidin-3-ylamino)-benzamide;
N-Hydroxy-4-[3-methyl-1-(1-methyl-1-phenyl-ethyl)-2-oxo-pyrrolidin-3-ylamino]-benzamide;
4-[3-Ethyl-1-(1-methyl-1-phenyl-ethyl)-2-oxo-pyrrolidin-3-ylamino]-N-hydroxy-benzamide;
2-Fluoro-N-hydroxy-4-(2-oxo-1-phenyl-pyrrolidin-3-ylamino)-benzamide;
4-[1-(3-Chloro-phenyl)-2-oxo-pyrrolidin-3-ylamino]-2-fluoro-N-hydroxy-benzamide;
4-[1-(3,4-Dichloro-phenyl)-2-oxo-pyrrolidin-3-ylamino]-2-fluoro-N-hydroxy-benzamide;
3-Chloro-N-hydroxy-4-(2-oxo-1-phenyl-pyrrolidin-3-ylamino)-benzamide;
4-[1-(4-Fluoro-phenyl)-5-oxo-pyrrolidin-3-ylamino]-N-hydroxy-benzamide;
4-[1-(2-Chloro-phenyl)-5-oxo-pyrrolidin-3-ylamino]-N-hydroxy-benzamide;
4-[1-(3-Chloro-phenyl)-5-oxo-pyrrolidin-3-ylamino]-N-hydroxy-benzamide;
4-[1-(4-Chloro-phenyl)-5-oxo-pyrrolidin-3-ylamino]-N-hydroxy-benzamide;
N-Hydroxy-4-[1-(3-methoxy-phenyl)-5-oxo-pyrrolidin-3-ylamino]-benzamide;
4-(1-Benzyl-5-oxo-pyrrolidin-3-ylamino)-N-hydroxy-benzamide;
N-Hydroxy-4-[1-(1-methyl-1-phenyl-ethyl)-5-oxo-pyrrolidin-3-ylamino]-benzamide;
Trans-4-[1-(4-Chloro-phenyl)-2-methyl-5-oxo-pyrrolidin-3-ylamino]-N-hydroxy-benzamide;
4-[1-(4-Chloro-phenyl)-4-methyl-5-oxo-pyrrolidin-3-ylamino]-N-hydroxy-benzamide;
N-Hydroxy-4-(1-phenyl-pyrrolidin-3-ylamino)-benzamide;
4-[1-(4-Chloro-phenyl)-pyrrolidin-3-ylamino]-N-hydroxy-benzamide;
4-[1-(2,6-Dichloro-phenyl)-pyrrolidin-3-ylamino]-N-hydroxy-benzamide;
4-[1-(2,4-Dichloro-phenyl)-pyrrolidin-3-ylamino]-N-hydroxy-benzamide;
N-Hydroxy-4-(1-pyrimidin-2-yl-pyrrolidin-3-ylamino)-benzamide;
4-(1-Benzenesulfonyl-pyrrolidin-3-ylamino)-N-hydroxy-benzamide;
4-[1-(4-Fluoro-benzenesulfonyl)-pyrrolidin-3-ylamino]-N-hydroxy-benzamide;
4-[1-(4-Chloro-benzenesulfonyl)-pyrrolidin-3-ylamino]-N-hydroxy-benzamide;
4-[1-(Biphenyl-4-sulfonyl)-pyrrolidin-3-ylamino]-N-hydroxy-benzamide;
4-(1-Benzoyl-pyrrolidin-3-ylamino)-N-hydroxy-benzamide;
4-[1-(4-Fluoro-benzoyl)-pyrrolidin-3-ylamino]-N-hydroxy-benzamide;
N-Hydroxy-4-[1-(4-methoxy-benzoyl)-pyrrolidin-3-ylamino]-benzamide;
4-(1-Benzyl-3-methyl-2-oxo-2,3-dihydro-1H-indol-3-ylamino)-N-hydroxy-benzamide;
4-[1-2-Chloro-benzyl)-3-methyl-2-oxo-2,3-dihydro-1H-indol-3-ylamino)-N-hydroxy-benzamide;
4-[1-(3-Chloro-benzyl)-3-methyl-2-oxo-2,3-dihydro-1H-indol-3-ylamino)-N-hydroxy-benzamide;
N-Hydroxy-4-(3-methyl-2-oxo-1-phenethyl-2,3-dihydro-1H-indol-3-ylamino)-benzamide;
N-Hydroxy-4-(3-methyl-2-oxo-1-phenyl-2,3-dihydro-1H-indol-3-ylamino)-benzamide;
4-[1-(3-Chloro-phenyl)-3-methyl-2-oxo-2,3-dihydro-1H-indol-3-ylamino]-N-hydroxy-benzamide;
4-[1-(4-Chloro-phenyl)-5-fluoro-3-methyl-2-oxo-2,3-dihydro-1H-indol-3-ylamino]-N-hydroxy-benzamide;
4-[1-(3-Chloro-phenyl)-5-fluoro-3-methyl-2-oxo-2,3-dihydro-1H-indol-3-ylamino]-N-hydroxy-benzamide;
4-[1-(2-Chloro-benzyl)-5-fluoro-3-methyl-2-oxo-2,3-dihydro-1H-indol-3-ylamino]-N-hydroxy-benzamide; and
4-[1-(3-Chloro-phenyl)-3-methyl-2-oxo-2,3-dihydro-1H-pyrrolo[3,2-c]pyridin-3-ylamino]-N-hydroxy-benzamide.

Further particular compounds of formula (I) or a pharmaceutically acceptable salt, ester or stereoisomers thereof, according to the invention can be selected from can be selected from 4-[1-(3-Fluoro-phenyl)-2-oxo-pyrrolidin-3-ylamino]-N-hydroxy-benzamide;
4-[1-(4-Fluoro-phenyl)-2-oxo-pyrrolidin-3-ylamino]-N-hydroxy-benzamide;
4-[1-(4-Chloro-phenyl)-2-oxo-pyrrolidin-3-ylamino]-N-hydroxy-benzamide;
4-[1-(3-Cyano-phenyl)-2-oxo-pyrrolidin-3-ylamino]-N-hydroxy-benzamide;
4-[1-(4-Cyano-phenyl)-2-oxo-pyrrolidin-3-ylamino]-N-hydroxy-benzamide;
4-[1-(3-Chloro-4-fluoro-phenyl)-2-oxo-pyrrolidin-3-ylamino]-N-hydroxy-benzamide;
4-[1-(3-Chloro-5-fluoro-phenyl)-2-oxo-pyrrolidin-3-ylamino]-N-hydroxy-benzamide;
4-[1-(2,6-Dichloro-phenyl)-2-oxo-pyrrolidin-3-ylamino]-N-hydroxy-benzamide;

4-{1-[3-(2-Dimethylamino-ethoxy)-phenyl]-2-oxo-pyrrolidin-3-ylamino}-N-hydroxy-benzamide;
N-Hydroxy-4-(2-oxo-1-quinolin-5-yl-pyrrolidin-3-ylamino)-benzamide;
4-(1-Benzyl-5-oxo-pyrrolidin-3-ylamino)-N-hydroxy-benzamide;
N-Hydroxy-4-[5-oxo-1-(R-1-phenyl-ethyl)-pyrrolidin-3-ylamino]-benzamide;
N-Hydroxy-4-[1-(1-methyl-1-phenyl-ethyl)-2-oxo-pyrrolidin-3-ylamino]-benzamide;
4-{1-[1-(3-Chloro-phenyl)-1-methyl-ethyl]-2-oxo-pyrrolidin-3-ylamino}-N-hydroxy-benzamide;
4-{1-[1-(4-Chloro-phenyl)-1-methyl-ethyl]-2-oxo-pyrrolidin-3-ylamino}-N-hydroxy-benzamide;
N-Hydroxy-4-[2-oxo-1-(1-phenyl-cyclobutyl)-pyrrolidin-3-ylamino]-benzamide;
N-Hydroxy-4-[2-oxo-1-(1-phenyl-cyclohexyl)-pyrrolidin-3-ylamino]-benzamide;
4-[1-(4-Chloro-phenyl)-3-methyl-2-oxo-pyrrolidin-3-ylamino]-N-hydroxy-benzamide;
N-Hydroxy-4-(3-methyl-2-oxo-1-quinolin-3-yl-pyrrolidin-3-ylamino)-benzamide;
N-Hydroxy-4-(3-methyl-2-oxo-1-quinolin-8-yl-pyrrolidin-3-ylamino)-benzamide;
N-Hydroxy-4-(3-methyl-2-oxo-1-quinolin-6-yl-pyrrolidin-3-ylamino)-benzamide;
N-Hydroxy-4-[3-methyl-1-(1-methyl-1-phenyl-ethyl)-2-oxo-pyrrolidin-3-ylamino]-benzamide;
2-Fluoro-N-hydroxy-4-(2-oxo-1-phenyl-pyrrolidin-3-ylamino)-benzamide;
3-Chloro-N-hydroxy-4-(2-oxo-1-phenyl-pyrrolidin-3-ylamino)-benzamide;
4-[1-(4-Fluoro-phenyl)-5-oxo-pyrrolidin-3-ylamino]-N-hydroxy-benzamide;
4-[1-(4-Chloro-phenyl)-5-oxo-pyrrolidin-3-ylamino]-N-hydroxy-benzamide;
Trans-4-[1-(4-Chloro-phenyl)-2-methyl-5-oxo-pyrrolidin-3-ylamino]-N-hydroxy-benzamide;
4-[1-(4-Chloro-phenyl)-4-methyl-5-oxo-pyrrolidin-3-ylamino]-N-hydroxy-benzamide;
4-[1-(2,6-Dichloro-phenyl)-pyrrolidin-3-ylamino]-N-hydroxy-benzamide;
N-Hydroxy-4-(1-pyrimidin-2-yl-pyrrolidin-3-ylamino)-benzamide;
4-[1-(4-Fluoro-benzenesulfonyl)-pyrrolidin-3-ylamino]-N-hydroxy-benzamide;
4-[1-(4-Fluoro-benzoyl)-pyrrolidin-3-ylamino]-N-hydroxy-benzamide;
4-[1-2-Chloro-benzyl)-3-methyl-2-oxo-2,3-dihydro-1H-indol-3-ylamino)-N-hydroxy-benzamide;
4-[1-(3-Chloro-phenyl)-3-methyl-2-oxo-2,3-dihydro-1H-indol-3-ylamino)-N-hydroxy-benzamide;
4-[1-(2-Chloro-benzyl)-5-fluoro-3-methyl-2-oxo-2,3-dihydro-1H-indol-3-ylamino]-N-hydroxy-benzamide; and
4-[1-(3-Chloro-phenyl)-3-methyl-2-oxo-2,3-dihydro-1H-pyrrolo[3,2-c]pyridin-3-ylamino]-N-hydroxy-benzamide.

The compounds of the present invention can be prepared by any conventional means. Suitable processes for synthesizing these compounds as well as their starting materials are provided in the schemes below and in the examples. All substituents, in particular, $R^1$ to $R^4$, Y and A are as defined above unless otherwise indicated. Furthermore, and unless explicitly otherwise stated, all reactions, reaction conditions, abbreviations and symbols have the meanings well known to a person of ordinary skill in organic chemistry.

Abbreviation:
Boc: tert-butoxycarbonyl
d: day
DIPEA: diisopropylethylamine
DMAP: 4-N,N-dimethylaminopyridine
DMF: dimethylformamide
DMSO: dimethylsulfoxide
ECL: enhanced chemiluminescence
EDCI: 1-ethyl-3-(3-dimethylaminopropyl)carbodiimide
ELISA: enzyme-linked immunosorbent assay
EtOAc: ethyl acetate
exp: experimental
FBS: fetal bovine serum
g: gram
$EC_{50}$: concentration required for 50% induction of acetylated tubulin
$IC_{50}$: concentration required for 50% enzymatic inhibition of HDAC8
h: hour
HDAC: histone deacetylase
HPLC: high performance liquid chromatography
HRP: horseradish peroxidase
Hz: Hertz
KOH: potassium hydroxide
LDA: lithium diisopropylamide
MeOD: deuterated methanol
MeOH: methanol
mg: milligram
MHz: megahertz
mL: milliliter
MM: multiple myeloma
mmol: millimole
NAD: nicotinamide adenine dinucleotide
NaOH: sodium hydroxide
NB: neuroblastoma
$NEt_3$: triethylamine
NMR: nuclear magnetic resonance
rt: room temperature
SAHA: suberoylanilide hydroxamic acid
TBS: tris-buffered saline
t-BuOK: potassium tert-butoxide
TFA: trifluoroacetic acid
THF: tetrahydrofuran
μl: microliter
μM: micromole
WST: 4-[3-(4-iodophenyl)-2-(4-nitrophenyl)-2H-5-tetrazolio]-1,3-benzene disulfonate Scheme 1: General synthetic scheme for 3-aminopyrrolidinone based analogues (Ia).

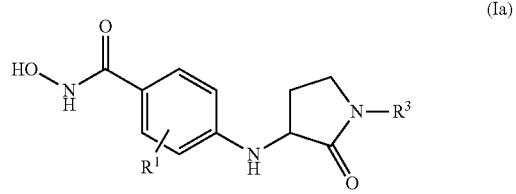

(Ia)

Compounds of interest (Ia) can be prepared according to the general synthesis method shown in Scheme 1.

Scheme 1

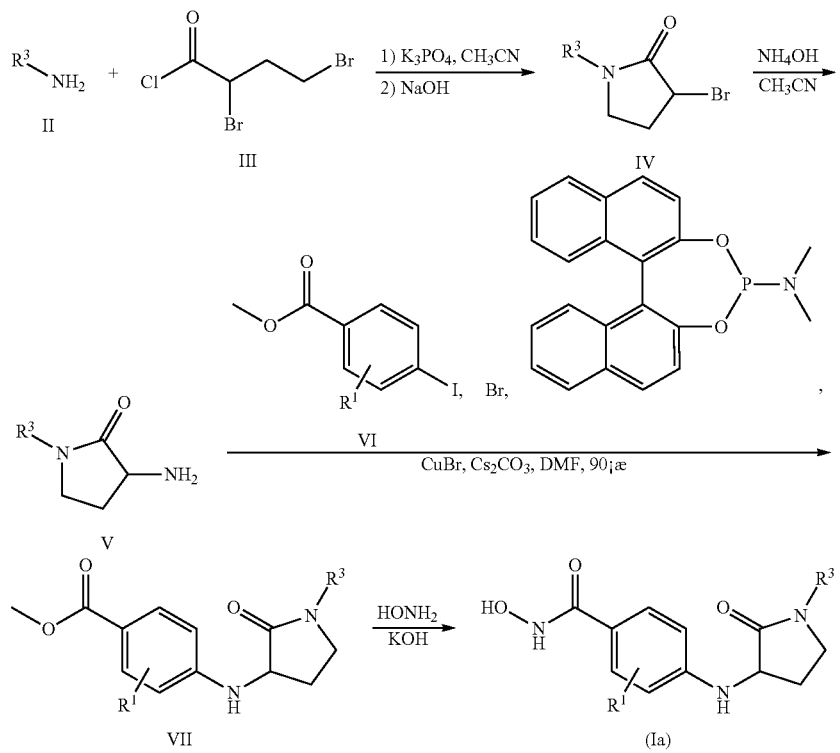

Starting from amine II and 2,4-dibromo-butyryl chloride III, the coupling reaction under potassium phosphate in acetonitrile gives amide, which is converted to bromide intermediate IV through NaOH mediated ring closure.

The aminopyrrolidinone V can be prepared by amination reaction of bromide IV. The reaction is typically performed in acetonitrile and ammonia at 60° C. for 4 hour.

The ester VII can be prepared by copper catalyzed Ullmann coupling reaction of amine V and 4-bromobenzoate ester VI. Alternatively, 4-iodobenzoate ester VI can be used in the coupling reaction in place of 4-bromobenzoate ester. The reaction is typically performed in DMF with cuprous bromide, cesium carbonate, and phosphorus ligand such as (S)-monophos at 90° C.

The N-hydroxyl benzamide analogs (Ia) can be prepared by the treatment of methyl ester VII with 50% hydroxylamine solution. The reaction is typically carried out in a mixture of MeOH and aqueous KOH at rt for one hour.

Scheme 2: General synthetic scheme for 3-amino-3-alkylpyrrolidinone based analogues (Ib).

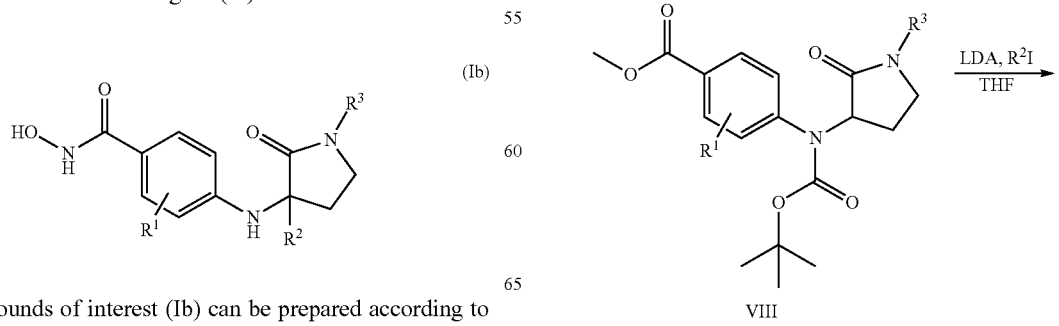

Compounds of interest (Ib) can be prepared according to the general synthesis method shown in Scheme 2.

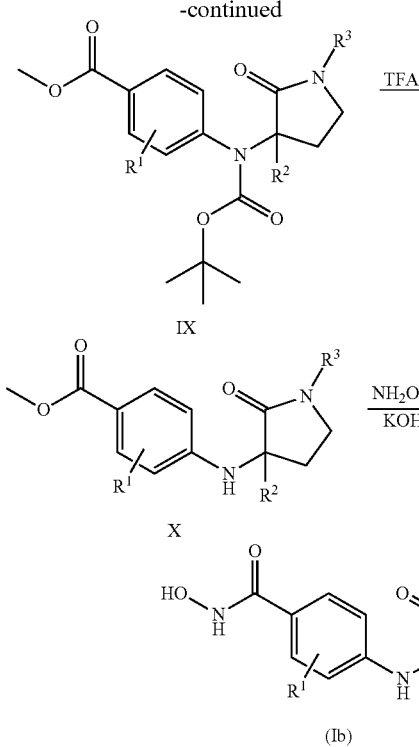

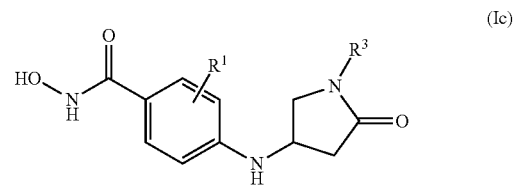

can be carried out with a suitable organic base such as triethylamine (NEt$_3$) in an inert organic solvent such as dichloromethane, typically at rt for five hours.

Compound IX can be prepared by the alkylation of ester VIII. The reaction is typically carried out in anhydrous THF with LDA added at −78° C. After half an hour, iodoalkane is added and the reaction mixture is stirred at −78° C. When the reaction is brought to rt, it is quenched with saturated aqueous ammonium chloride.

Compound X can be obtained by the deprotection of IX. The reaction is typically performed in dichloromethane with TFA or in MeOH with hydrochloride as deprotective agent at rt.

The N-hydroxyl benzamide analogs (Ib) can be prepared by the treatment of methyl ester X with 50% hydroxylamine solution. The reaction was typically carried out in a mixture of MeOH and aqueous KOH at rt for about one hour.

Scheme 3: General synthetic scheme for 4-aminopyrrolidinone based analogues (Ic).

Boc-protected compound VIII can be obtained by the reaction of ester VII with di-tert-butyldicarbonate. The reaction Compounds of interest (Ic) can be prepared according to the general synthesis method shown in Scheme 3.

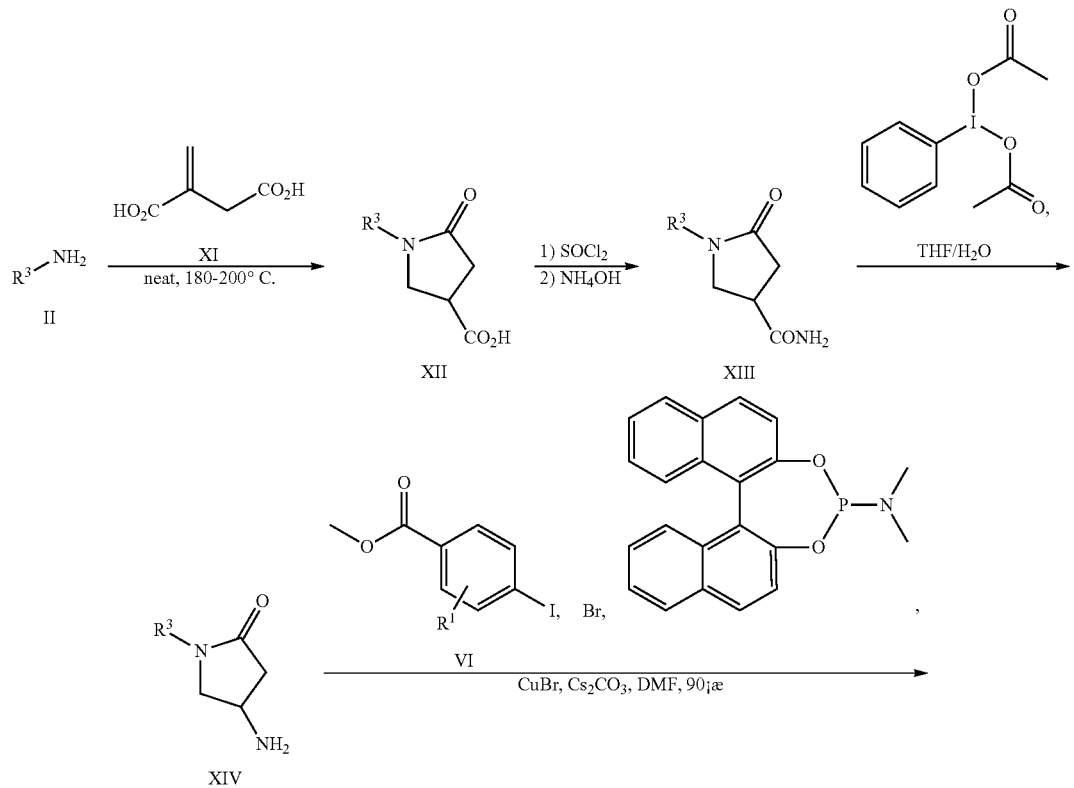

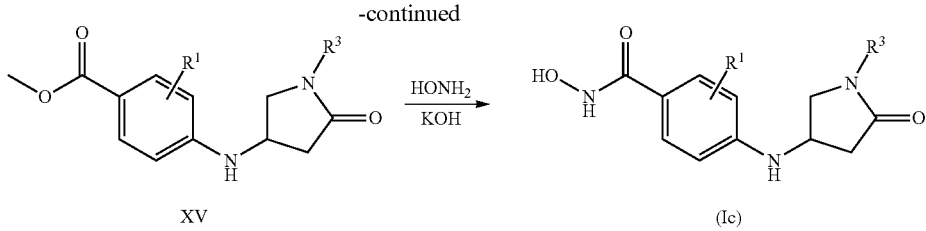

The acid XII can be prepared by addition and lactam formation from amine II and commercial available itaconic acid XI. The reaction is typically performed without solvent at 180~200° C. for 0.5 hr.

Compound XIII can be prepared by amination from acid XII. Firstly, thionyl chloride is added to a solution of acid XII in 1,2-dichloroethane and the mixture is heated at 80° C. for 1 hour. After removal of solvent, the residue is dissolved in THF and ammonia aqueous solution is added dropwised into the mixture to afford amide XIII.

The amine XIV can be prepared by Hofmann rearrangement of XIII. The reaction is typically carried out in THF and water with (diacetoxyiodo)benzene as oxidant at rt.

The ester XV can be prepared by copper-catalyst reaction from amine XIV with ester VI. The reaction is typically performed at 90° C. in DMF with cuprous bromide, cesium carbonate, and phosphorus ligand such as monophus as shown in Scheme 3.

The analogs (Ic) can be prepared by the treatment of methyl ester XV with 50% hydroxylamine solution. The reaction is typically carried out in a mixture of MeOH and aqueous KOH at rt.

Scheme 4: General synthetic scheme for 4-amino-5-alkylpyrrolidinone based analogues (Id).

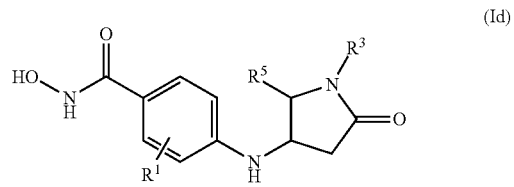

wherein $R^1$ and $R^3$ has the same meaning as given above, and $R^5$ is alkyl.

Compounds of interest (Id) can be prepared according to the general synthesis method shown in Scheme 4.

Scheme 4

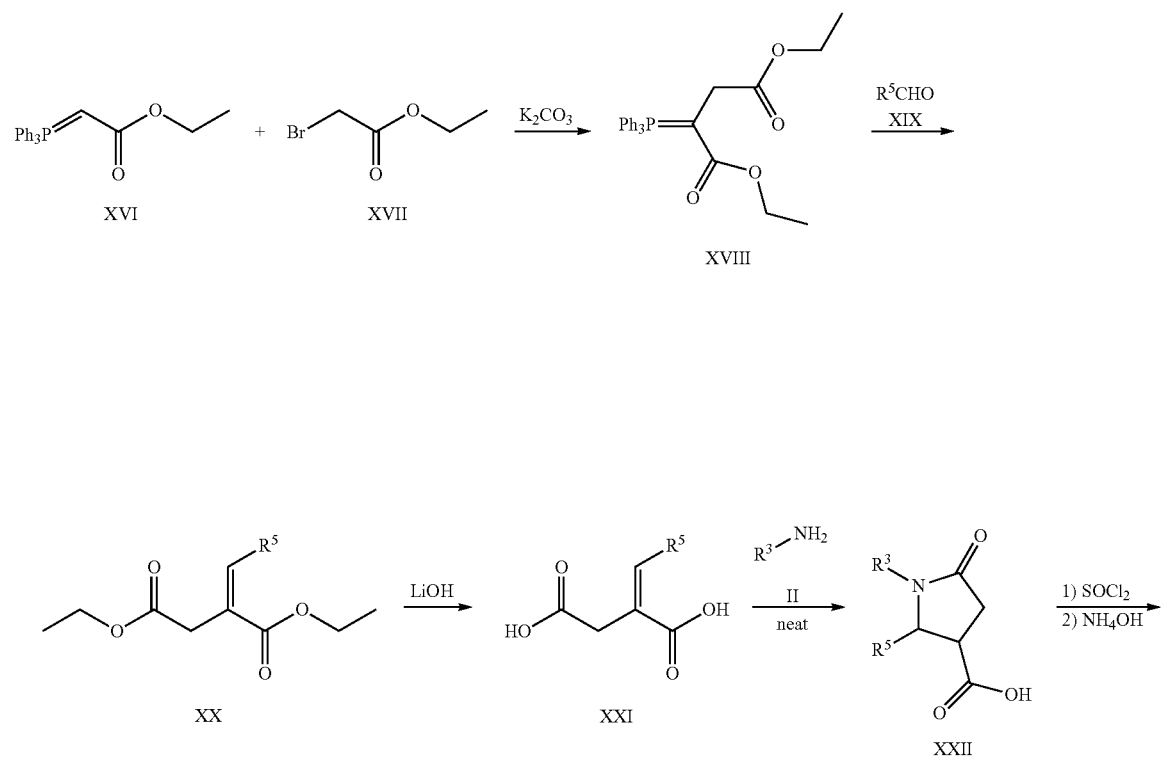

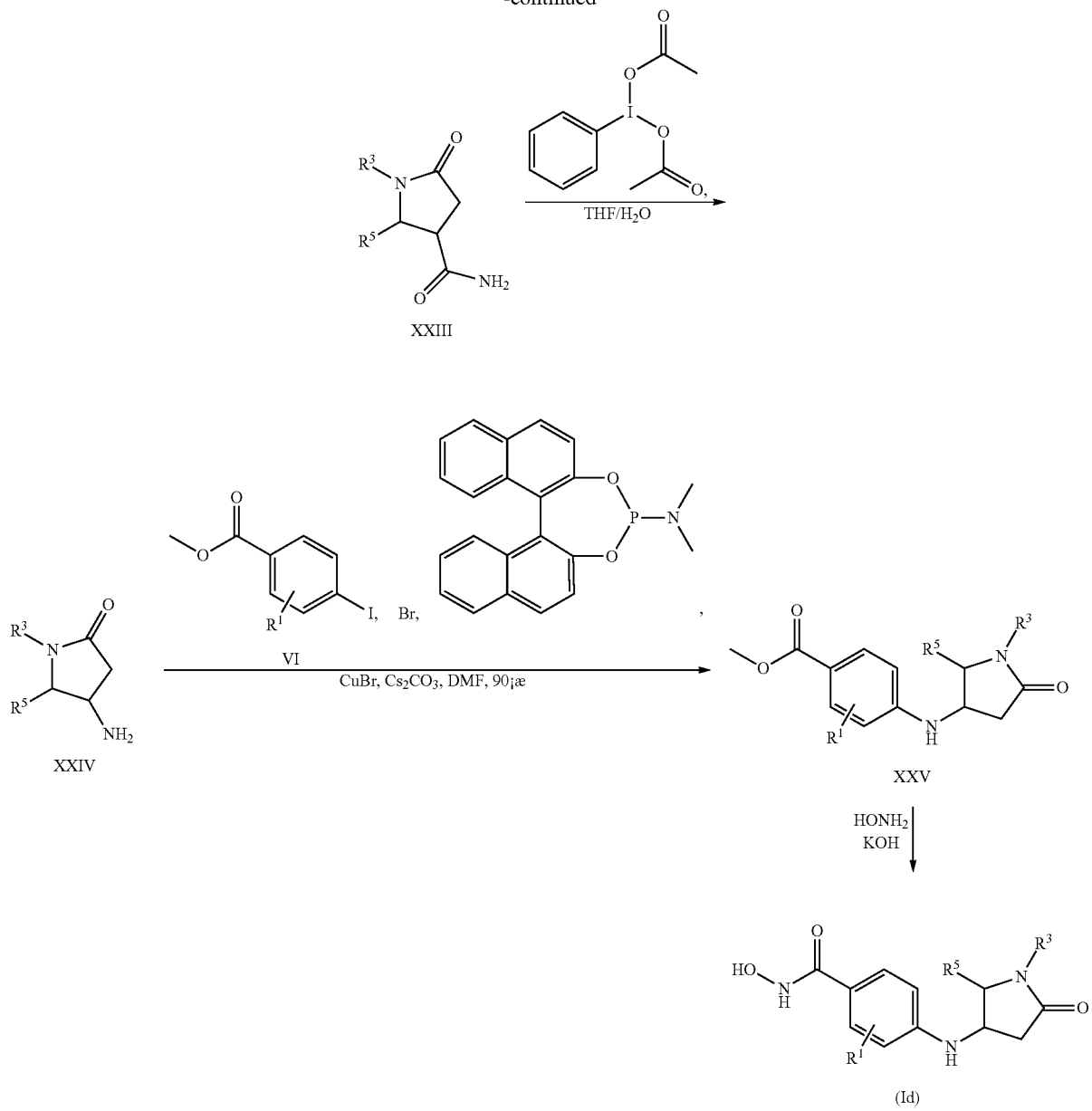

Ylide XVIII can be prepared by from commercial available XVI and XVII with suitable base. The reaction is typically carried out in EtOAc with potassium carbonate under refluxing conditions.

Compound XX can be prepared by the Wittig reaction from glide XVIII with aldehyde XIX ($R^5$CHO). The reaction is typically performed in dichloromethane at rt.

Carboxylic acid XXI can be prepared from the hydrolysis of XX under basic conditions. The reaction is typically performed with lithium hydroxide as base in aqueous MeOH at rt for 4 hours.

The acid XXII can be prepared by concentration from commercial available amine II and diacid XXI. The reaction is typically performed under neat at 180~200° C. for 0.5 hr.

Compound XXIII can be prepared by amination from acid XXII. Firstly, thionyl chloride is added to a solution of acid XXII in 1,2-dichloroethane and the mixture is heated at 80° C. for 1 hour. The solvent is removed to afford carbonyl chloride. Then the residue is dissolved in THF and aqueous ammonia is added dropwised to afford amide XXIII.

The amine XXIV can be prepared by the Hofmann rearrangement reaction of XXIII. The reaction is typically carried out in aqueous THF with (diacetoxyiodo)benzene as oxidant at rt.

The ester XXV can be prepared by copper-catalyst reaction from amine XXIV with ester VI. The reaction is typically performed in DMF with cuprous bromide, cesium carbonate, and phosphorus ligand at 90° C. overnight. The cis- and trans-isomers of XXV can be separated through chromatographic purifications.

The analogs (Id) can be prepared by treatment of methyl ester XXV with 50% hydroxylamine solution. The reaction is typically carried out in a mixture of MeOH and aqueous KOH at rt for one hour.

Scheme 5: General synthetic scheme for 4-amino-3-alkylpyrrolidinone based analogues (Ie).

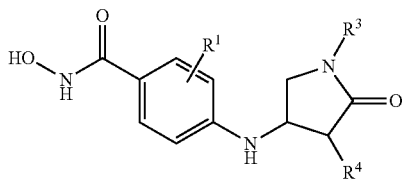

Compounds of interest (Ie) can be prepared according to the general synthesis method shown in Scheme 5.

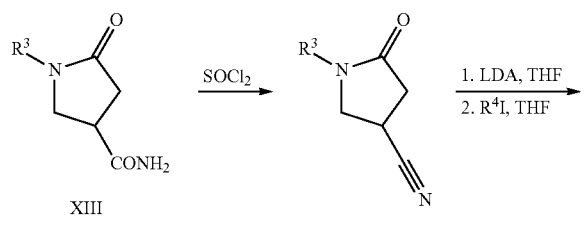

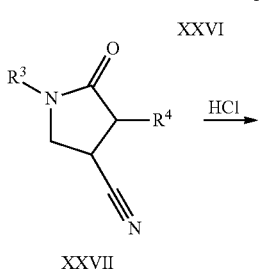

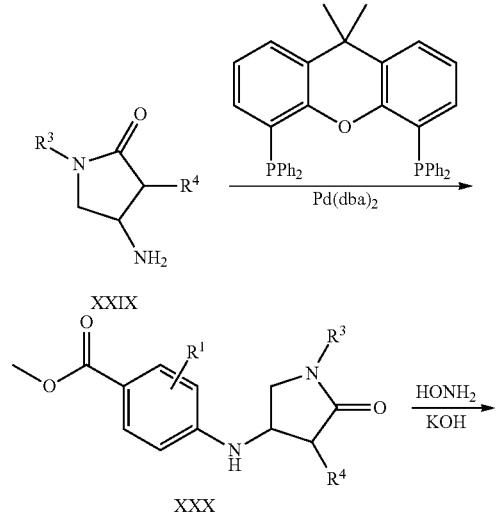

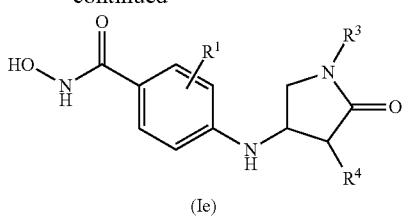

Compound XXVI can be prepared by the dehydration of amide XIII. The reaction is typically carried out with thionyl chloride in 1,2-dichloroethane at 80° C. for 3 hr.

Compound XXVII can be prepared through the alkylation of nitrile XXVI. The reaction is typically carried out in anhydrous THF with LDA at −78° C., then iodoalkane ($R^4I$) is added and stirred at −78° C. When the reaction is brought to rt, it is quenched with saturated aqueous ammonium chloride.

Compound XXVIII can be prepared by the hydrolysis of nitrile XXVII under acidic conditions. The reaction is typically carried out in HCl (6 N) at rt.

The amine XXIX can be prepared by the Hofmann rearrangement reaction of XXVIII. The reaction is typically carried out in aqueous THF with (diacetoxyiodo)benzene as oxidant at rt.

The ester XXX can be prepared by palladium-catalyzed coupling reaction from amine XXIX with ester VI. The reaction is typically performed in DMF with $Pd(dba)_2$, cesium carbonate, and phosphorus ligand at 110° C. overnight. The cis- and trans-isomers of XXX can be separated through chromatographic purifications.

The analogs (Ie) can be prepared by the treatment of methyl ester XXX with 50% hydroxylamine solution. The reaction is typically carried out in a mixture of MeOH and aqueous KOH at rt for one hour.

Scheme 6: General synthetic scheme for 3-amino-3-alkylpyrrolidine based analogues (If). 3-amino-2-alkylpyrrolidine based analogues (Ig), and 3-amino-4-alkylpyrrolidine based analogues (Ih).

One category of the compounds described herein relates to 3-amino-3-alkylpyrrolidine based analogues (If), 3-amino-2-alkylpyrrolidine based analogues (Ig) and 3-amino-4-alkylpyrrolidine based analogues (Ih).

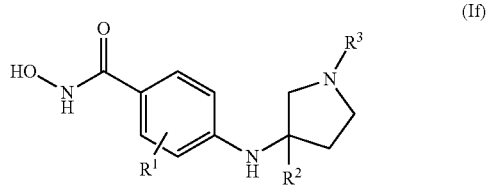

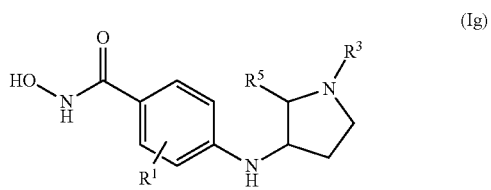

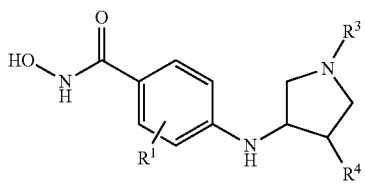

wherein $R^1$, $R^2$, $R^3$, and $R^4$ have the significances given before, and $R^5$ is alkyl.

Compounds of interest (If), (Ig) and (Ih) can be prepared according to the general synthesis methods shown in Scheme 6.

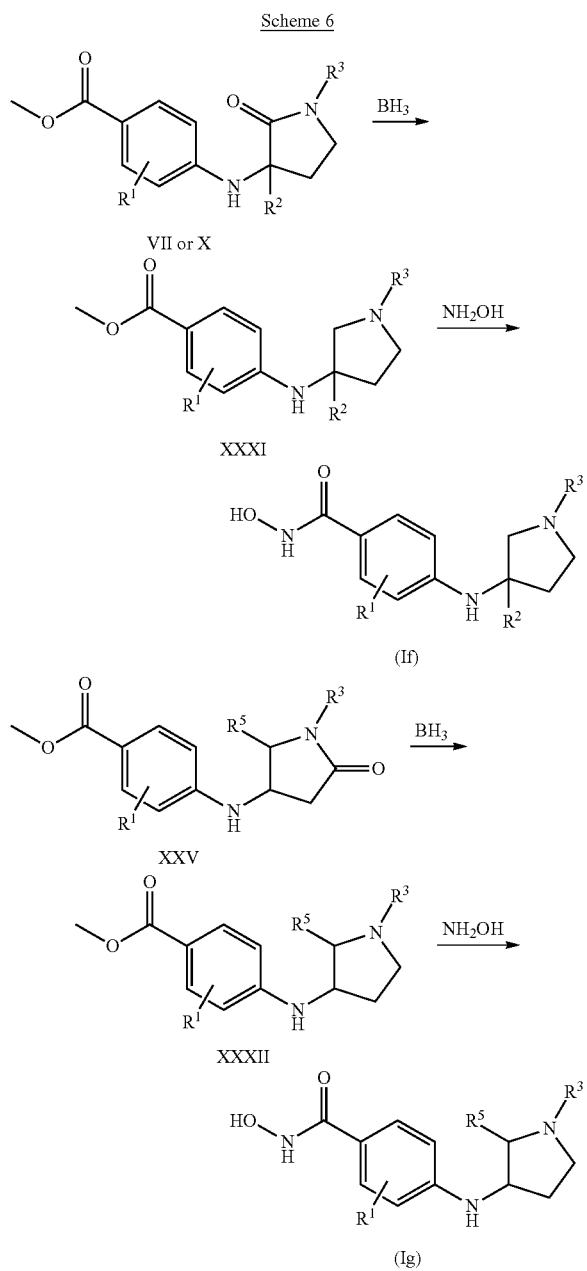

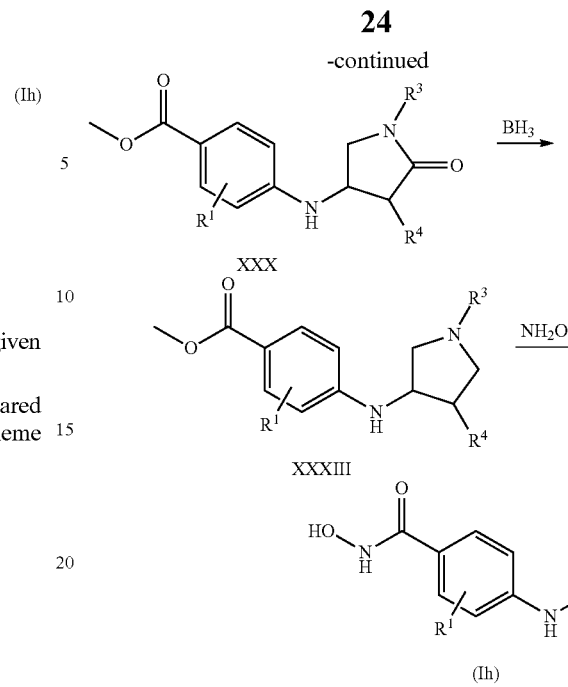

Compound XXXI can be prepared by the reduction of lactam VII or X with suitable reductive reagents. The reaction is typically performed in borane-THF complex solution under refluxing conditions for overnight.

The analogs (If) can be prepared by the treatment of methyl ester XXXI with 50% hydroxylamine solution. The reaction is typically carried out in a mixture of MeOH and aqueous KOH at rt for one hour.

Compound XXXII can be prepared by the reduction reaction of lactam XXV with suitable reductive reagents. The reaction is typically performed in borane-THF complex solution under refluxing conditions for overnight.

The analogs (Ig) can be prepared by the treatment of methyl ester XXXII with 50% hydroxylamine solution. The reaction is typically carried out in a mixture of MeOH and aqueous KOH at rt for one hour.

Compound XXXIII can be prepared by the reduction reaction of lactam XXX with suitable reductive reagents. The reaction is typically performed in borane-THF complex solution under refluxing conditions for overnight.

The analogs (Ih) can be prepared by the treatment of ester XXXIII with 50% hydroxylamine solution. The reaction is typically carried out in a mixture of MeOH and aqueous KOH at rt for one hour.

Scheme 7: General synthetic scheme for 3-aminopyrrolidine sulfonamide based analogues (Ii).

One category of the compounds described herein relates to 3-aminopyrrolidine sulfonamide based analogues with the formula (Ii)

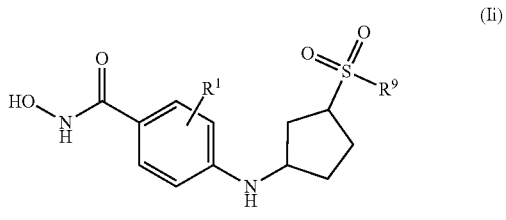

wherein R[1] has the significance given before; and R[9] is phenyl wherein phenyl can be unsubstituted or once or twice substituted by halogen, phenyl, alkoxy, alkyl, cyano, alkylsulfonyl, trifluoromethyl, phenoxy, pyrrolyl, imidazonyl, oxazolyl or dialkylaminoalkoxy.

Compounds of interest (Ii) can be prepared according to the general synthesis method shown in Scheme 7.

Scheme 7

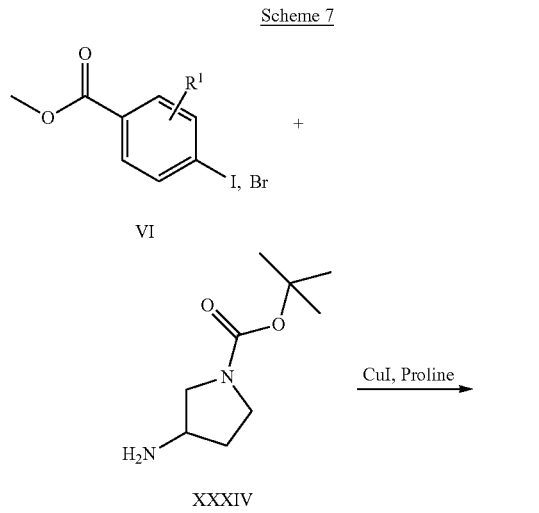

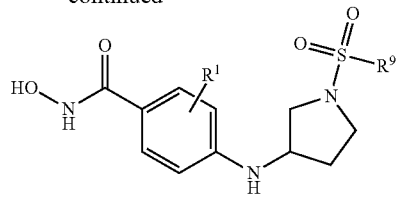

(Ii)

Compound XXXV can be prepared by the copper-catalyzed coupling of amine XXXIV with ester VI. The reaction is typically performed in deoxygenated DMF with cecium carbonate, cuprous iodide, L-proline at 110° C. under inert atmosphere.

Compound XXXVI can be obtained by the deprotection of XXXV. The reaction is typically carried out by methanolic hydrogen chloride at rt.

Sulfonamide XXXVII can be prepared from the coupling of amine XXXVI with sulfonyl chlorides (R[9]SO$_2$Cl). The reaction is typically performed with DIPEA or NEt$_3$ as base in a suitable inert solvent such as THF, dichloromethane, DMF, or their mixtures at rt.

Compounds of interest (Ii) are obtained by the treatment of ester XXXVII with 50% hydroxylamine solution. The reaction is typically performed in MeOH with a suitable base such as KOH.

Scheme 8: General synthetic scheme for 3-aminopyrrolidine amide based analogues (Ij).

One category of the compounds described herein relates to 3-aminopyrrolidine amide based analogues with the formula (Ij)

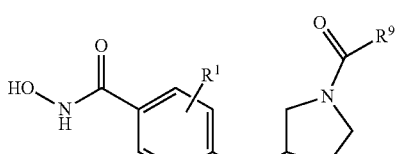

(Ij)

wherein R[1] has the significances given before; and R[9] is phenyl wherein phenyl can be unsubstituted or once or twice substituted by halogen, phenyl, alkoxy, alkyl, cyano, alkylsulfonyl, trifluoromethyl, phenoxy, pyrrolyl, imidazonyl, oxazolyl or dialkylaminoalkoxy.

Compounds of interest (Ij) can be prepared according to the general synthesis method shown in Scheme 8.

Scheme 8

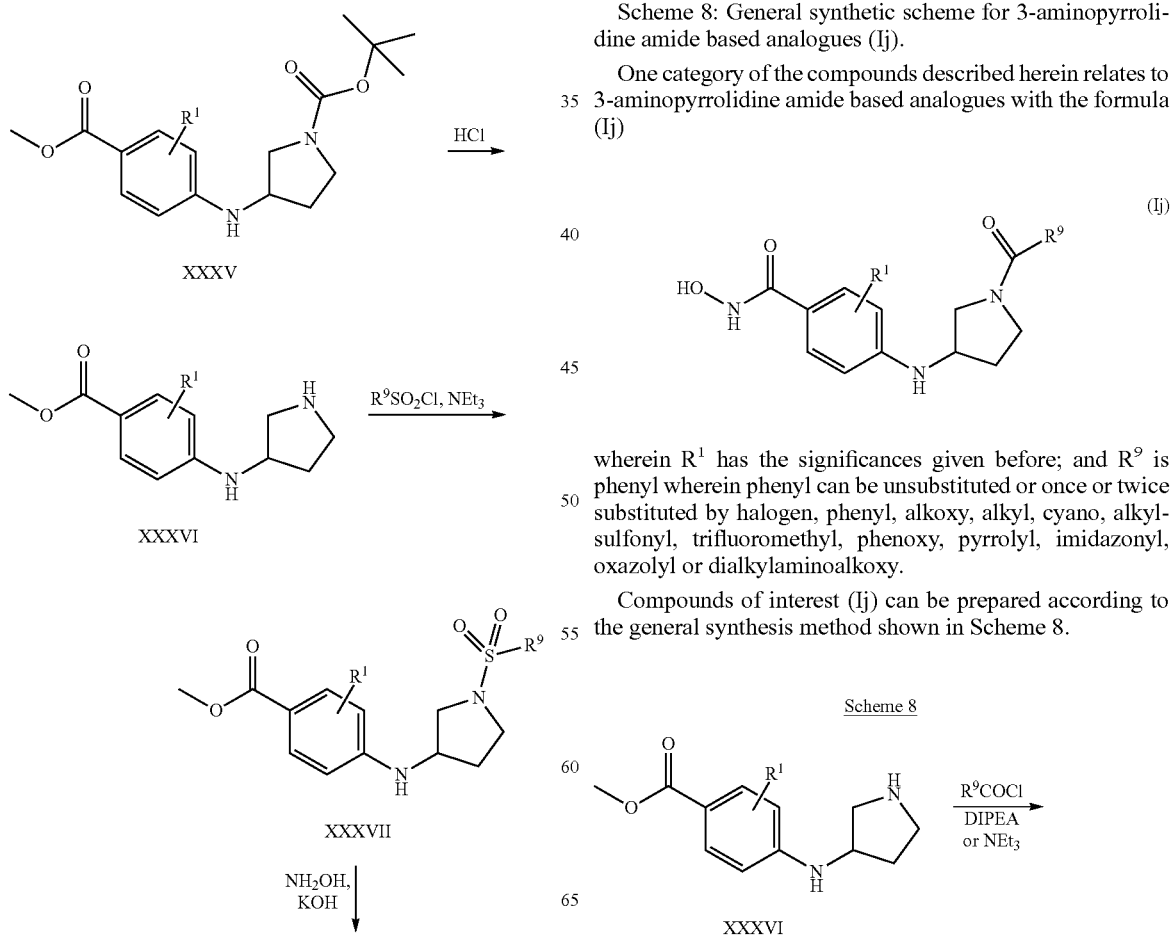

-continued

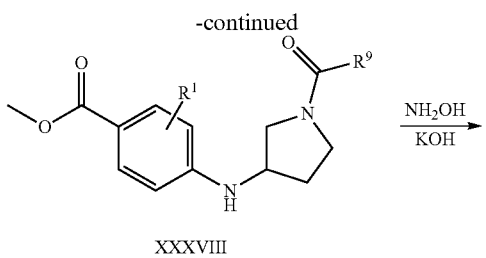

XXXVIII

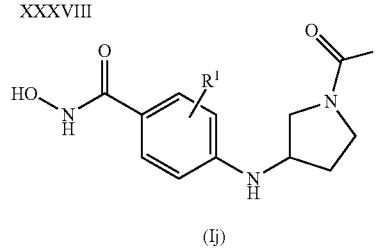

(Ij)

Amide XXXVIII can be prepared from the coupling of amine XXXVI with carbonyl chlorides (R⁹COCl). The reaction is typically performed under standard carbonylation conditions with DIPEA or NEt₃ as base in a suitable inert solvent such as THF, dichloromethane, DMF, or their mixtures solvent at rt.

Compounds of interest (Ij) are obtained by the treatment of ester XXXVIII with 50% hydroxylamine solution. The reaction is typically performed in MeOH with a suitable base such as KOH.

Scheme 9: General synthetic scheme for 3-alkyl-3-phenylamino-1,3-dihydroindol-2-one based analogues (Ik) and 3-alkyl-3-phenylamino-aza-oxindole based analogues (Il).

One category of the compounds described herein are 3-alkyl-3-phenylamino-oxindole based analogues with the core structure as shown in formula (Ik), wherein R¹ and R³ have the significances as given before, and R² is alkyl. Another category of the compounds are 3-alkyl-3-phenylamino-aza-oxindole based analogues with the core structure as shown in formula (Il), wherein R¹ and R³ have the significances given before, and R² is alkyl.

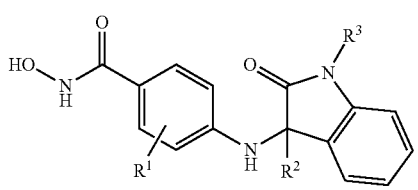

(Ik)

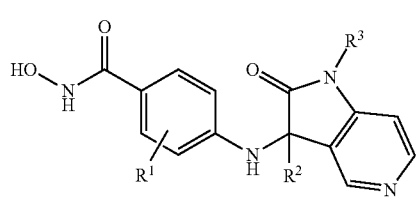

(Il)

Compounds of interest (Ik) can be prepared according to the general synthesis method shown in Scheme 9.

Scheme 9

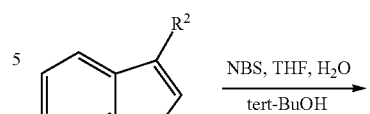

XXXIX

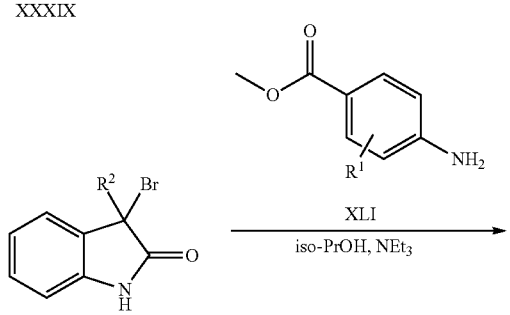

XL

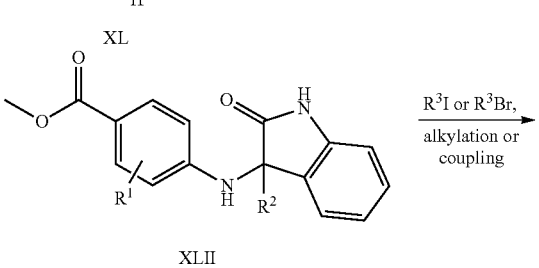

XLII

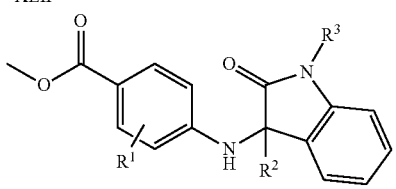

XLIII

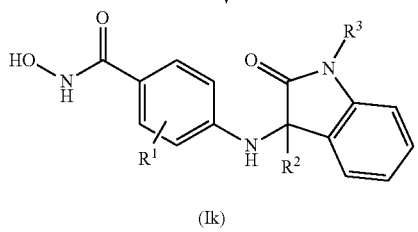

(Ik)

Oxindole XL can be prepared from commercially available 3-alkyl-1H-indole XXXIX with NBS as oxidant. The reaction is typically performed in a mixture of THF, water and tert-BuOH at rt.

Compound XLII can be prepared from the replacement of bromide XL with 4-aminobenzoate ester XLI. The reaction is typically carried out in isopropanol with DIPEA or NEt₃ as base at rt.

Compound XLIII can be prepared from compound XLII, and haloalkane or aromatic bromide through the alkylation reactions or copper-catalyzed coupling reactions. The alkylation reaction is typically carried out with K₂CO₃ in a suitable inert solvent such as THF, DMF at rt. Whereas the copper-catalyzed coupling is performed in DMF with cuprous bromide, cesium carbonate, and phosphorus ligand at 90° C.

Compounds of interest (Ik) are obtained by the treatment of esters XLIII with 50% hydroxylamine solution. The reaction is typically performed in MeOH with a suitable base such as KOH.

The synthesis of formula (II) can be carried out in the same way as analogs (Ik) by using 3-alkyl-1H-pyrrolo[3,2-c]pyridine in place of 3-alkyl-1H-indole XXXIX.

Scheme 10: General synthetic scheme for 3-alkyl-3-phenylamino-1,3-dihydroindol-2-one based analogues (Im).

One category of the compounds described herein relates to 3-alkyl-3-phenylamino-oxindole based analogues with the structure as shown in formula (Im), wherein $R^1$ and $R^3$ have the significances given before, $R^2$ is alkyl, and $R^{10}$ is halogen.

Compounds of interest (Im) can be prepared according to the general synthesis method shown in Scheme 10:

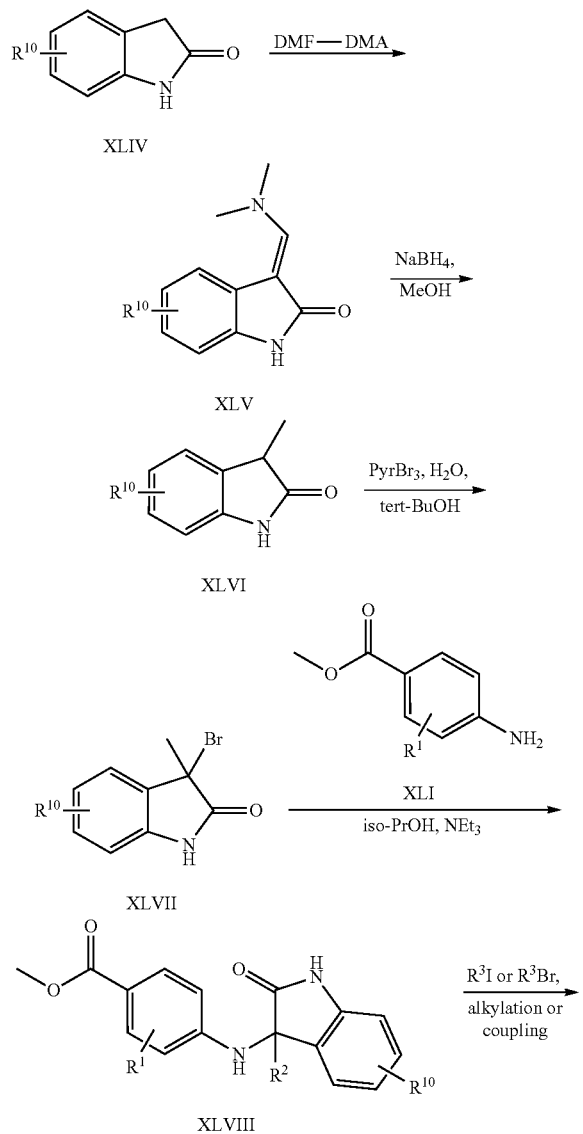

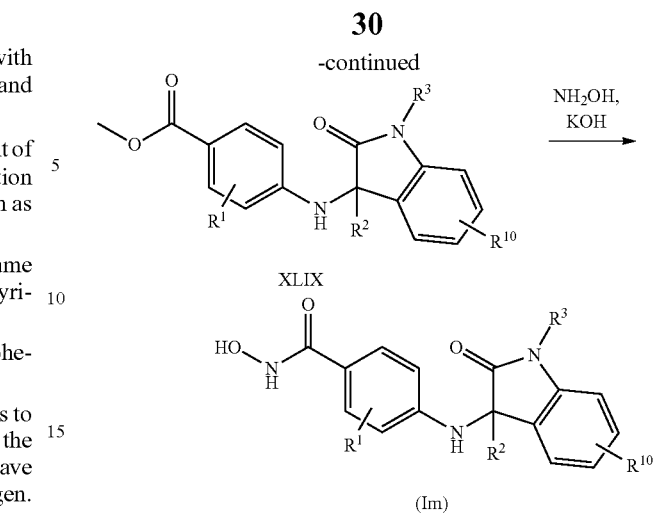

Compound XLV is prepared from the condensation reaction between oxindole XLIV and N,N-dimethylformamide dimethyl acetal (DMF-DMA). The reaction is typically carried out in dry THF at rt.

Compound XLVI can be prepared by the reduction of compound XLV with $NaBH_4$ in MeOH at rt.

Compound XLVII can be prepared from the bromination of compound XLVI with pyridinium tribromide. The reaction is typically performed in aqueous tert-BuOH at rt.

Compound XLVIII can be prepared from the replacement of bromide XLVII with 4-aminobenzoate ester XLI. The reaction is typically carried out in isopropanol with DIPEA or $NEt_3$ as base at rt.

Compound XLIX can be prepared from compound XLVIII, and haloalkane or aromatic bromide through the alkylation reactions or copper-catalyzed coupling reactions. The alkylation reaction is typically carried out with $K_2CO_3$ in a suitable inert solvent such as THF, DMF at rt. Whereas the copper-catalyzed coupling is performed in DMF with cuprous bromide, cesium carbonate, and phosphorus ligand at 90° C.

Compounds of interest (Im) are obtained by the treatment of esters XLIX with 50% hydroxylamine solution. The reaction is typically performed in MeOH with a suitable base such as KOH.

The invention also relates to a process for preparing a compound of formula (I), which process comprises hydrolysis a compound of formula (A)

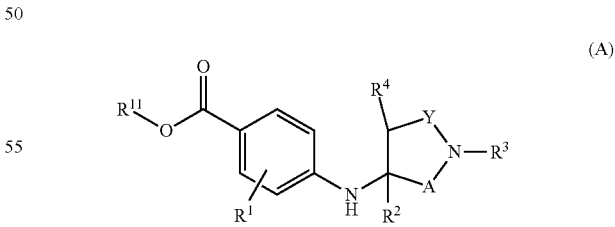

with hydroxyamine in the presence of a base; wherein $R^1$, $R^2$, $R^3$, $R^4$, A and Y have the significances given before, and $R^{11}$ is alkyl.

In one particular embodiment of the present invention the base as mentioned above can be potassium hydroxide, sodium hydroxide or the like.

In another embodiment, the invention provides a compound of formula (I) for use as medicament.

In yet another embodiment, the invention provides a pharmaceutical composition comprising a compound of formula (I) and therapeutically inert carriers or excipients.

In yet another embodiment, the present invention provides a compound of formula (I) for use in the treatment of cancer, in particular, multiple myeloma and neuroblastoma.

In yet another embodiment, the present invention provides the use of a compound of formula (I) for the preparation of medicaments useful in the treatment of cancer, in particular, neuroblastoma and/or multiple myeloma.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers (or excipients) for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-200 mg/kg, and can be taken singly or distributed over several administrations.

A compound of formula (I) when manufactured according to the above process is also an object of the invention.

Furthermore, the invention also relates to a method for the treatment of diseases that are related to HDAC 6 or HDAC 8 inhibition, which method comprises administering an effective amount of a compound of formula (I).

The invention further relates to a method for the treatment of cancer, in particular multiple myeloma, which method comprises administering an effective amount of a compound of formula (I).

Furthermore, the invention also relates to a compound of formula (I) for the preparation of medicaments useful in the treatment of diseases that are related to HDAC 6 or HDAC 8 inhibition. The invention provides a method for the treatment of diseases that are related to HDAC 6 or HDAC 8 inhibition, which method comprises administering an effective amount of a compound of formula (I).

EXAMPLES

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 min):

Acidic condition: A: 0.1% formic acid in $H_2O$; B: 0.1% formic acid in acetonitrile;

Basic condition: A: 0.01% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion (M+H)'.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

Example 1

N-Hydroxy-4-(5-oxo-1-phenyl-pyrrolidin-3-ylamino)-benzamide

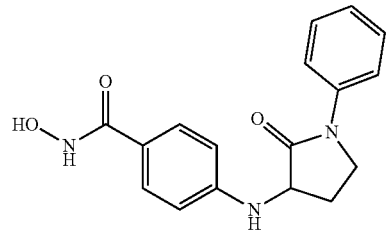 [SMILES: O=C(NO)c1ccc(NC2CCN(c3ccccc3)C2=O)cc1]

The title compound was prepared according to the general synthesis method shown in Scheme 1. A detailed synthesis route is provided as shown in Scheme 11.

Scheme 11

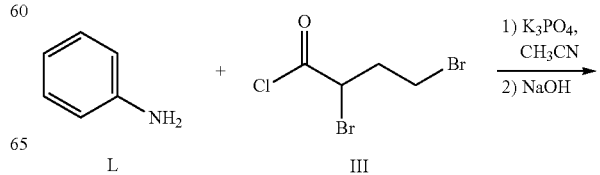

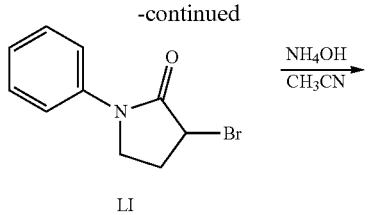

LI

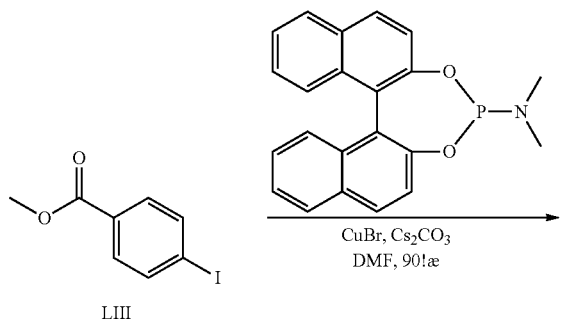

LIII

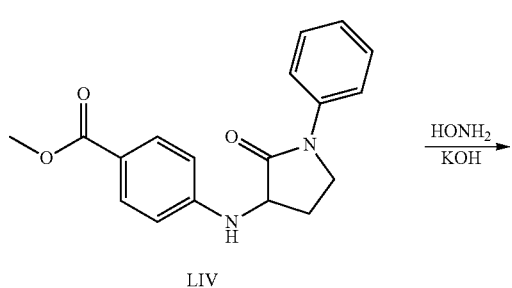

LIV 1 hr. Then NaOH (1 mL, 50% aqueous solution) was added, and the mixture was stirred overnight. After the mixture was filtered, the solid was washed with acetonitrile (10 mL), and the combined filtrate was concentrated. The residue was purified by column chromatography (eluate: EtOAc/petroleum ether from 1/5 to 1/3) to afford 3-bromo-1-phenyl-pyrrolidin-2-one LI as white solid.

To a solution of LI (1.04 g, 4.4 mmol) in acetonitrile (20 mL) was added ammonia aqueous solution (10 mL). The mixture was stirred at 40° C. overnight. After acetonitrile was removed, the remained aqueous solution was extracted with dichloromethane (20 mL twice). The organic layer was separated, dried over anhydrous sodium sulfate, and concentrated to give 4-amino-1-phenyl-pyrrolidin-2-one LII.

A mixture of LII (176 mg, 1.0 mmol), 4-iodo-benzoic acid methyl ester LIII (260 mg, 1.0 mmol), cesium carbonate (714 mg, 2.2 mmol), cuprous bromide (5.3 mg, 0.04 mmol) and (3,5-dioxa-4-phospha-cyclohepta[2,1-a;3,4-a']dinaphthalen-4-yl)-dimethyl-amine (28 mg, 0.08 mmol) in DMF (3 mL) was charged with nitrogen and heated at 100° C. overnight. Then the mixture was diluted with EtOAc (30 mL) and washed with water. The organic layer was separated, dried over anhydrous sodium sulfate and concentrated. The residue was purified by column chromatography (eluate: EtOAc/petroleum ether from 1/3 to 1/2) to afford 4-(5-oxo-1-phenyl-pyrrolidin-3-ylamino)-benzoic acid methyl ester LIV as white solid.

To a solution of LIV (235 mg, 0.76 mmol) in MeOH (2 mL) was added hydroxylamine (1 mL, 50% aqueous solution) and KOH (10 mg), and the mixture was heated at 60° C. for 3 hr. After reaction work up, the mixture was purified by preparative HPLC to afford Example 1 as white solid. MS: calc'd (MH$^+$) 312 exp (MH$^+$) 312. $^1$H NMR (DMSO-d$_6$, 400 MHz), 10.82 (s, 1H), 8.71 (s, 1H), 7.72 (d, 2H, J=8.0 Hz), 7.55 (d, 2H, J=8.4 Hz), 7.41 (t, 2H, J=7.2 Hz), 7.17 (t, 2H, J=7.2 Hz), 6.71 (d, 1H, J=8.8 Hz), 6.53 (d, 2H, J=7.2 Hz), 4.53-4.51 (m, 1H), 3.85-3.82 (m, 2H), 2.64-2.58 (m, 1H), 1.94-1.88 (m, 1H).

Example 2

4-[1-(2-Fluoro-phenyl)-2-oxo-pyrrolidin-3-ylamino]-N-hydroxy-benzamide

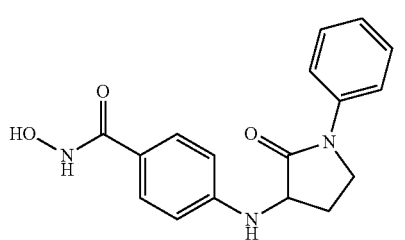

Example 1

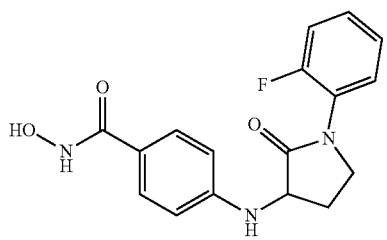 [SMILES: O=C(NO)c1ccc(NC2CCN(c3ccccc3F)C2=O)cc1]

To a suspension of phenylamine L (465 mg, 5.0 mmol) and potassium phosphate (530 mg, 2.5 mmol) in acetonitrile (20 mL) was added 2,4-dibromo-butyryl chloride III (1.32 g, 5.0 mmol) at 0° C. The mixture was brought to rt and stirred for The title compound was prepared in analogy to Example 1 in Scheme 11 by using 2-fluoro-phenylamine instead of aniline. MS: calc'd 329 (MH$^+$), exp 329 (MH$^+$). $^1$H NMR (d-DMSO, 400 MHz), 10.82 (s, 1H), 8.70 (s, 1H), 7.52-7.56 (m, 2H), 7.35-7.39 (m, 1H), 7.31-7.34 (m, 2H), 7.26-7.28 (m, 1H), 6.72 (d, 2H, J=8.8 Hz), 6.52 (d, 1H, J=6.4 Hz), 4.47-4.50 (m, 1H), 3.79-3.85 (m, 2H), 2.62-2.67 (m, 1H), 1.98-2.03 (m, 1H).

Example 3

4-[1-(3-Fluoro-phenyl)-2-oxo-pyrrolidin-3-ylamino]-N-hydroxy-benzamide

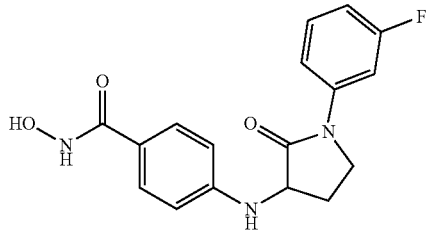 [SMILES: O=C(NO)c1ccc(NC2CCN(c3cccc(F)c3)C2=O)cc1]

The title compound was prepared in analogy to Example 1 in Scheme 11 by using 3-fluoro-phenylamine instead of aniline. MS: calc'd (MH$^+$) 330, exp (MH$^+$) 330. $^1$H NMR (d-MeOD, 400 MHz), 7.67 (d, 1H, J=8.0 Hz), 7.61 (d, 2H, J=8.8 Hz), 7.45-7.39 (m, 2H), 6.97-6.92 (m, 1H), 6.79 (d, 2H, J=8.8 Hz), 4.53 (t, 1H, J=8.4 Hz), 3.95-3.91 (m, 2H), 2.77-2.74 (m, 1H), 2.07-2.01 (m, 1H).

Example 4

4-[1-(4-Fluoro-phenyl)-2-oxo-pyrrolidin-3-ylamino]-N-hydroxy-benzamide

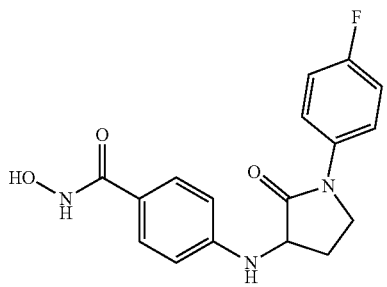 [SMILES: O=C(NO)c1ccc(NC2CCN(c3ccc(F)cc3)C2=O)cc1]

The title compound was prepared in analogy to Example 1 in Scheme 11 by using 4-fluoro-phenylamine instead of aniline. MS: calc'd 329 (MH$^+$), exp 329 (MH$^+$). $^1$H NMR (d-DMSO, 400 MHz), 10.79 (s, 1H), 8.71 (s, 1H), 7.74-7.77 (m, 2H), 7.55 (d, 2H, J=8.4 Hz), 7.24-7.29 (m, 2H), 6.71 (d, 2H, J=8.8 Hz), 7.50 (d, 1H, J=7.6 Hz), 4.50-4.53 (m, 1H), 3.82-3.84 (m, 2H), 2.57-2.64 (m, 1H), 1.87-1.97 (m, 1H).

Example 5

4-[1-(2-Chloro-phenyl)-2-oxo-pyrrolidin-3-ylamino]-N-hydroxy-benzamide

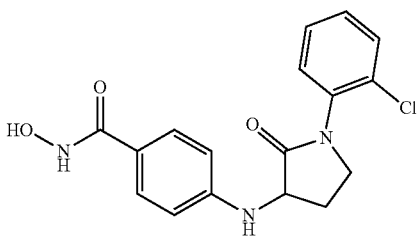 [SMILES: O=C(NO)c1ccc(NC2CCN(c3ccccc3Cl)C2=O)cc1]

The title compound was prepared in analogy to Example 1 in Scheme 11 by using 2-chloro-phenylamine instead of aniline. MS: calc'd (MH$^+$) 346, exp (MH$^+$) 346. $^1$H NMR (DMSO-d$_6$, 400 MHz), 10.82 (b, 1H), 7.62-7.60 (m, 1H), 7.55 (d, 2H, J=8.8 Hz), 7.48-7.39 (m, 3H), 6.73 (d, 2H, J=8.8 Hz), 6.51 (b, 1H), 4.55-4.48 (m, 1H), 3.87-3.66 (m, 2H), 2.68-2.64 (m, 1H), 2.07-2.01 (m, 1H).

Example 6

4-[1-(3-Chloro-phenyl)-2-oxo-pyrrolidin-3-ylamino]-N-hydroxy-benzamide

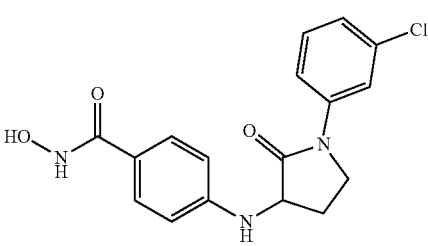 [SMILES: O=C(NO)c1ccc(NC2CCN(c3cccc(Cl)c3)C2=O)cc1]

The title compound was prepared in analogy to Example 1 in Scheme 11 by using 3-chloro-phenylamine instead of aniline. MS: calc'd (MH$^+$) 346, exp (MH$^+$) 346. $^1$H NMR (CD$_3$OD, 400 MHz), 7.91 (t, 1H, J=2.0 Hz), 7.62-7.57 (m, 3H), 7.40 (t, 1H, J=8.0 Hz), 7.23-7.21 (m, 1H), 6.79 (d, 1H, J=8.8 Hz), 4.55-4.48 (m, 1H), 3.95-3.90 (m, 2H), 2.79-2.74 (m, 1H), 2.07-2.02 (m, 1H).

Example 7

4-[1-(4-Chloro-phenyl)-2-oxo-pyrrolidin-3-ylamino]-N-hydroxy-benzamide

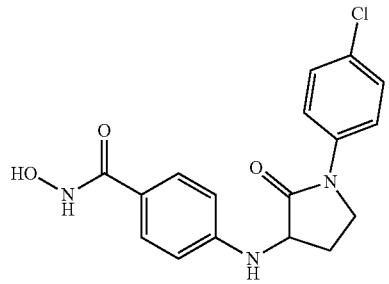

The title compound was prepared in analogy to Example 1 in Scheme 11 by using 4-chloro-phenylamine instead of aniline. MS: calc'd (MH$^+$) 346, exp (MH$^+$) 346. $^1$H NMR (DMSO-d$_6$, 400 MHz), 10.82 (b, 1H), 8.72 (b, 1H), 7.78 (d, 2H, J=8.0 Hz), 7.55 (d, 2H, J=8.8 Hz), 7.48 (d, 2H, J=8.0 Hz), 6.70 (d, 2H, J=8.8 Hz), 6.51 (d, 1H, J=7.6 Hz), 4.55-4.48 (m, 1H), 3.87-3.79 (m, 2H), 2.68-2.62 (m, 1H), 1.95-1.92 (m, 1H).

Example 8

N-Hydroxy-4-[1-(3-methoxy-phenyl)-2-oxo-pyrrolidin-3-ylamino]-benzamide

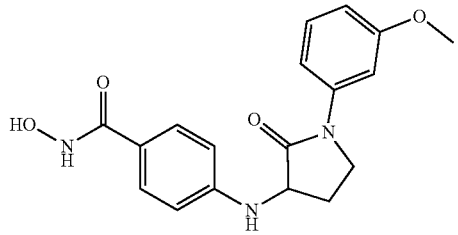 [SMILES: COc1cccc(N2CCC(Nc3ccc(C(=O)NO)cc3)C2=O)c1]

The title compound was prepared in analogy to Example 1 in Scheme 11 by using 3-methoxy-phenylamine instead of aniline. MS: calc'd (MH$^+$) 342, exp (MH$^+$) 342. $^1$H NMR (DMSO-d$_6$, 400 MHz), 10.82 (b, 1H), 8.72 (b, 1H), 7.55 (d, 2H, J=8.4 Hz), 7.42 (t, 1H, J=2.0 Hz), 7.32 (t, 1H, J=8.0 Hz), 7.23-7.20 (m, 1H), 6.77-6.75 (m, 1H), 6.70 (d, 2H, J=8.8 Hz), 6.52 (b, 1H), 4.53-4.48 (m, 1H), 3.84-3.78 (m, 2H), 3.77 (s, 3H), 2.63-2.56 (m, 1H), 1.93-1.87 (m, 1H).

Example 9

N-Hydroxy-4-[1-(3-isopropoxy-phenyl)-2-oxo-pyrrolidin-3-ylamino]-benzamide

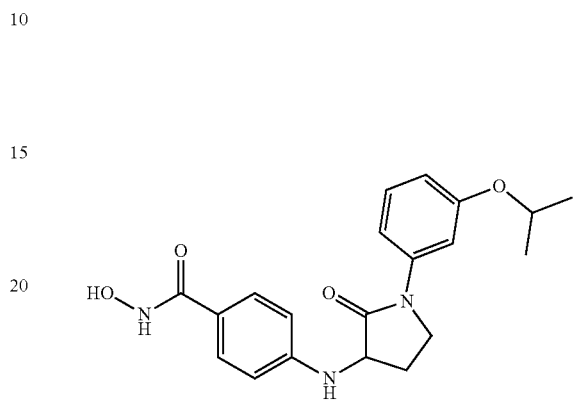

The title compound was prepared in analogy to Example 1 in Scheme 11 by using 3-isopropoxy-phenylamine instead of aniline. MS: calc'd (MH$^+$) 370 exp (MH$^+$) 370. $^1$H NMR (DMSO-d$_6$, 400 MHz), 8.70 (b, 1H), 7.55 (d, 2H, J=8.8 Hz), 7.45 (s, 1H), 7.30 (t, 1H, J=8.0 Hz), 7.17 (dd, 1H, J$_1$=8.0 Hz, J$_2$=1.6 Hz), 6.74-6.90 (m, 3H), 6.49 (d, 1H, J=7.2 Hz), 4.62-4.45 (m, 2H), 3.80 (dd, 2H, J$_1$=9.2 Hz, J$_2$=7.6 Hz), 2.61-2.57 (m, 1H), 1.94-1.88 (m, 1H), 1.27 (d, 6H, J=6.8 Hz).

Example 10

N-Hydroxy-4-[1-(4-isopropoxy-phenyl)-2-oxo-pyrrolidin-3-ylamino]-benzamide

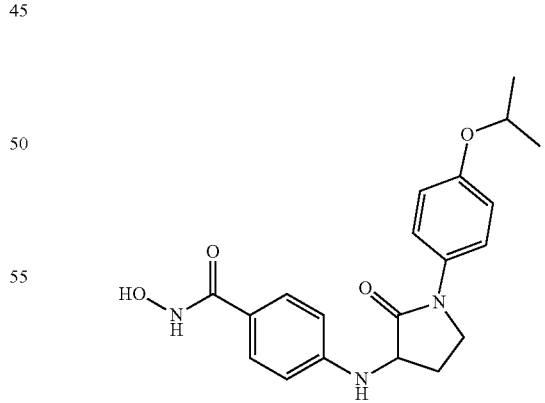

The title compound was prepared in analogy to Example 1 in Scheme 11 by using 4-isopropoxy-phenylamine instead of aniline. MS: calc'd (MH$^+$) 370 exp (MH$^+$) 370. $^1$H NMR (DMSO-d$_6$, 400 MHz), 8.70 (b, 1H), 7.57 (d, 2H, J=8.4 Hz), 7.53 (d, 2H, J=8.8 Hz), 6.95 (d, 2H, J=8.8 Hz), 6.70 (d, 2H, J=8.8 Hz), 6.49 (d, 1H, J=7.2 Hz), 4.62-1.56 (m, 1H), 4.44

(dd, 1H, J$_1$=7.8 Hz, J$_2$=2.0 Hz), 3.78 (dd, 2H, J$_1$=8.8 Hz, J$_2$=4.0 Hz), 2.61-2.57 (m, 1H), 1.92-1.87 (m, 1H), 1.26 (d, 6H, J=6. J=6.0 Hz).

Example 11

N-Hydroxy-4-[2-oxo-1-(3-trifluoromethyl-phenyl)-pyrrolidin-3-ylamino]-benzamide

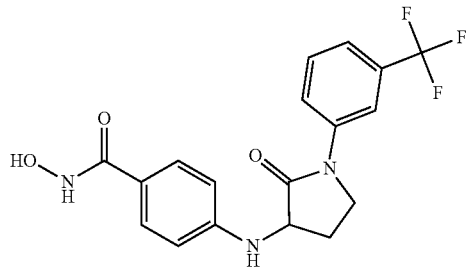 [SMILES: O=C(NO)c1ccc(NC2CCN(c3cccc(C(F)(F)F)c3)C2=O)cc1]

The title compound was prepared in analogy to Example 1 in Scheme 11 by using 3-trifluoromethyl-phenylamine instead of aniline. MS: calc'd (MH$^+$) 380, exp (MH$^+$) 380. $^1$H NMR (DMSO-d$_6$, 400 MHz), 8.25 (s, 1H), 7.88 (d, 1H, J=9.6 Hz), 7.66 (t, 1H, J=8.0 Hz), 7.57-7.51 (m, 3H), 6.71 (d, 2H, J=8.8 Hz), 6.51 (d, 1H, J=7.6 Hz), 4.58-4.52 (m, 1H), 3.95-3.84 (m, 2H), 2.65-2.59 (m, 1H), 2.1-1.91 (m, 1H).

Example 12

N-Hydroxy-4-[2-oxo-1-(4-trifluoromethyl-phenyl)-pyrrolidin-3-ylamino]-benzamide

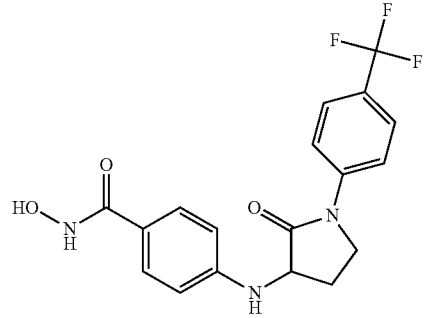 [SMILES: O=C(NO)c1ccc(NC2CCN(c3ccc(C(F)(F)F)cc3)C2=O)cc1]

The title compound was prepared in analogy to Example 1 in Scheme 11 by using 4-trifluoromethyl-phenylamine instead of aniline. MS: calc'd (MH$^+$) 380, exp (MH$^+$) 380. $^1$H NMR (CD$_3$OD, 400 MHz), 7.95 (d, 2H, J=8.8 Hz), 7.72 (d, 2H, J=8.8 Hz), 6.81 (d, 2H, J=8.8 Hz), 4.55-4.48 (m, 1H), 3.95-3.90 (m, 2H), 2.79-2.74 (m, 1H), 2.07-2.02 (m, 1H).

Example 13

N-Hydroxy-4-[1-(3-isopropyl-phenyl)-2-oxo-pyrrolidin-3-ylamino]-benzamide

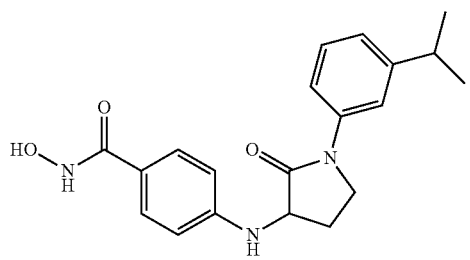 [SMILES: CC(C)c1cccc(N2CCC(Nc3ccc(C(=O)NO)cc3)C2=O)c1]

The title compound was prepared in analogy to Example 1 in Scheme 11 by using 3-isopropyl-phenylamine instead of aniline. MS: calc'd (MH$^+$) 354 exp (MH$^+$) 354. $^1$H NMR (DMSO-d$_6$, 400 MHz), 8.70 (b, 1H), 7.63 (s, 1H), 7.55 (d, 2H, J=8.8 Hz), 7.46 (dd, 1H, J$_1$=8.0 Hz, J$_2$=1.6 Hz), 7.31 (t, 1H, J=8.0 Hz), 7.05 (d, 1H, J=7.2 Hz), 6.71 (d, 2H, J=8.8 Hz), 6.49 (d, 1H, J=7.2 Hz), 4.47 (dd, 1H, J$_1$=7.8 Hz, J$_2$=2.0 Hz), 3.83 (dd, 2H, J$_1$=8.8 Hz, J$_2$=4.0 Hz), 2.91-2.86 (m, 1H), 2.61-2.59 (m, 1H), 1.94-1.88 (m, 1H), 1.22 (d, 6H, J=6.8 Hz).

Example 14

N-Hydroxy-4-[1-(4-isopropyl-phenyl)-2-oxo-pyrrolidin-3-ylamino]-benzamide

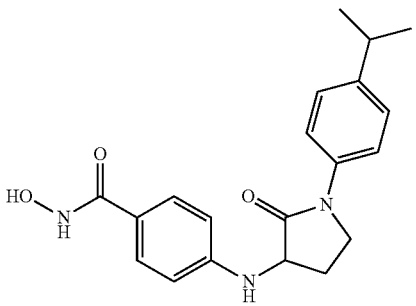 [SMILES: CC(C)c1ccc(N2CCC(Nc3ccc(C(=O)NO)cc3)C2=O)cc1]

The title compound was prepared in analogy to Example 1 in Scheme 11 by using 4-isopropyl-phenylamine instead of aniline. MS: calc'd (MH$^+$) 354 exp (MH$^+$) 354. $^1$H NMR (DMSO-d$_6$, 400 MHz), 8.70 (b, 1H), 7.60 (d, 2H, J=8.4 Hz), 7.54 (d, 2H, J=8.8 Hz), 7.26 (d, 2H, J=8.8 Hz), 6.70 (d, 2H, J=8.8 Hz), 6.49 (d, 1H, J=7.2 Hz), 4.47 (dd, 1H, J$_1$=7.8 Hz, J$_2$=2.0 Hz), 3.81 (dd, 2H, J$_1$=8.8 Hz, J$_2$=4.0 Hz), 2.90-2.83 (m, 1H), 2.51-2.49 (m, 1H), 1.93-1.89 (m, 1H), 1.20 (d, 6H, J=7.2 Hz).

Example 15

4-[1-(4-Butyl-phenyl)-2-oxo-pyrrolidin-3-ylamino]-N-hydroxy-benzamide

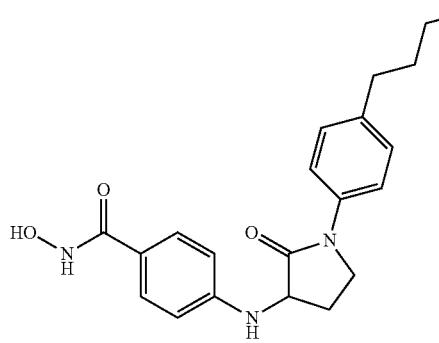

The title compound was prepared in analogy to Example 1 in Scheme 11 by using 4-butyl-phenylamine instead of aniline. MS: calc'd (MH$^+$) 368 exp (MH$^+$) 368. $^1$H NMR (DMSO-d$_6$, 400 MHz), 8.70 (b, 1H), 7.60 (d, 2H, J=8.4 Hz), 7.54 (d, 2H, J=8.8 Hz), 7.21 (d, 2H, J=8.8 Hz), 6.70 (d, 2H, J=8.8 Hz), 6.49 (d, 1H, J=7.2 Hz), 4.47 (dd, 1H, J$_1$=7.8 Hz, J$_2$=2.0 Hz), 3.81 (dd, 2H, J$_1$=8.8 Hz, J$_2$=4.0 Hz), 2.61-2.54 (m, 3H), 1.93-1.87 (m, 1H), 1.57-1.50 (m, 2H), 1.32-1.26 (m, 2H), 0.89 (t, 3H, J=7.2 Hz).

Example 16

4-[1-(4-tert-Butyl-phenyl)-2-oxo-pyrrolidin-3-ylamino]-N-hydroxy-benzamide

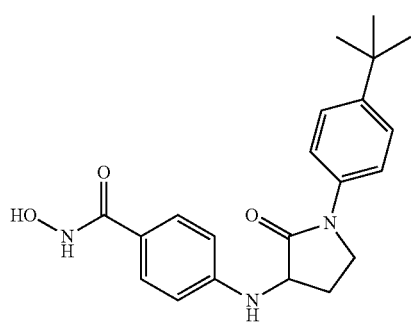 [SMILES: CC(C)(C)c1ccc(N2CCC(Nc3ccc(C(=O)NO)cc3)C2=O)cc1]

The title compound was prepared in analogy to Example 1 in Scheme 11 by using 4-tert-butyl-phenylamine instead of aniline. MS: calc'd (MH$^+$) 368 exp (MH$^+$) 368. $^1$H NMR (DMSO-d$_6$, 400 MHz), 8.70 (b, 1H), 7.61 (d, 2H, J=8.4 Hz), 7.54 (d, 2H, J=8.8 Hz), 7.41 (d, 2H, J=8.8 Hz), 6.70 (d, 2H, J=8.8 Hz), 6.49 (d, 1H, J=7.2 Hz), 4.47 (dd, 1H, J$_1$=7.8 Hz, J$_2$=2.0 Hz), 3.81 (dd, 2H, J$_1$=8.8 Hz, J$_2$=4.0 Hz), 2.51-2.49 (m, 1H), 1.93-1.89 (m, 1H), 1.27 (s, 9H).

Example 17

N-Hydroxy-4-[1-(4-methanesulfonyl-phenyl)-2-oxo-pyrrolidin-3-ylamino]-benzamide

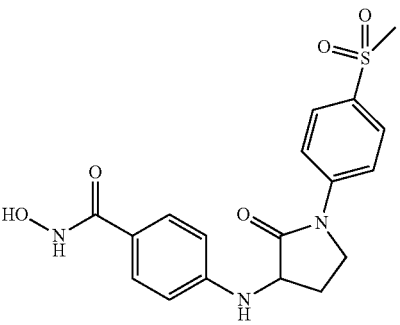 [SMILES: CS(=O)(=O)c1ccc(N2CCC(Nc3ccc(C(=O)NO)cc3)C2=O)cc1]

The title compound was prepared in analogy to Example 1 in Scheme 11 by using 4-methanesulfonylphenylamine instead of aniline. MS: calc'd (MH+) 390, exp (MH+) 390. $^1$H NMR (CD$_3$OD, 400 MHz), 8.74 (d, 2H, J=9.2 Hz), 8.69 (d, 2H, J=9.2 Hz), 8.32 (d, 2H, J=8.4 Hz), 7.50 (d, 2H, J=8.4 Hz), 4.68 (m, 2H), 4.04 (m, 1H), 3.46 (m, 1H), 2.79 (m, 1H)

Example 18

4-[1-(3-Cyano-phenyl)-2-oxo-pyrrolidin-3-ylamino]-N-hydroxy-benzamide

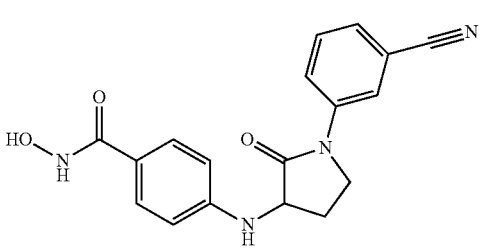 [SMILES: N#Cc1cccc(N2CCC(Nc3ccc(C(=O)NO)cc3)C2=O)c1]

The title compound was prepared in analogy to Example 1 in Scheme 11 by using 3-cyanophenylamine instead of aniline. MS: calc'd (MH+) 337, exp (MH+) 337. $^1$H NMR (CD$_3$OD, 400 MHz), 8.09 (s, 1H), 7.60 (d, 1H, J=8.8 Hz), 8.21 (s, 1H), 8.00 (d, 1H, J=8.0 Hz), 7.61 (d, 2H, J=8.4 Hz), 7.56 (t, 2H, J=7.6 Hz), 6.80 (d, 2H, J=8.8 Hz), 4.52 (t, 1H, J=8.4 Hz), 3.87-4.00 (m, 2H), 2.76 (m, 1H), 2.06 (m, 1H)

Example 19

4-[1-(4-Cyano-phenyl)-2-oxo-pyrrolidin-3-ylamino]-N-hydroxy-benzamide

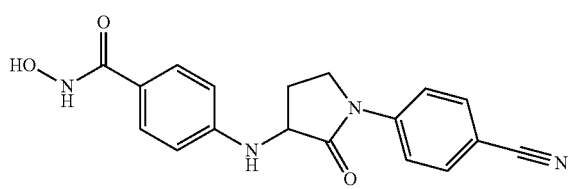 [SMILES: N#Cc1ccc(N2CCC(Nc3ccc(C(=O)NO)cc3)C2=O)cc1]

The title compound was prepared in analogy to Example 1 in Scheme 11 by using 4-cyanophenylamine instead of aniline. MS: calc'd (MH+) 337, exp (MH+) 337. $^1$H NMR (CD$_3$OD, 400 MHz), 7.96 (d, 2H, J=9.2 Hz), 7.78 (d, 2H, J=8.8 Hz), 7.60 (d, 2H, J=8.8 Hz), 6.79 (d, 2H, J=8.8 Hz), 4.52 (t, 1H, J=8.4 Hz), 3.87-4.00 (m, 2H), 2.76 (m, 1H), 2.06 (m, 1H)

Example 20

4-[1-(3-Chloro-4-fluoro-phenyl)-2-oxo-pyrrolidin-3-ylamino]-N-hydroxy-benzamide

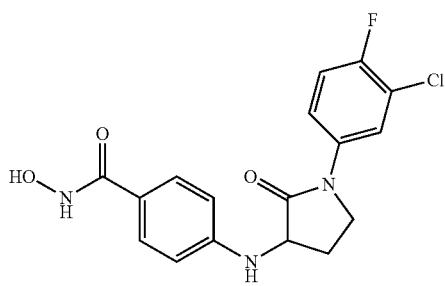 [SMILES: O=C(NO)c1ccc(NC2CCN(c3ccc(F)c(Cl)c3)C2=O)cc1]

The title compound was prepared in analogy to Example 1 in Scheme 11 by using 3-chloro-4-fluorophenylamine instead of aniline. MS: calc'd (MH$^+$) 364, exp (MH$^+$) 364. $^1$H NMR (d-MeOD, 400 MHz), 8.00-7.98 (m, 1H), 7.63-7.59 (m, 3H), 7.30 (t, 1H, J=8.8 Hz), 6.79 (d, 2H, J=8.8 Hz), 4.53 (t, 1H, J=8.4 Hz), 3.92-3.89 (m, 2H), 2.77-2.74 (m, 1H), 2.07-2.02 (m, 1H).

Example 21

4-[1-(3-Chloro-5-fluoro-phenyl)-2-oxo-pyrrolidin-3-ylamino]-N-hydroxy-benzamide

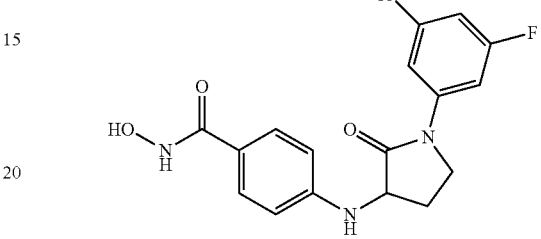

The title compound was prepared in analogy to Example 1 in Scheme 11 by using 3-chloro-5-fluorophenylamine instead of aniline. MS: calc'd (MH$^+$) 364, exp (MH$^+$) 364. $^1$H NMR (d-MeOD, 400 MHz), 7.59-7.56 (m, 3H), 7.40-7.36 (m, 1H), 7.27 (t, 1H, J=8.8 Hz), 4.54 (t, 1H, J=8.4 Hz), 3.95-3.91 (m, 1H), 3.85-3.80 (m, 1H), 2.78-2.75 (m, 1H), 2.17-2.12 (m, 1H).

Example 22

4-[1-(5-Chloro-2-fluoro-phenyl)-2-oxo-pyrrolidin-3-ylamino]-N-hydroxy-benzamide

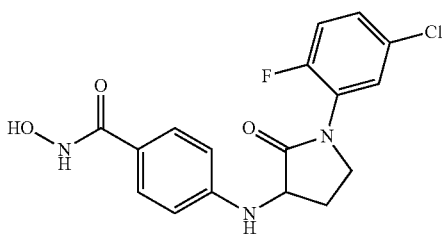 [SMILES: O=C(NO)c1ccc(NC2CCN(c3cc(Cl)ccc3F)C2=O)cc1]

The title compound was prepared in analogy to Example 1 in Scheme 11 by using 3-chloro-6-fluorophenylamine instead of aniline. MS: calc'd (MH$^+$) 364, exp (MH$^+$) 364. $^1$H NMR (d-MeOD, 400 MHz), 7.66-7.57 (m, 4H), 7.06-7.03 (m, 1H), 6.79 (d, 2H, J=8.8 Hz), 4.55 (t, 1H, J=8.4 Hz), 3.93-3.89 (m, 2H), 2.77-2.74 (m, 1H), 2.07-2.01 (m, 1H).

Example 23

4-[1-(2,4-Dichloro-phenyl)-2-oxo-pyrrolidin-3-ylamino]-N-hydroxy-benzamide

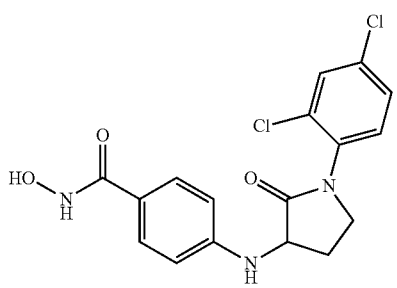 [SMILES: O=C(NO)c1ccc(NC2CCN(c3ccc(Cl)cc3Cl)C2=O)cc1]

The title compound was prepared in analogy to Example 1 in Scheme 11 by using 2,4-dichlorophenylamine instead of aniline MS: calc'd 379 (MH⁺), exp 379 (MH⁺). ¹H NMR (d-DMSO, 400 MHz), 8.69 (s, 1H), 7.80 (d, 1H, J=2.4 Hz), 7.47-7.56 (m, 4H), 6.72 (d, 2H, J=8.8 Hz), 6.51 (d, 1H, J=7.2 Hz), 4.42-4.48 (m, 1H), 3.69-3.76 (m, 2H), 2.64-2.68 (m, 1H), 2.02-2.04 (m, 1H).

Example 24

4-[1-(2,3-Dichloro-phenyl)-2-oxo-pyrrolidin-3-ylamino]-N-hydroxy-benzamide

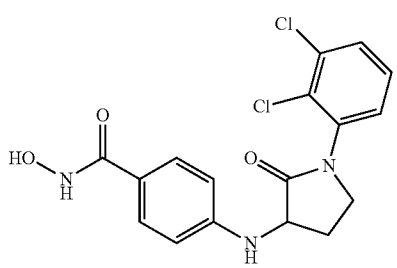 [SMILES: O=C(NO)c1ccc(NC2CCN(c3cccc(Cl)c3Cl)C2=O)cc1]

The title compound was prepared in analogy to Example 1 in Scheme 11 by using 2,3-dichlorophenylamine instead of aniline. MS: calc'd 379 (MH⁺), exp 379 (MH⁺). ¹H NMR (d-DMSO, 400 MHz), 10.81 (s, 1H), 8.69 (s, 1H), 7.68-7.70 (dd, 1H, J=4.4 Hz, J=4.8 Hz), 7.49 (m, 4H), 6.73 (d, 2H, J=10 Hz), 6.53 (d, 1H, J=7.2 Hz), 4.46-4.48 (m, 1H), 3.69-3.75 (m, 2H), 2.64-2.66 (m, 1H), 2.05-2.08 (m, 1H).

Example 25

4-[1-(3,4-Dichloro-phenyl)-2-oxo-pyrrolidin-3-ylamino]-N-hydroxy-benzamide

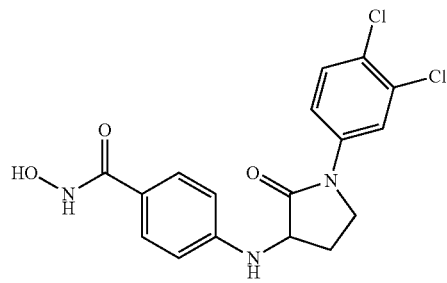

The title compound was prepared in analogy to Example 1 in Scheme 11 by using 3,4-dichlorophenylamine instead of aniline. MS: calc'd (MH⁺) 380, exp (MH⁺) 380. ¹H NMR (CD₃OD, 400 MHz), 8.08 (d, 2H, J=2.4 Hz), 7.65-7.55 (m, 2H), 6.79 (d, 2H, J=8.8 Hz), 4.55-4.52 (m, 1H), 3.95-3.90 (m, 2H), 2.79-2.74 (m, 1H), 2.07-2.02 (m, 1H).

Example 26

4-[1-(3,5-Dichloro-phenyl)-2-oxo-pyrrolidin-3-ylamino]-N-hydroxy-benzamide

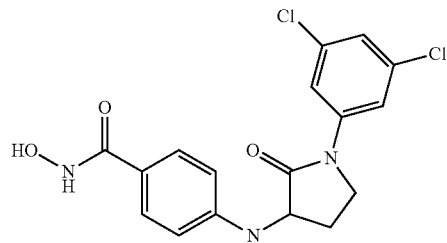

The title compound was prepared in analogy to Example 1 in Scheme 11 by using 3,5-dichlorophenylamine instead of aniline. MS: calc'd (MH⁺) 380, exp (MH⁺) 380. ¹H NMR (DMSO-d₆, 400 MHz), 7.83 (d, 2H, J=2.0 Hz), 7.55 (d, 2H, J=8.8 Hz), 7.41 (t, 1H, J=2.0 Hz), 6.70 (d, 2H, J=8.8 Hz), 6.50

(d, 1H, J=7.6 Hz), 4.58-4.52 (m, 1H), 3.95-3.80 (m, 2H), 2.52-2.50 (m, 1H), 2.1-1.91 (m, 1H).

Example 27

4-[1-(2,6-Dichloro-phenyl)-2-oxo-pyrrolidin-3-ylamino]-N-hydroxy-benzamide

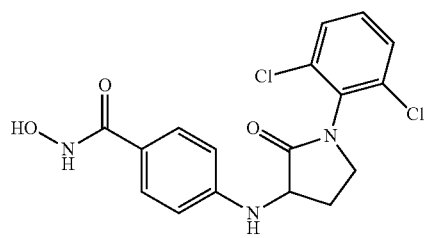 [SMILES: O=C(NO)c1ccc(NC2CCN(c3c(Cl)cccc3Cl)C2=O)cc1]

The title compound was prepared in analogy to Example 1 in Scheme 11 by using 2,6-dichlorophenylamine instead of aniline. MS: calc'd 379 (MH⁺), exp 379 (MH⁺). $^1$H NMR (d-DMSO, 400 MHz), 10.82 (s, 1H), 7.63-7.67 (m, 2H), 7.51-7.56 (m, 2H), 7.50-7.51 (m, 1H,) 6.75 (d, 2H, J=8.8 Hz), 4.44-4.49 (m, 1H), 3.59-3.68 (m, 1H), 3.70-3.74 (m, 1H), 2.50-2.55 (m, 1H), 2.05-2.15 (m, 1H).

Example 28

4-[1-(4-Fluoro-2,6-dimethyl-phenyl)-2-oxo-pyrrolidin-3-ylamino]-N-hydroxy-benzamide

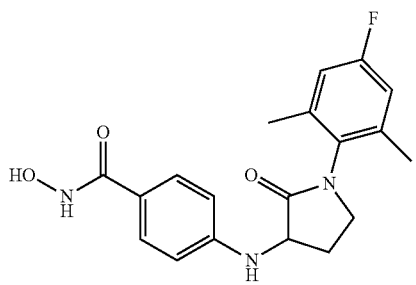 [SMILES: Cc1cc(F)cc(C)c1N1CCC(Nc2ccc(C(=O)NO)cc2)C1=O]

The title compound was prepared in analogy to Example 1 in Scheme 11 by using 4-fluoro-2,6-dimethyl-phenylamine instead of aniline. MS: calc'd (MH⁺) 358, exp (MH⁺) 358. $^1$H NMR (DMSO-d$_6$, 400 MHz), 10.82 (b, 1H), 8.72 (b, 1H), 7.55 (d, 2H, J=8.4 Hz), 7.27 (s, 1H), 7.14 (s, 1H), 6.74 (d, 2H, J=8.8 Hz), 6.52 (b, 1H), 4.53-4.48 (m, 1H), 3.62-3.45 (m, 2H), 2.69-2.66 (m, 1H), 2.19 (s, 3H), 2.16 (s, 3H), 2.04-1.98 (m, 1H).

Example 29

4-[1-(4-Chloro-3-hydroxymethyl-phenyl)-2-oxo-pyrrolidin-3-ylamino]-N-hydroxy-benzamide

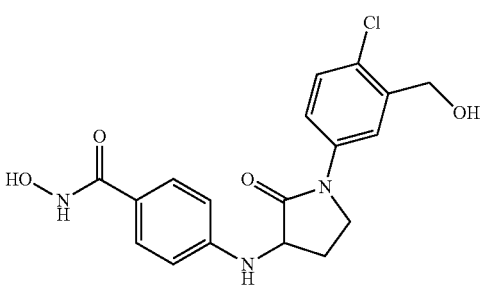 [SMILES: O=C(NO)c1ccc(NC2CCN(c3ccc(Cl)c(CO)c3)C2=O)cc1]

The title compound was prepared in analogy to Example 1 in Scheme 11 by using (5-amino-2-chloro-phenyl)-methanol instead of aniline. MS: calc'd (MH⁺) 358, exp (MH⁺) 358. $^1$H NMR (DMSO-d$_6$, 400 MHz), 8.70 (s, 1H), 7.88 (s, 1H), 7.64 (d, 1H, J=8.8 Hz), 7.55 (d, 2H, J=8.4 Hz), 7.42 (d, 1H, J=8.8 Hz), 6.70 (d, 2H, J=8.8 Hz), 6.49 (d, 1H, J=8.0 Hz), 5.46 (t, 1H, J=5.6 Hz), 4.57-4.47 (m, 3H), 3.85-3.82 (m, 2H), 2.68-2.58 (m, 1H), 1.98-1.88 (m, 1H).

Example 30

N-Hydroxy-4-[2-oxo-1-(3-phenoxy-phenyl)-pyrrolidin-3-ylamino]-benzamide

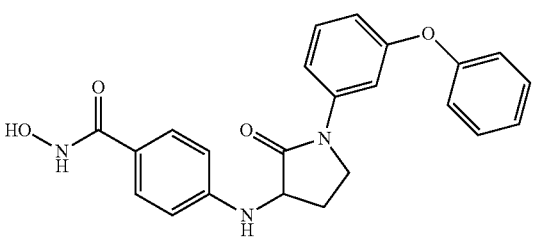 [SMILES: O=C(NO)c1ccc(NC2CCN(c3cccc(Oc4ccccc4)c3)C2=O)cc1]

The title compound was prepared in analogy to Example 1 in Scheme 11 by using 3-phenoxy-phenylamine instead of aniline. MS: calc'd (MH+) 404, exp (MH+) 404. $^1$H NMR (CD$_3$OD, 400 MHz), 7.60 (d, 2H, J=8.8 Hz), 7.51 (m, 1H), 7.39 (m, 4H), 7.13 (t, 1H, J=7.6 Hz), 7.02 (d, 2H, J=8.8 Hz), 6.83 (m, 1H), 6.77 (d, 2H, J=8.8 Hz), 4.52 (t, 1H, J=8.4 Hz), 3.87-4.00 (m, 2H), 2.76 (m, 1H), 2.06 (m, 1H)

Example 31

N-Hydroxy-4-[2-oxo-1-(4-phenoxy-phenyl)-pyrrolidin-3-ylamino]-benzamide

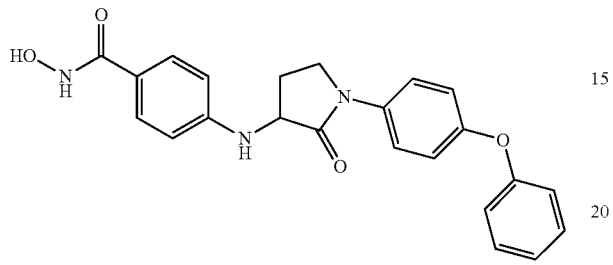

The title compound was prepared in analogy to Example 1 in Scheme 11 by using 4-phenoxy-phenylamine instead of aniline. MS: calc'd (MH+) 404, exp (MH+) 404. $^1$H NMR (CD$_3$OD, 400 MHz), 7.67 (d, 2H, J=10 Hz), 7.61 (d, 2H, J=9.6 Hz), 7.38 (m, 2H), 7.13 (t, 1H, J=7.6 Hz), 7.05 (d, 2H, J=9.2 Hz), 7.00 (d, 2H, J=8.8 Hz), 6.80 (d, 2H, J=9.2 Hz), 4.52 (t, 1H, J=8.4 Hz), 3.87-4.00 (m, 2H), 2.76 (m, 1H), 2.06 (m, 1H).

Example 32

4-(1-Biphenyl-3-yl-2-oxo-pyrrolidin-3-ylamino)-N-hydroxy-benzamide

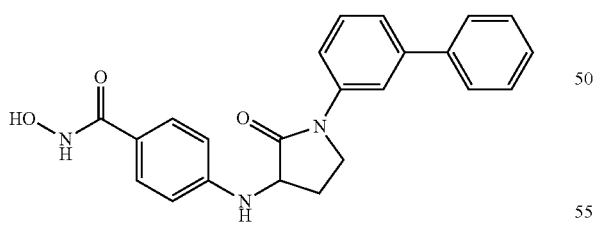

The title compound was prepared in analogy to Example 1 in Scheme 11 by using biphenyl-3-ylamine instead of aniline. MS: calc'd (MH+) 388, exp (MH+) 388. $^1$H NMR (CD$_3$OD, 400 MHz), 8.0 (m, 1H), 7.65 (m, 5H), 7.48 (m, 4H), 7.36 (m, 1H), 6.82 (d, 2H, J=9.6 Hz), 4.58 (t, 1H, J=8.4 Hz), 4.00 (m, 2H), 2.81 (m, 1H), 2.09 (m, 1H).

Example 33

N-Hydroxy-4-[2-oxo-1-(3-pyrrol-1-yl-phenyl)-pyrrolidin-3-ylamino]-benzamide

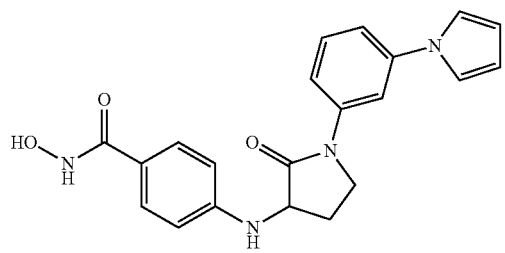 [SMILES: O=C(NO)c1ccc(NC2CCN(c3cccc(-n4cccc4)c3)C2=O)cc1]

The title compound was prepared in analogy to Example 1 in Scheme 11 by using 3-pyrrol-1-yl-phenylamine instead of aniline. MS: calc'd (MH+) 377, exp (MH+) 377. $^1$H NMR (CD$_3$OD, 400 MHz), 7.97 (m, 1H), 7.62 (d, 2H, J=7.6 Hz), 7.49 (m, 2H), 7.35 (m, 1H), 7.22 (m, 2H), 6.80 (d, 2H, J=8.8 Hz), 6.31 (m, 2H), 4.58 (t, 1H, J=8.4 Hz), 4.00 (m, 2H), 2.81 (m, 1H), 2.09 (m, 1H)

Example 34

N-Hydroxy-4-[1-(4-imidazol-1-yl-phenyl)-2-oxo-pyrrolidin-3-ylamino]-benzamide

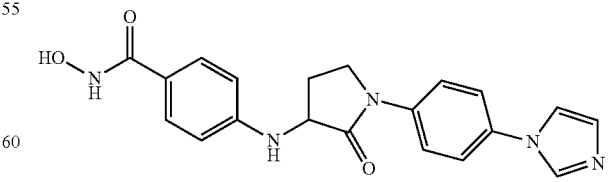

The title compound was prepared in analogy to Example 1 in Scheme 11 by using 3-imidazol-1-yl-phenylamine instead of aniline. MS: calc'd (MH+) 378, exp (MH+) 378. $^1$H NMR (CD$_3$OD, 400 MHz), 9.26 (s, 1H), 8.02 (m, 3H), 7.80 (d, 2H, J=8.8 Hz), 7.70 (s, 1H), 7.61 (d, 2H, J=8.8 Hz), 6.82 (d, 2H, J=9.6 Hz), 4.58 (t, 1H, J=8.4 Hz), 4.00 (m, 2H), 2.81 (m, 1H), 2.09 (m, 1H).

Example 35

N-Hydroxy-4-[1-(3-oxazol-5-yl-phenyl)-2-oxo-pyrrolidin-3-ylamino]-benzamide

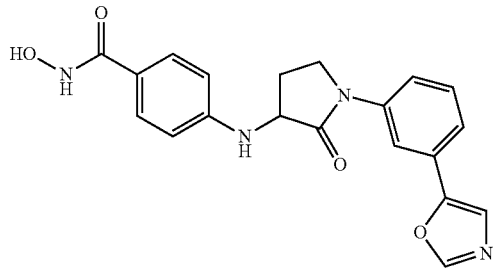 [SMILES: O=C(NO)c1ccc(NC2CCN(c3cccc(-c4cnco4)c3)C2=O)cc1]

The title compound was prepared in analogy to Example 1 in Scheme 11 by using 3-oxazol-5-yl-phenylamine instead of aniline. MS: calc'd (MH+) 346, exp (MH+) 346. $^1$H NMR (CD$_3$OD, 400 MHz), 8.33 (s, 1H), 8.17 (m, 1H), 7.51-7.71 (m, 6H), 6.82 (d, 2H, J=8.8 Hz), 4.58 (t, 1H, J=8.4 Hz), 4.00 (m, 2H), 2.81 (m, 1H), 2.09 (m, 1H).

Example 36

4-{1-[3-(2-Dimethylamino-ethoxy)-phenyl]-2-oxo-pyrrolidin-3-ylamino}-N-hydroxy-benzamide

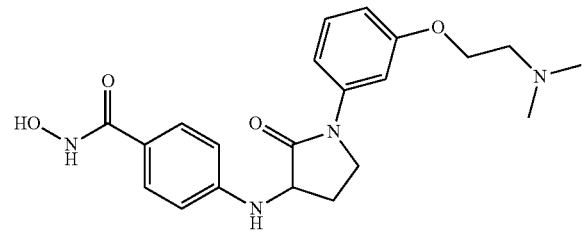 [SMILES: CN(C)CCOc1cccc(N2CCC(Nc3ccc(C(=O)NO)cc3)C2=O)c1]

The title compound was prepared in analogy to Example 1 in Scheme 11 by using 3-(2-dimethylamino-ethoxy)-phenylamine instead of aniline. MS: calc'd (MH+) 399, exp (MH+) 399. $^1$H NMR (CD$_3$OD, 400 MHz), 7.61 (d, 2H, J=8.0 Hz), 7.49 (s, 1H), 7.34 (t, 1H, J=8.0 Hz), 7.19 (d, 1H, J=8.0 Hz), 6.85 (d, 1H, J=8.0 Hz), 6.80 (d, 2H, J=8.0 Hz), 4.52 (t, 1H, J=8.4 Hz), 3.96 (t, 2H, J=5.6 Hz), 3.94-3.90 (m, 2H), 2.98-2.95 (m, 2H), 2.77-2.73 (m, 1H), 2.23 (s, 6H), 2.07-2.02 (m, 1H).

Example 37

N-Hydroxy-4-(1-naphthalen-1-yl-2-oxo-pyrrolidin-3-ylamino)-benzamide

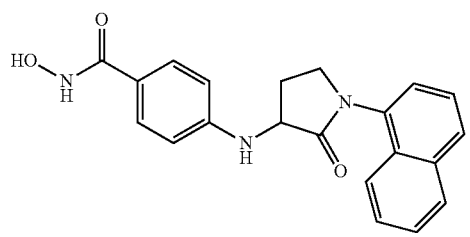 [SMILES: O=C(NO)c1ccc(NC2CCN(c3cccc4ccccc34)C2=O)cc1]

The title compound was prepared in analogy to Example 1 in Scheme 11 by using naphthalen-1-ylamine instead of aniline. MS: calc'd (MH+) 362, exp (MH+) 362. $^1$H NMR (CD$_3$OD, 400 MHz), 7.88-8.00 (m, 3H), 7.56-7.64 (m, 4H), 7.51 (d, 1H, J=6.8 Hz), 6.86 (d, 2H, J=8.8 Hz), 4.52 (t, 1H, J=8.4 Hz), 4.05 (m, 1H), 3.87 (m, 1H), 2.76 (m, 1H), 2.06 (m, 1H).

Example 38

N-Hydroxy-4-(1-naphthalen-2-yl-2-oxo-pyrrolidin-3-ylamino)-benzamide

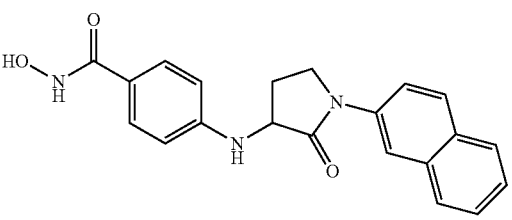 [SMILES: O=C(NO)c1ccc(NC2CCN(c3ccc4ccccc4c3)C2=O)cc1]

The title compound was prepared in analogy to Example 1 in Scheme 11 by using naphthalen-2-ylamine instead of aniline. MS: calc'd (MH+) 362, exp (MH+) 362. $^1$H NMR (CD$_3$OD, 400 MHz), 8.09 (s, 1H), 7.60 (d, 2H, J=8.8 Hz), 7.96 (m, 3H), 7.67 (d, 2H, J=8.4 Hz), 7.55 (m, 2H), 6.87 (d, 2H, J=8.4 Hz), 4.52 (t, 1H, J=8.4 Hz), 3.87-4.00 (m, 2H), 2.76 (m, 1H), 2.06 (m, 1H)

Example 39

N-Hydroxy-4-(2-oxo-1-quinolin-8-yl-pyrrolidin-3-ylamino)-benzamide

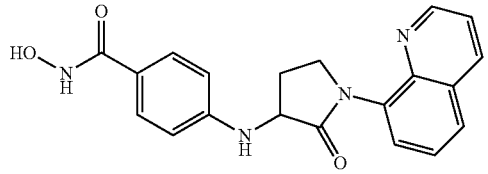 [SMILES: O=C(NO)c1ccc(NC2CCN(c3cccc4cccnc34)C2=O)cc1]

The title compound was prepared in analogy to Example 1 in Scheme 11 by using quinolin-8-ylamine instead of aniline. MS: calc'd (MH+) 363, exp (MH+) 363. $^1$H NMR (CD$_3$OD, 400 MHz), 8.96 (s, 1H), 8.45 (d, 1H, J=8.0 Hz), 8.02 (d, 1H, J=8.0 Hz), 7.80 (d, 1H, J=7.2 Hz), 7.70 (t, 1H, J=8.0 Hz), 7.64-7.61 (m, 3H), 6.86 (d, 2H, J=8.4 Hz), 4.73 (t, 1H, J=8.4 Hz), 4.14 (q, 1H, J=8.4 Hz), 3.99 (t, 1H, J=8.8 Hz), 2.88-2.84 (m, 1H), 2.34-2.29 (m, 1H).

Example 40

N-Hydroxy-4-(2-oxo-1-quinolin-5-yl-pyrrolidin-3-ylamino)-benzamide

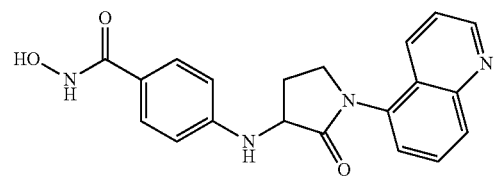 [SMILES: O=C(NO)c1ccc(NC2CCN(c3cccc4ncccc34)C2=O)cc1]

The title compound was prepared in analogy to Example 1 in Scheme 11 by using quinolin-5-ylamine instead of aniline. MS: calc'd (MH+) 363, exp (MH+) 363. $^1$H NMR (CD$_3$OD, 400 MHz), 8.83 (dd, 1H, J=4.4 Hz, 1.6 Hz), 8.40-8.33 (m, 2H), 8.17 (s, 1H), 8.07 (d, 1H, J=9.6 Hz), 7.62 (dt, 2H, J=8.8 Hz, 2.4 Hz), 7.58-7.55 (m, 1H), 6.83 (dt, 2H, J=9.6 Hz, 4.0 Hz), 4.60 (t, 1H, J=8.0 Hz), 4.12-4.07 (m, 2H), 2.84-2.81 (m, 1H), 2.15-2.10 (m, 1H).

Example 41

4-(1-Cyclohexyl-2-oxo-pyrrolidin-3-ylamino)-N-hydroxy-benzamide

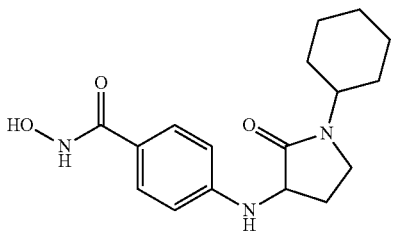 [SMILES: O=C(NO)c1ccc(NC2CCN(C3CCCCC3)C2=O)cc1]

The title compound was prepared in analogy to Example 1 in Scheme 11 by using cyclohexylamine instead of aniline. MS: calc'd (MH$^+$) 318 exp (MH$^+$) 318. $^1$H NMR (DMSO-d$_6$, 400 MHz), 8.70 (b, 1H), 7.52 (d, 2H, J=8.8 Hz), 6.65 (d, 2H, J=8.8 Hz), 6.49 (d, 1H, J=7.2 Hz), 4.16 (dd, 1H, J$_1$=16.4 Hz, J$_2$=8.4 Hz), 3.78-3.72 (m, 1H), 3.28-3.21 (m, 1H), 1.78-1.05 (m, 12H).

Example 42

4-(1-Benzyl-5-oxo-pyrrolidin-3-ylamino)-N-hydroxy-benzamide

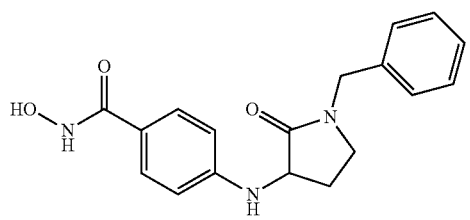 [SMILES: O=C(NO)c1ccc(NC2CCN(Cc3ccccc3)C2=O)cc1]

The title compound was prepared in analogy to Example 1 in Scheme 11 by using benzylamine instead of aniline. MS: calc'd (MH$^+$) 326 exp (MH$^+$) 326. $^1$H NMR (d-MeOD, 400 MHz), 7.59 (d, 2H, J=8.4 Hz), 7.40-7.30 (m, 5H), 6.76 (d, 2H, J=8.4 Hz), 4.58-4.49 (m, 2H), 4.38 (t, 1H, J=8.8 Hz), 3.37-3.33 (m, 2H), 2.61-2.57 (m, 1H), 1.90-1.84 (m, 1H).

Example 43

N-Hydroxy-4-(2-oxo-1-phenethyl-pyrrolidin-3-ylamino)-benzamide

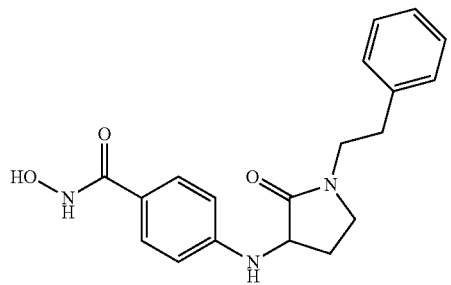 [SMILES: O=C(NO)c1ccc(NC2CCN(CCc3ccccc3)C2=O)cc1]

The title compound was prepared in analogy to Example 1 in Scheme 11 by using phenethylamine instead of aniline. MS: calc'd (MH$^+$) 340, exp (MH$^+$) 340. $^1$H NMR (d-MeOD, 400 MHz), 7.57 (d, 2H, J=8.8 Hz), 7.34-7.22 (m, 5H), 6.70 (d, 2H, J=8.8 Hz), 4.20 (d, 1H, J=8.8 Hz), 3.57 (d, 2H, J=7.6 Hz), 3.36-3.33 (m, 2H), 2.90 (d, 2H, J=7.2 Hz), 2.56-2.52 (m, 1H), 1.85-1.79 (m, 1H).

Example 44/45

N-Hydroxy-4-[5-oxo-1-(R-1-phenyl-ethyl)-pyrrolidin-3-ylamino]-benzamide

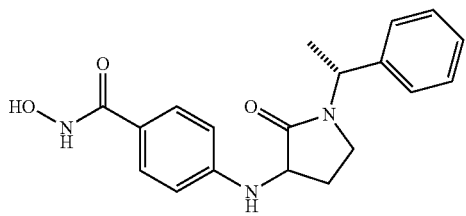 [SMILES: C[C@H](c1ccccc1)N1CCC(Nc2ccc(C(=O)NO)cc2)C1=O]

The title compound was prepared in analogy to Example 1 in Scheme 11 by using R-1-phenyl ethylamine instead of aniline. MS: calc'd (MH$^+$) 340, exp (MH$^+$) 340. $^1$H NMR (d-MeOD, 400 MHz), 7.60-7.57 (m, 2H), 7.41-7.30 (m, 5H), 6.75-6.72 (m, 2H), 5.44-5.41 (m, 1H), 4.91-4.27 (m, 1H), 3.51-3.32 (m, 1H), 3.12-3.01 (m, 1H), 2.58-2.53 (m, 1H), 1.88-1.83 (m, 1H), 1.60 (d, 3H, J=7.2 Hz).

Example 46

N-Hydroxy-4-[1-(4-methoxy-benzyl)-2-oxo-pyrrolidin-3-ylamino]-benzamide

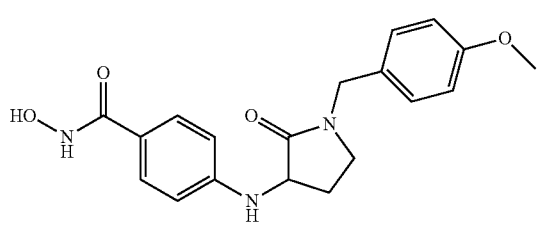 [SMILES: COc1ccc(CN2CCC(Nc3ccc(C(=O)NO)cc3)C2=O)cc1]

The title compound was prepared in analogy to Example 1 in Scheme 11 by using 4-methoxy-phenylamine instead of aniline. MS: calc'd (MH$^+$) 356, exp (MH$^+$) 356. $^1$H NMR (d-MeOD, 400 MHz), 7.58 (d, 2H, J=6.8 Hz), 7.23 (d, 2H, J=6.8 Hz), 6.93 (d, 2H, J=8.8 Hz), 6.73 (d, 2H, J=8.8 Hz), 4.51-4.33 (m, 3H), 3.80 (s, 3H), 3.34-3.31 (m, 2H), 2.59-2.56 (m, 1H), 1.87-1.82 (m, 1H).

Example 47

N-Hydroxy-4-[1-(1-methyl-1-phenyl-ethyl)-2-oxo-pyrrolidin-3-ylamino]-benzamide

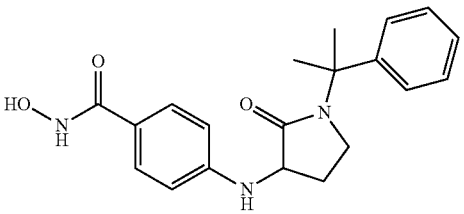 [SMILES: CC(C)(c1ccccc1)N1CCC(Nc2ccc(C(=O)NO)cc2)C1=O]

The title compound was prepared in analogy to Example 1 in Scheme 11 by using 1-methyl-1-phenyl-ethylamine instead of aniline. MS: calc'd (MH$^+$) 353, exp (MH$^+$) 353. $^1$H NMR (d-MeOD, 400 MHz), 7.56 (d, 2H, J=8.0 Hz), 7.40-7.32 (m, 4H), 7.24 (t, 1H, J=8.0 Hz), 6.71 (d, 2H, J=8.8 Hz), 4.25 (t, 1H, J=8.4 Hz), 3.62-3.58 (m, 2H), 2.64-2.61 (m, 1H), 1.91-1.85 (m, 1H), 1.77 (s, 6H).

Example 48

4-{1-[1-(2-Chloro-phenyl)-1-methyl-ethyl]-2-oxo-pyrrolidin-3-ylamino}-N-hydroxy-benzamide

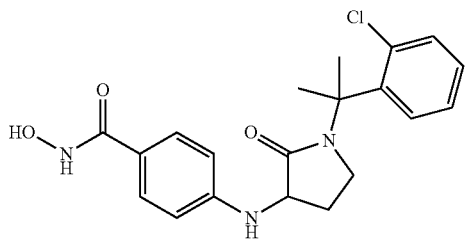 [SMILES: CC(C)(c1ccccc1Cl)N1CCC(Nc2ccc(C(=O)NO)cc2)C1=O]

The title compound was prepared in analogy to Example 1 in Scheme 11 by using 1-(2-chloro-phenyl)-1-methyl-ethylamine instead of aniline. MS: calc'd (MH+) 388, exp (MH+) 388. ¹H NMR (d-MeOD, 400 MHz), 7.58-7.54 (m, 3H), 7.38 (d, 1H, J=7.6 Hz), 7.31 (t, 1H, J=7.6 Hz), 7.22 (t, 1H, J=7.6 Hz), 6.69 (d, 2H, J=8.8 Hz), 4.20 (t, 1H, J=8.0 Hz), 3.75-3.67 (m, 2H), 2.68-2.64 (m, 1H), 1.96-1.92 (m, 1H), 1.79 (d, 6H, J=8.8 Hz).

Example 49

4-{1-[1-(3-Chloro-phenyl)-1-methyl-ethyl]-2-oxo-pyrrolidin-3-ylamino}-N-hydroxy-benzamide

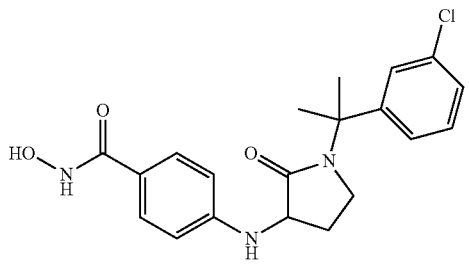 [SMILES: CC(C)(c1cccc(Cl)c1)N1CCC(Nc2ccc(C(=O)NO)cc2)C1=O]

The title compound was prepared in analogy to Example 1 in Scheme 11 by using 1-(3-chloro-phenyl)-1-methyl-ethylamine instead of aniline. MS: calc'd (MH+) 388, exp (MH+) 388. ¹H NMR (d-MeOD, 400 MHz), 7.56 (d, 1H, J=8.8 Hz), 7.39 (s, 1H), 7.33-7.32 (m, 2H), 7.25-7.22 (m, 1H), 6.71 (d, 2H, J=8.8 Hz), 4.25 (t, 1H, J=8.4 Hz), 3.70-3.64 (m, 2H), 2.66-2.63 (m, 1H), 1.95-1.89 (m, 1H), 1.75 (d, 6H, J=5.2 Hz).

Example 50

4-{1-[1-(4-Chloro-phenyl)-1-methyl-ethyl]-2-oxo-pyrrolidin-3-ylamino}-N-hydroxy-benzamide

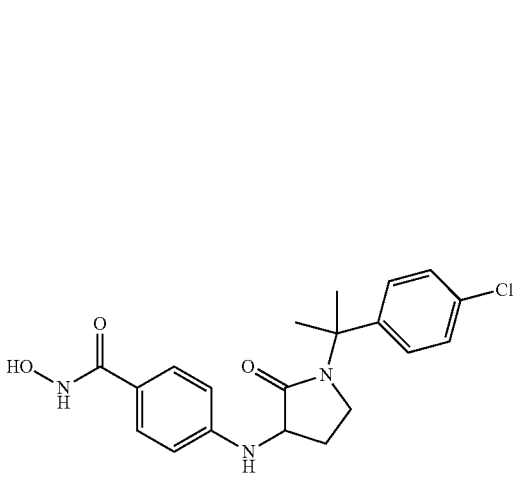 [SMILES: CC(C)(c1ccc(Cl)cc1)N1CCC(Nc2ccc(C(=O)NO)cc2)C1=O]

The title compound was prepared in analogy to Example 1 in Scheme 11 by using 1-(4-chloro-phenyl)-1-methyl-ethylamine instead of aniline. MS: calc'd (MH+) 388, exp (MH+) 388. ¹H NMR (d-MeOD, 400 MHz), 7.57 (d, 2H, J=7.2 Hz), 7.39-7.32 (m, 4H), 6.71 (d, 2H, J=7.6 Hz), 4.25 (t, 1H, J=9.2 Hz), 3.67-3.62 (m, 2H), 2.67-2.64 (m, 1H), 1.93-1.88 (m, 1H), 1.75 (s, 6H).

Example 51

4-[1-(1-Biphenyl-4-yl-1-methyl-ethyl)-2-oxo-pyrrolidin-3-ylamino]-N-hydroxy-benzamide

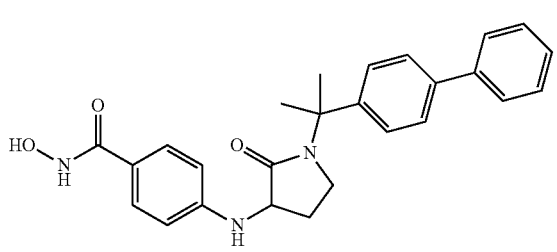 [SMILES: CC(C)(c1ccc(-c2ccccc2)cc1)N1CCC(Nc2ccc(C(=O)NO)cc2)C1=O]

The title compound was prepared in analogy to Example 1 in Scheme 11 by using 1-biphenyl-4-yl-1-methyl-ethylamine instead of aniline. MS: calc'd (MH+) 430, exp (MH+) 430. ¹H NMR (d-MeOD, 400 MHz), 7.62-7.34 (m, 11H), 6.72 (d, 2H, J=8.8 Hz), 4.26-4.23 (m, 1H), 3.71-3.61-3.63 (m, 2H), 2.71-2.63 (m, 1H), 1.98-1.92 (m, 1H), 1.82 (d, 6H, J=8.0 Hz).

Example 52

N-Hydroxy-4-[1-(1-methyl-1-naphthalen-1-yl-ethyl)-2-oxo-pyrrolidin-3-ylamino]-benzamide

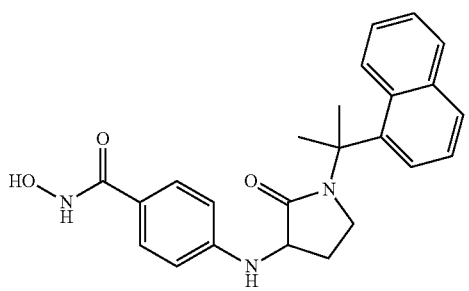 [SMILES: CC(C)(c1cccc2ccccc12)N1CCC(Nc2ccc(C(=O)NO)cc2)C1=O]

The title compound was prepared in analogy to Example 1 in Scheme 11 by using 1-methyl-1-naphthalen-1-yl-ethylamine instead of aniline. MS: calc'd (MH$^+$) 404, exp (MH$^+$) 404. $^1$H NMR (d-MeOD, 400 MHz), 8.22 (d, 1H, J=8.4 Hz), 7.89 (d, 1H, J=8.0 Hz), 7.79 (d, 1H, J=8.0 Hz), 7.65-7.43 (m, 7H), 6.65 (d, 2H, J=8.8 Hz), 4.18-4.15 (m, 1H), 3.45-3.42 (m, 2H), 2.54-2.49 (m, 1H), 1.84 (d, 6H, J=8.0 Hz), 1.81-1.78 (m, 1H).

Example 53

N-Hydroxy-4-[1-(1-methyl-1-naphthalen-2-yl-ethyl)-2-oxo-pyrrolidin-3-ylamino]-benzamide

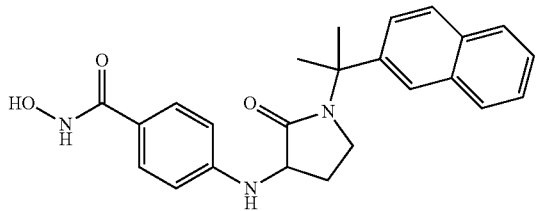 [SMILES: CC(C)(c1ccc2ccccc2c1)N1CCC(Nc2ccc(C(=O)NO)cc2)C1=O]

The title compound was prepared in analogy Example 1 in Scheme 11 by using 1-methyl-1-naphthalen-2-yl-ethylamine instead of aniline. MS: calc'd (MH$^+$) 404, exp (MH$^+$) 404. $^1$H NMR (d-MeOD, 400 MHz), 7.88-7.82 (m, 4H), 7.58-7.54 (m, 3H), 7.50-7.44 (m, 2H), 6.72 (d, 2H, J=8.8 Hz), 4.27 (t, 1H, J=8.8 Hz), 3.67-3.63 (m, 2H), 2.66-2.63 (m, 1H), 1.95-1.87 (m, 7H).

Example 54

N-Hydroxy-4-[2-oxo-1-(1-phenyl-cyclobutyl)-pyrrolidin-3-ylamino]-benzamide

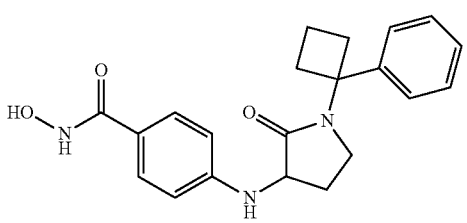 [SMILES: O=C(NO)c1ccc(NC2CCN(C3(c4ccccc4)CCC3)C2=O)cc1]

The title compound was prepared in analogy to Example 1 in Scheme 11 by using 1-phenyl-cyclobutylamine instead of aniline. MS: calc'd (MH$^+$) 366, exp (MH$^+$) 366. $^1$H NMR (d-MeOD, 400 MHz), 7.61 (d, 2H, J=8.0 Hz), 7.54 (d, 2H, J=7.6 Hz), 7.46 (d, 2H, J=6.8 Hz), 7.32 (d, 1H, J=6.8 Hz), 6.68 (d, 2H, J=7.6 Hz), 4.27 (t, 1H, J=9.2 Hz), 3.38-3.33 (m, 1H), 2.85-2.80 (m, 2H), 2.70-2.67 (m, 2H), 2.56-2.53 (m, 1H), 1.96-1.93 (m, 1H), 1.83-1.78 (m, 2H).

Example 55

N-Hydroxy-4-[2-oxo-1-(1-phenyl-cyclopentyl)-pyrrolidin-3-ylamino]-benzamide

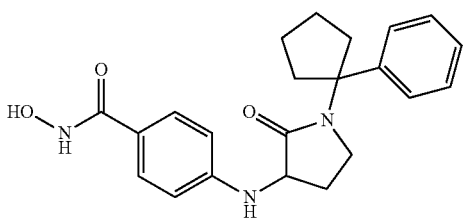 [SMILES: O=C(NO)c1ccc(NC2CCN(C3(c4ccccc4)CCCC3)C2=O)cc1]

The title compound was prepared in analogy to Example 1 in Scheme 11 by using 1-phenyl-cyclopentylamine instead of aniline. MS: calc'd (MH$^+$) 380, exp (MH$^+$) 380. $^1$H NMR (d-MeOD, 400 MHz), 7.55 (d, 2H, J=8.8 Hz), 7.47 (d, 2H, J=8.0 Hz), 7.36 (t, 2H, J=8.0 Hz), 7.26 (t, 1H, J=8.0 Hz), 6.68

(d, 2H, J=8.8 Hz), 4.21 (t, 1H, J=8.0 Hz), 3.55-3.51 (m, 2H), 2.72-2.54 (m, 3H), 2.31-2.22 (m, 2H), 1.86-1.72 (m, 5H).

Example 56

N-Hydroxy-4-[2-oxo-1-(1-phenyl-cyclohexyl)-pyrrolidin-3-ylamino]-benzamide

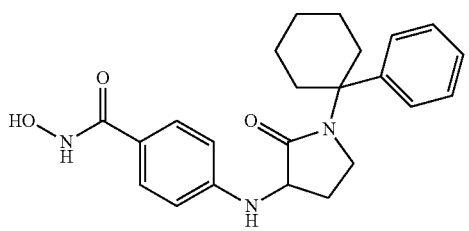 [SMILES: O=C(NO)c1ccc(NC2CCN(C3(c4ccccc4)CCCCC3)C2=O)cc1]

The title compound was prepared in analogy to Example 1 in Scheme 11 by using 1-phenyl-cyclohexylamine instead of aniline. MS: calc'd (MH$^+$) 394, exp (MH$^+$) 394. $^1$H NMR (d-MeOD, 400 MHz), 7.58 (d, 2H, J=8.8 Hz), 7.47 (d, 2H, J=8.0 Hz), 7.38 (t, 2H, J=8.0 Hz), 7.29 (t, 1H, J=7.6 Hz), 6.74 (d, 2H, J=8.8 Hz), 4.31-4.26 (m, 1H), 3.63-3.60 (m, 2H), 2.98-2.91 (m, 1H), 2.74-2.69 (m, 1H), 2.63-2.54 (m, 1H), 2.02-1.97 (m, 1H), 1.85-1.46 (m, 8H).

Example 57

N-Hydroxy-4-(3-methyl-2-oxo-1-phenyl-pyrrolidin-3-ylamino)-benzamide

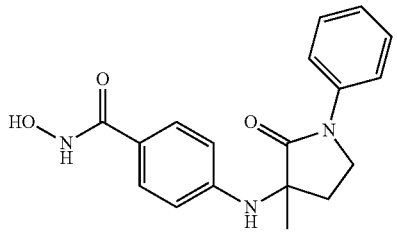 [SMILES: CC1(Nc2ccc(C(=O)NO)cc2)CCN(c2ccccc2)C1=O]

The title compound was prepared according to the general synthesis method shown in Scheme 2. A detailed synthesis route is provided in Scheme 12.

Scheme 12 (Example. 57)

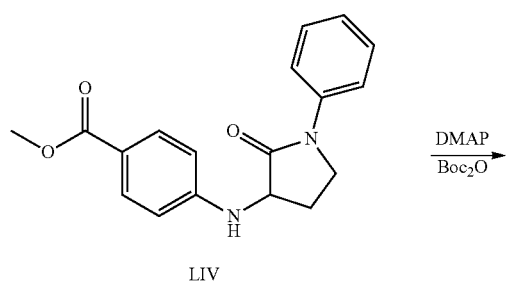

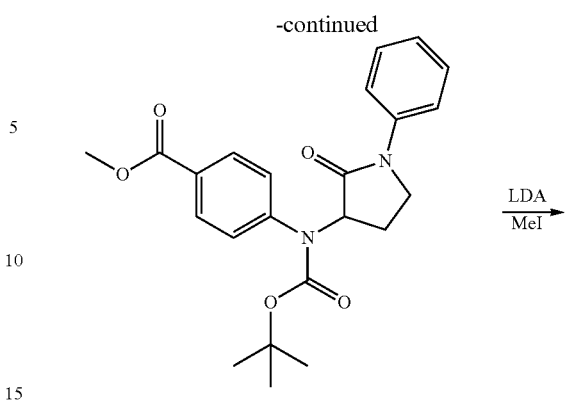

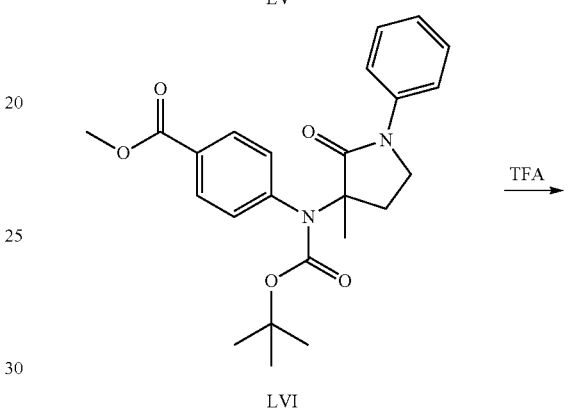

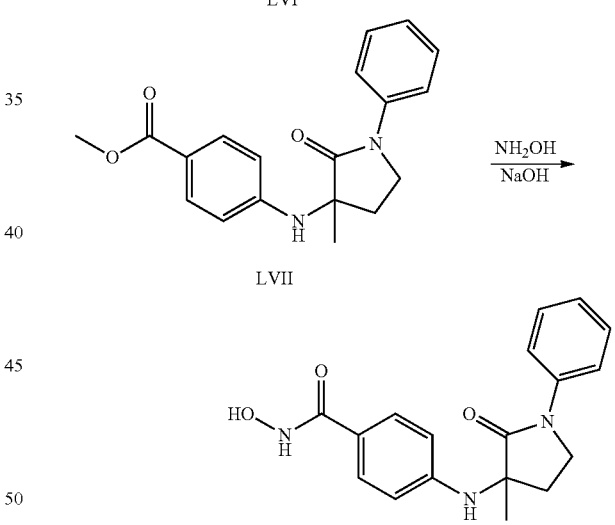

Compound LIV (310 mg, 1 mmol) was dissolved in CH$_3$CN (10 mL), followed by the addition of (Boc)$_2$O (432 mg, 2.0 mmol) and DMAP (24 mg, 0.20 mmol). The reaction mixture was stirred at rt for 12 hr. After removal of the solvent, the residual oil was purified on column to afford the compound LV (397 mg).

To a stirred solution of compound LV (397 mg, 0.97 mmol) in dry THF (3 mL) was added dropwise LDA (1.8 M, 0.75 mL, 1.341 mmol) at −78° C. under nitrogen. The reaction mixture was stirred at −78° C. for 30 min, and then MeI (0.17 mL, 2.682 mmol) was added dropwise. The reaction mixture was brought to rt and stirred overnight. When quenched with saturated NH$_4$Cl, the mixture was extracted with EtOAc, and dried over MgSO$_4$. After removal of the solvent, the crude product was directly dissolved in a mixed solvent of CH$_2$Cl$_2$ and TFA (4 mL, 3/1) at 0° C., which was stirred at 0° C. for 2 hr. Then the reaction mixture was concentrated and the residue was diluted with $CH_2Cl_2$, washed with saturated $NaHCO_3$, dried over $MgSO_4$. After removal of solvent, the crude product was dissolved in a mixture of MeOH and $NH_2OH$ hydrate (3 mL, 1/1). The reaction mixture was stirred at rt for 2 hr. Preparative HPLC separation afforded the titled compound Example 57 (107 mg). MS: calc'd (MH$^+$) 326, exp (MH$^+$) 326. $^1$H NMR (CD$_3$OD, 400 MHz), 7.70 (d, J=7.6 Hz, 2H), 7.57 (d, J=8.4 Hz, 2H), 7.45 (t, J=8.0 Hz, 2H), 7.25 (t, J=7.6 Hz, 1H), 6.66 (d, J=8.8 Hz, 2H), 4.03-3.95 (m, 2H), 2.72 (dt, J=13.2, 9.6 Hz, 1H), 2.19 (qd, J=6.4, 1.6 Hz, 1H), 1.57 (s, 3H).

Example 58

4-[1-(3-Fluoro-phenyl)-3-methyl-2-oxo-pyrrolidin-3-ylamino]-N-hydroxy-benzamide

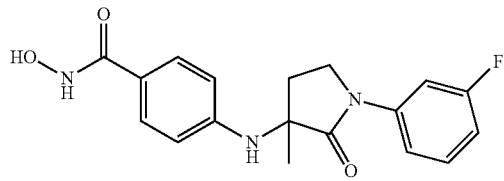 [SMILES: CC1(Nc2ccc(C(=O)NO)cc2)CCN(c2cccc(F)c2)C1=O]

The titled compound was prepared in analogy to Example 57 in Scheme 12 by using 4-[1-(3-fluoro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd (MH$^+$) 344, exp (MH$^+$) 344. $^1$H NMR (CD$_3$OD, 400 MHz), 7.69 (d, J=11.6 Hz, 1H), 7.56 (d, J=8.0 Hz, 2H), 7.50-7.42 (m, 2H), 6.99 (t, J=7.6 Hz, 1H), 6.64 (d, J=8.0 Hz, 2H), 3.99 (d, J=8.4 Hz, 2H), 2.75-2.68 (m, 1H), 2.21-2.18 (m, 1H), 1.56 (s, 3H).

Example 59

4-[1-(3-Chloro-phenyl)-3-methyl-2-oxo-pyrrolidin-3-ylamino]-N-hydroxy-benzamide

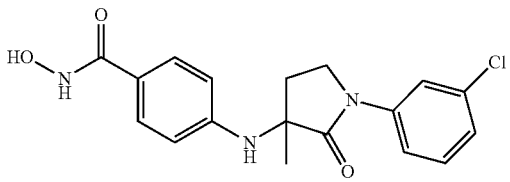 [SMILES: CC1(Nc2ccc(C(=O)NO)cc2)CCN(c2cccc(Cl)c2)C1=O]

The titled compound was prepared in analogy to Example 57 in Scheme 12 by using 4-[1-(3-chloro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd (MH$^+$) 360, exp (MH$^+$) 360. $^1$H NMR (CD$_3$OD, 400 MHz), 7.91 (t, J=2.0 Hz, 1H), 7.62 (ddd, J=8.2, 2.0, 0.8 Hz, 1H), 7.56 (d, J=6.8 Hz, 2H), 7.43 (t, J=8.0 Hz, 1H), 7.25 (ddd, J=8.0, 1.6, 0.8 Hz, 1H), 6.64 (d, J=9.2 Hz, 2H), 4.00-3.97 (m, 2H), 2.72 (dt, J=12.8, 10.0 Hz, 1H), 2.22-2.16 (m, 1H), 1.56 (s, 3H).

Example 60

4-[1-(4-Chloro-phenyl)-3-methyl-2-oxo-pyrrolidin-3-ylamino]-N-hydroxy-benzamide

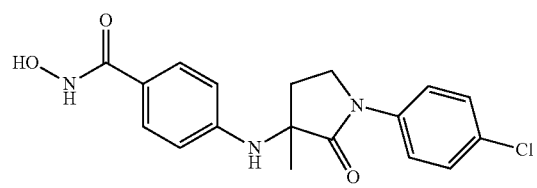 [SMILES: CC1(Nc2ccc(C(=O)NO)cc2)CCN(c2ccc(Cl)cc2)C1=O]

The titled compound was prepared in analogy to Example 57 in Scheme 12 by using 4-[1-(4-chloro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd (MH$^+$) 360, exp (MH$^+$) 360. $^1$H NMR (CD$_3$OD, 400 MHz) δ 7.74 (d, J=8.8 Hz, 2H), 7.56 (d, J=8.8 Hz, 2H), 7.44 (d, J=8.8 Hz, 2H), 6.64 (d, J=8.8 Hz, 2H), 4.00-3.96 (m, 2H), 2.72 (dt, J=12.8, 9.6 Hz, 1H), 2.22-2.16 (m, 1H), 1.56 (s, 3H).

Example 61

N-Hydroxy-4-(3-methyl-2-oxo-1-quinolin-3-yl-pyrrolidin-3-ylamino)-benzamide

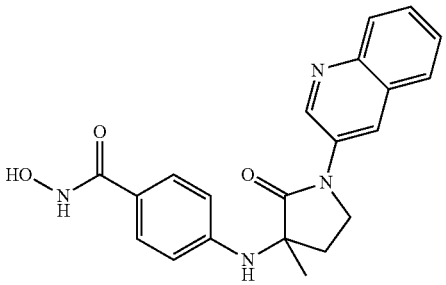

The titled compound was prepared in analogy to Example 57 in Scheme 12 by using 4-(2-oxo-1-quinolin-3-yl-pyrrolidin-3-ylamino)-benzoic acid methyl ester instead of 4-(2-oxo-1-phenyl-pyrrolidin-3-ylamino)-benzoic acid methyl ester. MS: calc'd (MH$^+$) 377.2 exp (MH$^+$) 377.2. $^1$H NMR (DMSO-d$_6$, 400 MHz), 10.79 (s, 1H), 9.42 (s, 1H), 8.54 (s, 1H), 8.02 (t, 2H, J=8.4 Hz), 7.74 (t, 1H, J=8.4 Hz), 7.71 (t, 1H, J=8.4 Hz), 7.62 (d, 2H, J=8.0 Hz), 7.23 (s, 1H), 7.10 (s, 1H), 6.97 (s, 1H), 6.63 (d, 2H, J=8.8 Hz), 4.12-4.07 (m, 2H), 2.68-2.58 (m, 1H), 2.21-2.16 (m, 1H), 1.52 (s, 3H).

Example 62

N-Hydroxy-4-(3-methyl-2-oxo-1-quinolin-8-yl-pyrrolidin-3-ylamino)-benzamide

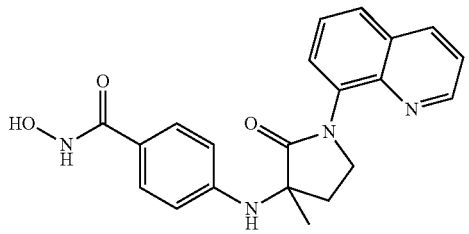 [SMILES: CC1(Nc2ccc(C(=O)NO)cc2)CCN(c2cccc3cccnc23)C1=O]

The titled compound was prepared in analogy to Example 57 in Scheme 12 by using 4-(2-oxo-1-quinolin-8-yl-pyrrolidin-3-ylamino)-benzoic acid methyl ester instead of 4-(2-oxo-1-phenyl-pyrrolidin-3-ylamino)-benzoic acid methyl ester. MS: calc'd (MH$^+$) 377.1 exp (MH$^+$) 377.1. $^1$H NMR (CD$_3$OD-d$_4$, 400 MHz), 9.07 (s, 1H), 8.46 (s, 1H), 8.03 (t, 1H, J=7.2 Hz), 7.80 (s, 1H), 7.71 (t, 1H, J=7.6 Hz), 7.71 (m, 3H), 7.02 (d, 2H, J=8.8 Hz), 4.13 (m, 2H), 2.97 (m, 1H), 2.25 (m, 1H), 1.75 (s, 3H).

Example 63

N-Hydroxy-4-(3-methyl-2-oxo-1-quinolin-6-yl-pyrrolidin-3-ylamino)-benzamide

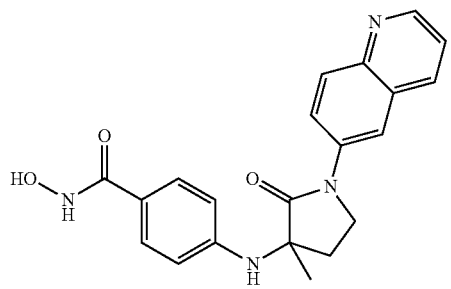 [SMILES: CC1(Nc2ccc(C(=O)NO)cc2)CCN(c2ccc3ncccc3c2)C1=O]

The titled compound was prepared in analogy to Example 57 in Scheme 12 by using 4-(2-oxo-1-quinolin-6-yl-pyrrolidin-3-ylamino)-benzoic acid methyl ester instead of 4-(2-oxo-1-phenyl-pyrrolidin-3-ylamino)-benzoic acid methyl ester. MS: calc'd (MH$^+$) 377.1 exp (MH$^+$) 377.1. $^1$H NMR (CD$_3$OD-d$_4$, 400 MHz), 9.06 (d, 1H, J=5.2 Hz), 8.95 (d, 1H, J=8.4 Hz), 8.71 (dd, 1H, J=2.4 Hz), 8.46 (d, 1H, J=2.4 Hz), 8.25 (d, 1H, J=9.6 Hz), 7.95-7.92 (m, 1H), 7.58 (d, 2H, J=8.8 Hz), 6.70 (d, 2H, J=8.8 Hz), 4.22-4.13 (m, 2H), 2.84-2.77 (m, 1H), 2.30-2.26 (m, 1H), 1.62 (s, 3H).

Example 64

N-Hydroxy-4-[3-methyl-1-(1-methyl-1-phenyl-ethyl)-2-oxo-pyrrolidin-3-ylamino]-benzamide

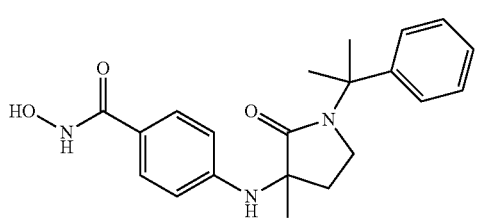 [SMILES: CC1(Nc2ccc(C(=O)NO)cc2)CCN(C(C)(C)c2ccccc2)C1=O]

The titled compound was prepared in analogy to Example 57 in Scheme 12 by using 4-[1-(1-methyl-1-phenyl-ethyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd (MH$^+$) 368, exp (MH$^+$) 368. $^1$H NMR (d-MeOD, 400 MHz), 7.54 (d, 2H, J=8.0 Hz), 7.43 (d, 2H, J=8.0 Hz), 7.35 (t, 2H, J=8.0 Hz), 7.25 (t, 1H, J=8.0 Hz), 6.59 (d, 2H, J=8.0 Hz), 3.77-3.72 (m, 1H), 3.63-3.59 (m, 1H), 2.59-2.50 (m, 1H), 2.05-2.01 (m, 1H), 1.80 (s, 6H), 1.78 (s, 6H), 1.42 (s, 3H).

Example 65

4-[3-Ethyl-1-(1-methyl-1-phenyl-ethyl)-2-oxo-pyrrolidin-3-ylamino]-N-hydroxy-benzamide

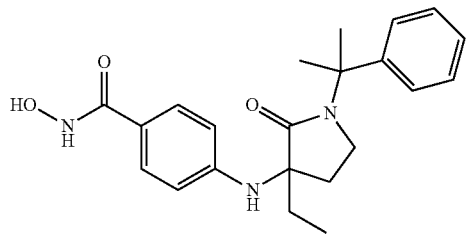 [SMILES: CCC1(Nc2ccc(C(=O)NO)cc2)CCN(C(C)(C)c2ccccc2)C1=O]

The titled compound was prepared in analogy to Example 57 in Scheme 12 by using 4-[1-(1-methyl-1-phenyl-ethyl)-2-oxo-pyrrolidin-3-ylamino]-benzoic acid methyl ester instead of 4-(2-oxo-1-phenyl-pyrrolidin-3-ylamino)-benzoic acid methyl ester, and iodoethane instead of iodomethane in the alkylation reaction. MS: calc'd (MH$^+$) 382, exp (MH$^+$) 382. $^1$H NMR (d-MeOD, 400 MHz), 7.53 (d, 2H, J=8.0 Hz), 7.44 (d, 2H, J=8.0 Hz), 7.35 (t, 2H, J=8.0 Hz), 7.25 (t, 1H, J=8.0

Hz), 6.62 (d, 2H, J=8.0 Hz), 3.72-3.61 (m, 2H), 2.48-2.45 (m, 1H), 2.20-2.16 (m, 1H), 1.89-1.79 (m, 1H), 1.78 (s, 6H), 0.96 (t, 3H, J=4.0 Hz).

Example 66

2-Fluoro-N-hydroxy-4-(2-oxo-1-phenyl-pyrrolidin-3-ylamino)-benzamide

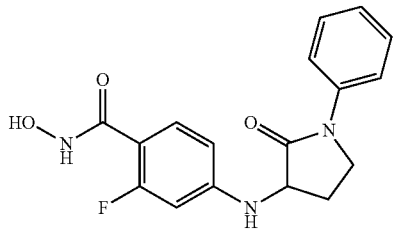 [SMILES: O=C(NO)c1ccc(NC2CCN(c3ccccc3)C2=O)cc1F]

The title compound was prepared in analogy to Example 1 in Scheme 11 by using 4-bromo-2-fluoro-benzoic acid methyl ester instead of 4-iodo-benzoic acid methyl ester. MS: calc'd (MH$^+$) 330, exp (MH$^+$) 330. $^1$H NMR (CD$_3$OD, 400 MHz), 7.68 (d, 2H, J=8.4 Hz), 7.59 (t, 1H, J=8.4 Hz), 7.42 (t, 2H, J=8.4 Hz), 6.64 (d, 1H, J=8.4 Hz), 6.54 (d, 1H, J=14.4 Hz), 4.53 (t, 1H, J=8.0 Hz), 4.00-3.87 (m, 2H), 2.79-2.71 (m, 1H), 2.10-2.00 (m, 1H).

Example 67

4-[1-(3-Chloro-phenyl)-2-oxo-pyrrolidin-3-ylamino]-2-fluoro-N-hydroxy-benzamide

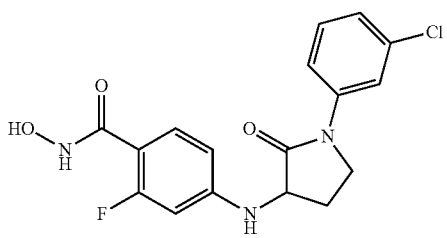 [SMILES: O=C(NO)c1ccc(NC2CCN(c3cccc(Cl)c3)C2=O)cc1F]

The title compound was prepared in analogy to Example 1 in Scheme 11 by using 3-chlorophenylamine instead of aniline, 4-bromo-2-fluoro-benzoic acid methyl ester instead of 4-iodo-benzoic acid methyl ester. MS: calc'd (MH$^+$) 364, exp (MH$^+$) 364. $^1$H NMR (d-MeOD, 400 MHz), 7.89 (s, 1H), 7.61-7.56 (m, 2H), 7.40 (t, 1H, J=8.0 Hz), 7.22 (d, 2H, J=8.0 Hz), 6.64 (t, 1H, J=8.4 Hz), 6.54 (d, 1H, J=14.0 Hz), 4.53 (t, 1H, J=8.4 Hz), 3.96-3.91 (m, 2H), 2.78-2.71 (m, 1H), 2.07-1.96 (m, 1H).

Example 68

4-[1-(3,4-Dichloro-phenyl)-2-oxo-pyrrolidin-3-ylamino]-2-fluoro-N-hydroxy-benzamide

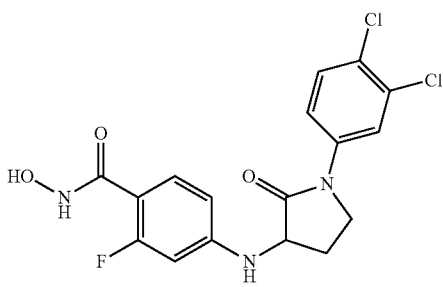 [SMILES: O=C(NO)c1ccc(NC2CCN(c3ccc(Cl)c(Cl)c3)C2=O)cc1F]

The title compound was prepared in analogy to Example 1 in Scheme 11 by using 3,4-dichlorophenylamine instead of aniline, 4-bromo-2-fluoro-benzoic acid methyl ester instead of 4-iodo-benzoic acid methyl ester. MS: calc'd (MH$^+$) 398, exp (MH$^+$) 398. $^1$H NMR (d-MeOD, 400 MHz), 8.07 (s, 1H), 7.61-7.54 (m, 3H), 6.64 (d, 1H, J=8.8 Hz), 6.54 (d, 1H, J=14.8 Hz), 4.56-4.51 (m, 1H), 3.93-3.90 (m, 2H), 2.78-2.74 (m, 1H), 2.08-2.03 (m, 1H).

Example 69

3-Chloro-N-hydroxy-4-(2-oxo-1-phenyl-pyrrolidin-3-ylamino)-benzamide

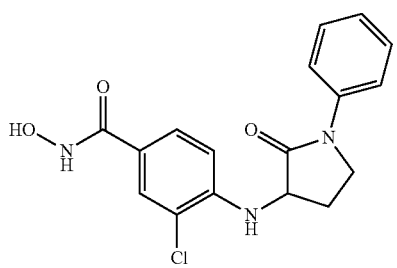 [SMILES: O=C(NO)c1ccc(NC2CCN(c3ccccc3)C2=O)c(Cl)c1]

The title compound was prepared in analogy to Example 1 in Scheme 11 by using 4-bromo-3-chloro-benzoic acid methyl ester instead of 4-bromo-2-fluoro-benzoic acid methyl ester. MS: calc'd (MH$^+$) 346, exp (MH$^+$) 346. $^1$H NMR (d-MeOD, 400 MHz), 7.76 (s, 1H), 7.70 (d, 2H, J=8.0 Hz), 7.62 (d, 1H, J=8.4 Hz), 7.43 (t, 2H, J=8.0 Hz), 7.23 (t, 1H, J=8.0 Hz), 6.96 (d, 1H, J=8.8 Hz), 4.60 (t, 1H, J=8.0 Hz), 4.02-3.90 (m, 2H), 2.85-2.82 (m, 1H), 2.17-2.11 (m, 1H).

Example 70
4-[1-(4-Fluoro-phenyl)-5-oxo-pyrrolidin-3-ylamino]-N-hydroxy-benzamide
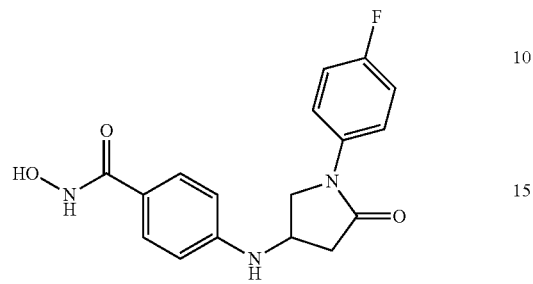
The title compound was prepared according to the general synthesis method shown in Scheme 3. A detailed synthesis route is provided in Scheme 13.
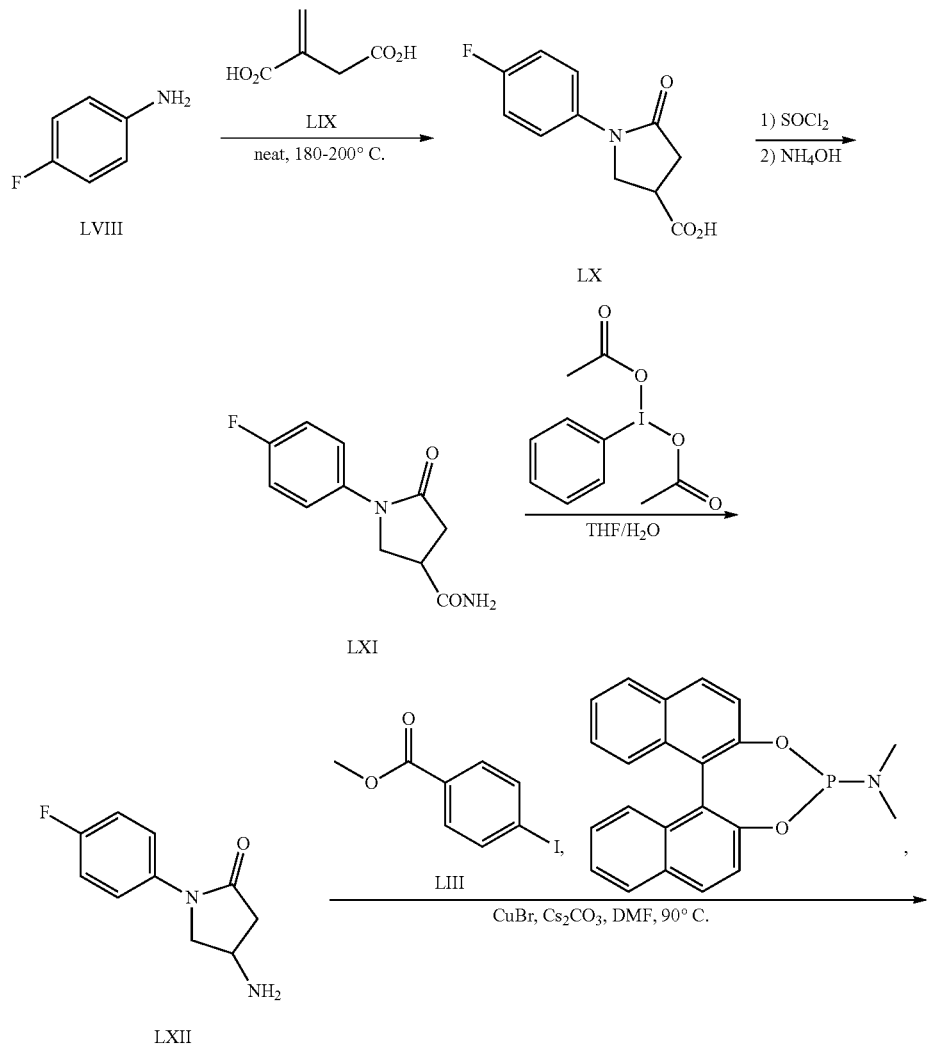
Scheme 13 (Ex. 70)

-continued

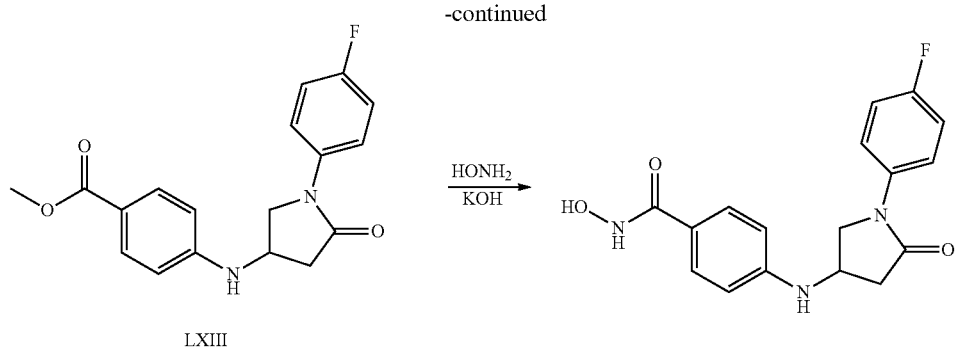

LXIII

A mixture of itaconic acid LIX (2.60 g, 20 mmol) and 4-fluoroaniline LVIII (2.22 g, 20 mmol) was heated at 180~200° C. for 0.5 hr. When the mixture was brought to rt, the resulted product was recrystallized from EtOAc to afford LX as white solid (4.0 g).

To a suspension solution of LX (4.0 g) in 1,2-dichloroethane (30 mL) was added dropwise thionyl chloride (4 mL), then the mixture was heated to 80° C. for 1 hr. After 1,2-dichloroethane and excess thionyl chloride were removed in vacuo, the residue was dissolved in THF (10 mL) and added dropwise to aqueous ammonia (20 mL) in THF (10 mL). The mixture was stirred for 1 hr at rt. After removal of THF, the white solid was collected and dried to afford LXI (3.4 g).

To a suspension of LXI (1.3 g) in THF (20 mL) and water (20 mL) was added (diacetoxyiodo)benzene (1.9 g), and the mixture was stirred overnight. After removal of THF, the remained aqueous solution was acidified by HCl to pH 2, and washed with EtOAc twice (15 mL). The aqueous phase was separated, concentrated and dried to afford LXII as pale grey solid (1.1 g).

A mixture of LXII (166 mg), 4-iodobenzoate ester LIII (190 mg, 0.73 mmol), cesium carbonate (714 mg, 2.2 mmol), cuprous bromide (5.3 mg, 0.04 mmol) and (3,5-dioxa-4-phospha-cyclohepta[2,1-a;3,4-a']dinaphthalen-4-yl)-dimethyl-amine (28 mg, 0.08 mmol) in DMF (3 mL) was charged with nitrogen and heated at 100° C. overnight. The mixture was cooled to rt and diluted with EtOAc (30 mL) and washed with water (10 mL). The organic layer was separated, dried over anhydrous sodium sulfate and concentrated. The residue was purified by column chromatography (eluate: EtOAc/petroleum ether from 1/3 to 1/2) to afford LXIII as white solid (73 mg).

To a solution of LXIII (73 mg, 0.24 mmol) in MeOH (2 mL) was added hydroxylamine (1 mL, 50% aqueous solution) and KOH (10 mg), and the mixture was heated to 60° C. for 3 hr. After cooling, the mixture was purified by preparative HPLC to afford Example 70 as white solid (21 mg). MS: calc'd (MH$^+$) 330 exp (MH$^+$) 330. $^1$H NMR (DMSO-d$_6$, 400 MHz), 10.84 (b, 1H), 7.71-7.68 (m, 2H), 7.57 (d, 2H, J=8.8 Hz), 7.24-7.20 (m, 2H), 6.61 (d, 2H, J=8.8 Hz), 4.26-4.22 (m, 2H), 3.66-3.63 (m, 1H), 3.03 (dd, 1H, J$_1$=16.8 Hz, J$_2$=7.2 Hz), 2.44 (dd, 1H, J$_1$=16.8 Hz, J$_2$=3.2 Hz).

Example 71

4-[1-(2-Chloro-phenyl)-5-oxo-pyrrolidin-3-ylamino]-N-hydroxy-benzamide

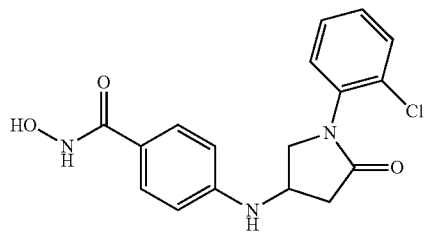 [SMILES: O=C(NO)c1ccc(NC2CC(=O)N(c3ccccc3Cl)C2)cc1]

The title compound was prepared in analogy to Example 70 in Scheme 13 by using 2-chlorophenylamine instead of 4-fluoroaniline. MS: calc'd (MH$^+$) 346 exp (MH$^+$) 346. $^1$H NMR (DMSO-d$_6$, 400 MHz), 7.58-7.56 (m, 3H), 7.47-7.37 (m, 3H), 6.64 (d, 2H, J=8.8 Hz), 4.5-4.33 (m, 1H), 4.10 (dd, 1H, J$_1$=9.6 Hz, J$_2$=6.4 Hz), 3.53 (dd, 1H, J$_1$=9.6 Hz, J$_2$=4.0 Hz), 2.98 (dd, 1H, J$_1$=16.8 Hz, J$_2$=7.6 Hz), 2.40 (dd, 1H, J$_1$=17.2 Hz, J$_2$=4.4 Hz).

Example 72

4-[1-(3-Chloro-phenyl)-5-oxo-pyrrolidin-3-ylamino]-N-hydroxy-benzamide

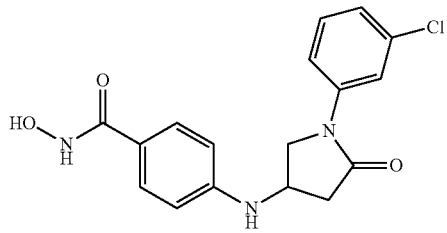 [SMILES: O=C(NO)c1ccc(NC2CC(=O)N(c3cccc(Cl)c3)C2)cc1]

The title compound was prepared in analogy to Example 70 in Scheme 13 by using 3-chlorophenylamine instead of 4-fluoroaniline. MS: calc'd (MH$^+$) 346 exp (MH$^+$) 346. $^1$H NMR (DMSO-d$_6$, 400 MHz), 10.83 (b, 1H), 7.89 (t, 1H, J=2.0 Hz), 7.57 (d, 2H, J=8.8 Hz), 7.40 (t, 1H, J=8.0 Hz), 7.22-719 (m, 1H), 6.62 (d, 2H, J=8.8 Hz), 4.26 (dd, 2H, J$_1$=12.4 Hz, J$_2$=6.0 Hz), 3.66 (dd, 1H, J$_1$=12.8 Hz, J$_2$=6.0 Hz), 3.06 (dd, 1H, J$_1$=16.8 Hz, J$_2$=6.8 Hz), 2.47 (dd, 1H, J$_1$=16.8 Hz, J$_2$=2.8 Hz).

Example 73

4-[1-(4-Chloro-phenyl)-5-oxo-pyrrolidin-3-ylamino]-N-hydroxy-benzamide

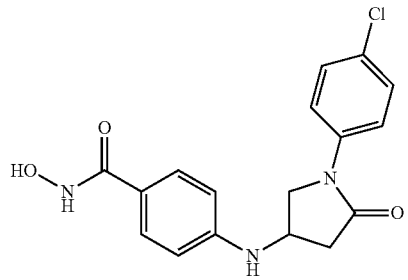 [SMILES: O=C(NO)c1ccc(NC2CC(=O)N(c3ccc(Cl)cc3)C2)cc1]

The title compound was prepared in analogy to Example 70 in Scheme 13 by using 4-chlorophenylamine instead of 4-fluoroaniline. MS: calc'd (MH$^+$) 346 exp (MH$^+$) 346. $^1$H NMR (DMSO-d$_6$, 400 MHz), 10.83 (b, 1H), 8.72 (b, 1H), 773-7.70 (m, 2H), 7.57 (d, 2H, J=8.4 Hz), 7.45-7.42 (m, 2H), 6.67 (d, 1H, J=5.6 Hz), 6.62 (d, 2H, J=8.8 Hz), 4.26-4.22 (m, 2H), 3.66-3.63 (m, 1H), 3.05 (dd, 1H, J$_1$=16.8 Hz, J$_2$=7.2 Hz), 2.46 (dd, 1H, J$_1$=16.8 Hz, J$_2$=3.2 Hz).

Example 74

N-Hydroxy-4-[1-(3-methoxy-phenyl)-5-oxo-pyrrolidin-3-ylamino]-benzamide

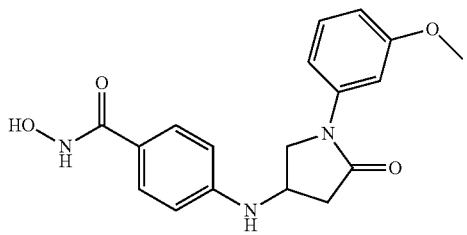 [SMILES: COc1cccc(N2CC(Nc3ccc(C(=O)NO)cc3)CC2=O)c1]

The title compound was prepared in analogy to Example 70 in Scheme 13 by using 3-methoxyphenylamine instead of 4-fluoroaniline. MS: calc'd (MH$^+$) 342 exp (MH$^+$) 342. $^1$H NMR (DMSO-d$_6$, 400 MHz), 10.84 (b, 1H), 7.57 (d, 2H, J=8.8 Hz), 7.36 (t, 1H, J=2.0 Hz), 7.28 (t, 1H, J=8.0 Hz), 7.19-7.16 (m, 1H), 6.74-6.72 (m, 1H), 6.61 (d, 2H, J=8.8 Hz), 4.26-4.22 (m, 2H), 3.77 (s, 3H), 3.66-3.63 (m, 1H), 3.03 (dd, 1H, J$_1$=16.8 Hz, J$_2$=7.2 Hz), 2.44 (dd, 1H, J$_1$=16.8 Hz, J$_2$=2.8 Hz).

Example 75

4-(1-Benzyl-5-oxo-pyrrolidin-3-ylamino)-N-hydroxy-benzamide

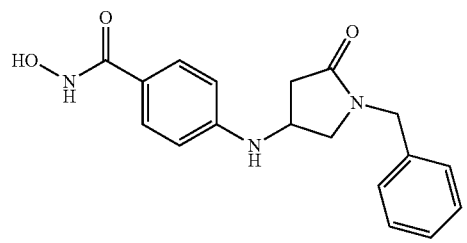 [SMILES: O=C(NO)c1ccc(NC2CC(=O)N(Cc3ccccc3)C2)cc1]

The title compound was prepared in analogy to Example 70 in Scheme 13 by using benzylamine instead of 4-fluoroaniline. MS: calc'd (MH$^+$) 326, exp (MH$^+$) 326. $^1$H NMR (CD$_3$OD, 400 MHz), 7.56 (d, J=8.8 Hz, 2H), 7.36-7.33 (m, 2H), 7.30-7.27 (m, 3H), 6.61 (d, J=8.8 Hz, 2H), 4.51 (d, J=2.0 Hz, 2H), 4.26-4.22 (m, 1H), 3.73 (dd, J=10.4, 6.8 Hz, 1H), 3.22 (dd, J=10.0, 3.2 Hz, 1H), 2.97 (dd, J=16.8, 7.6 Hz, 1H), 2.42 (dd, J=16.8, 3.6 Hz, 1H).

Example 76

N-Hydroxy-4-[1-(1-methyl-1-phenyl-ethyl)-5-oxo-pyrrolidin-3-ylamino]-benzamide

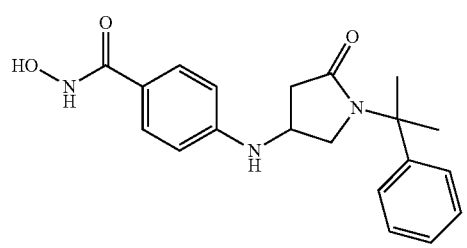 [SMILES: CC(C)(c1ccccc1)N1CC(Nc2ccc(C(=O)NO)cc2)CC1=O]

The title compound was prepared in analogy to Example 70 in Scheme 13 by using 1-methyl-1-phenyl-ethylamine instead of 4-fluoroaniline. MS: calc'd (MH+) 354 exp (MH+) 354. $^1$H NMR (DMSO-d$_6$, 400 MHz), 7.56 (d, 2H, J=8.4 Hz), 7.34-7.26 (m, 4H), 7.20-7.18 (m, 1H), 6.62-6.56 (m, 3H), 4.12-4.11 (m, 1H), 3.94-3.90 (m, 1H), 3.33 (dd, 1H, J$_1$=10.0

Hz, $J_2$=4.0 Hz), 2.76 (dd, 1H, $J_1$=16.8 Hz, $J_2$=8.0 Hz), 2.21 (dd, 1H, $J_1$=16.8 Hz, $J_2$=4.8 Hz), 1.62 (d, 6H, J=5.2 Hz).
Example 77
Trans-4-[1-(4-Chloro-phenyl)-2-methyl-5-oxo-pyrrolidin-3-ylamino]-N-hydroxy-benzamide
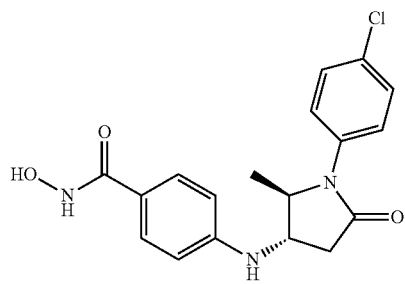
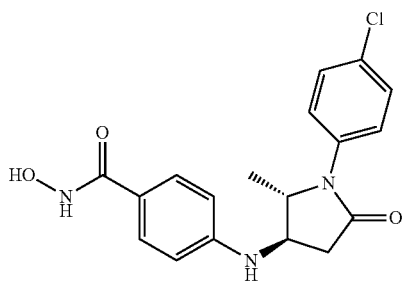
The title compound was prepared according to the general synthesis method shown in Scheme 4. A detailed synthesis route is shown in Scheme 14.
scheme 14 (Ex. 77)
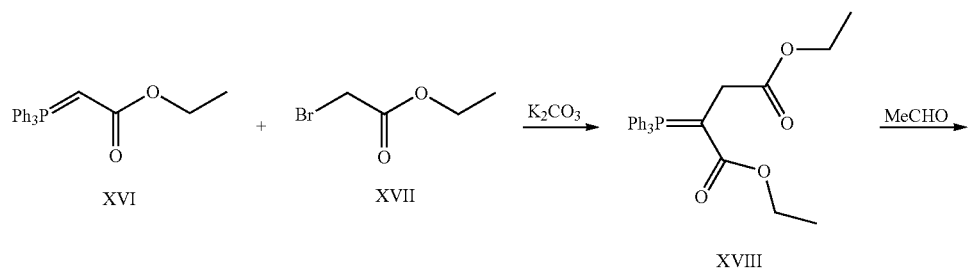
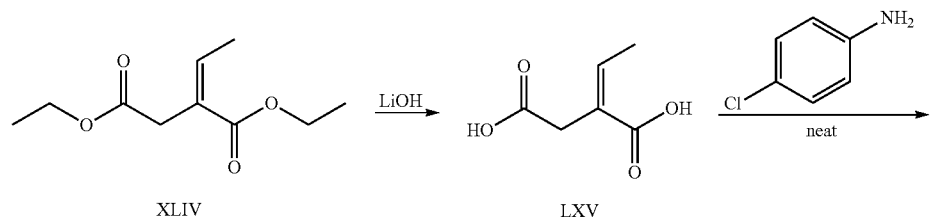
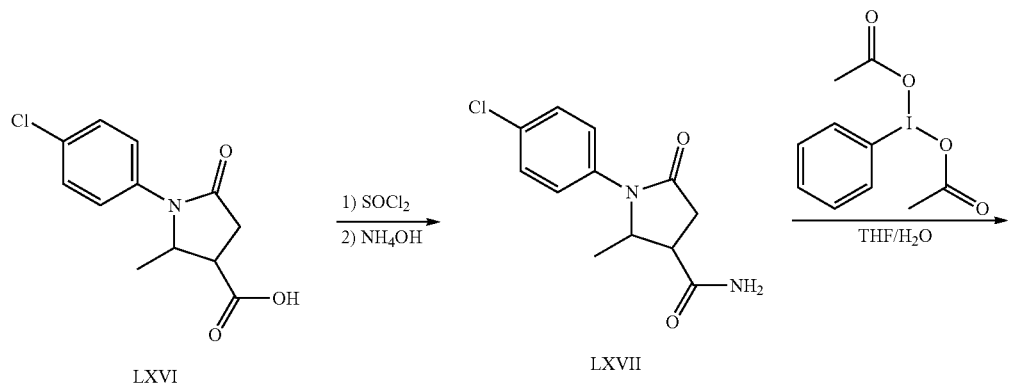

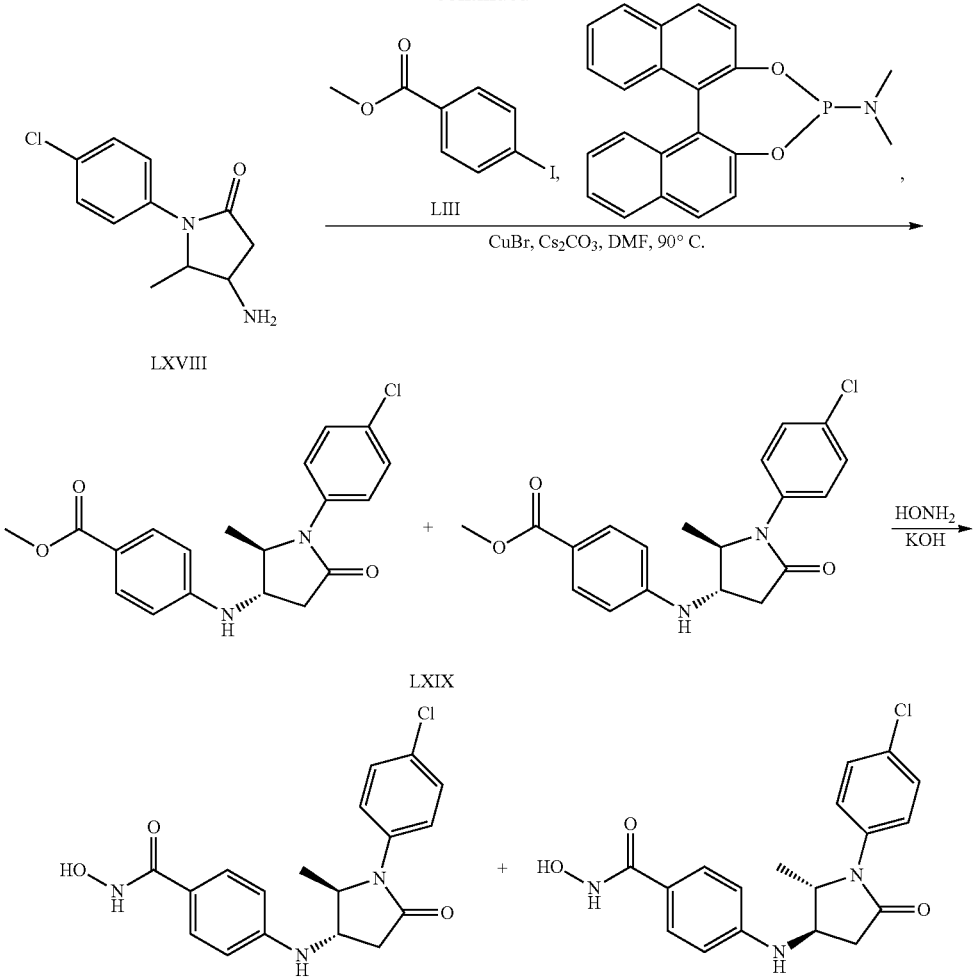

A suspension solution of (triphenyl-phosphanylidene)-acetic acid ethyl ester XVI (13.9 g, 40 mmol), bromo-acetic acid ethyl ester XVII (6.7 g, 40 mmol) and potassium carbonate (8.3 g, 60 mmol) in EtOAc (300 mL) was heated to reflux for 4 hr. After cooling, the solid was filtered off and washed with EtOAc (100 mL). The combined filtrate was concentrated to afford XVIII as viscous oil, which was used directly in next step.

The crude product XVIII was dissolved in DCM (200 mL), to which was added aqueous acetaldehyde (40%, 20 mL), and the mixture was stirred overnight. After that, the mixture was washed with brine. The organic layer was separated, dried, and concentrated. The residue was purified by column chromatography to afford LXIV as light yellow oil (5.5 g, yield 69%).

To a solution of 2-Eth-(Z)-ylidene-succinic acid diethyl ester LXIV (3.0 g, 15 mmol) in THF (30 mL) and water (30 mL) was added lithium hydroxide (0.54 g, 45 mmol), and the mixture was heated to 60° C. for 3 hr. Then the THF was evaporated off, and the remaining aqueous phase was acidified by concentrated HCl to pH~1. The mixture was extracted with EtOAc (100 mL×2). The organic layer was separated, dried, and concentrated to afford LXV as white solid (2.0 g, yield 93%).

A mixture of LXV (2.0 g, 100 mmol) and 4-chloroaniline (1.9 g, 13.8 mmol) was heated at 180~200° C. for 0.5 hr. After cooling, the result product was dissolved in EtOAc (50 mL) and extracted with 2% aqueous NaOH (30 mL×2). The combined aqueous phase was acidified by concentrated HCl to pH~1. The mixture was extracted with EtOAc (50 mL×2). The organic layer was separated, dried, and concentrated to afford LXVI as light brown solid (1.4 g).

To a suspension solution of LXVI (1.4 g) in 1,2-dichloroethane (30 mL) was added thionyl chloride (2 mL) in dropwise, then the mixture was heated to 80° C. for 1 hr, and the reaction mixture became clear. 1,2-Dichloroethane and excess thionyl chloride were removed and the residue was dissolved in THF (10 mL) and added dropwise to aqueous ammonia (10 mL) in THF (10 mL). The mixture was stirred at rt for 1 hr. After removal of THF, the remained aqueous solution was filtered, dried to afford LXVII as white solid (1.2 g).

A suspension solution of LXVII (420 mg, 1.72 mmol) in THF (20 mL) and water (20 mL) was heated to reflux, to which was added (diacetoxyiodo)benzene (1.9 g, 5.4 mmol) as one portion, and the mixture was stirred at refluxing for 3 hr. After cooling and removal of THF, the remaining aqueous solution was acidified by HCl to pH~2, and washed with EtOAc (15 mL×2). The aqueous phase was separated, concentrated and dried to afford LXVIII as light brown solid (186 mg).

A mixture of LXVIII (100 mg, 0.38 mmol), 4-iodo-benzoic acid methyl ester (110 mg, 0.42 mmol), cesium carbonate (372 mg, 1.14 mmol), Pd(dba)$_2$ (17 mg, 0.02 mmol) and (3,5-4,5-bis-diphenylphosphanyl-9,9-dimethyl-9H-xanthene (22 mg, 0.04 mmol) in 1,4-dioxane (5 mL) was charged with nitrogen and heated at 110° C. overnight. After cooling, the mixture was filtered and washed with EtOAc. The combined filtrate was concentrated, and the residue was purified by column chromatography (eluate: EtOAc/petroleum ether from 1/3 to 1/2) to afford LXIX as light yellow oil (75 mg).

To a solution of LXIX (75 mg) in MeOH (2 mL) was added hydroxylamine (1 mL, 50% aqueous solution) and KOH (10 mg), and the mixture was heated at 60° C. for 3 hr. The mixture was purified by preparative HPLC to afford Example 77 as white solid (20 mg). MS: calc'd (MH+) 360 exp (MH+) 360. $^1$H NMR (DMSO-d$_6$, 400 MHz), 10.83 (b, 1H), 8.72 (b, 1H), 7.64-7.51 (m, 4H), 7.45-7.43 (m, 2H), 6.71 (d, 1H, J=6.4 Hz), 6.59 (d, 2H, J=8.8 Hz), 4.23-4.21 (m, 1H), 3.87-3.84 (m, 1H), 3.18 (dd, 1H, J$_1$=17.2 Hz, J$_2$=7.2 Hz), 2.32 (dd, 1H, J$_1$=13.2 Hz, J$_2$=2.0 Hz), 1.29 (d, 3H, J=6.4 Hz).

Example 78

4-[1-(4-Chloro-phenyl)-4-methyl-5-oxo-pyrrolidin-3-ylamino]-N-hydroxy-benzamide

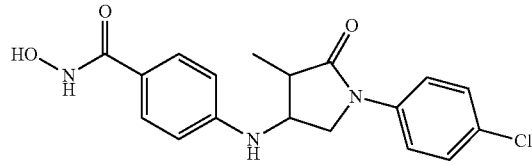 [SMILES: CC1C(=O)N(c2ccc(Cl)cc2)CC1Nc1ccc(C(=O)NO)cc1]

The title compound was prepared according to the general synthesis method shown in Scheme 5. And a detailed synthesis route was provided as shown in Scheme 15.

scheme 15 (Ex. 78)

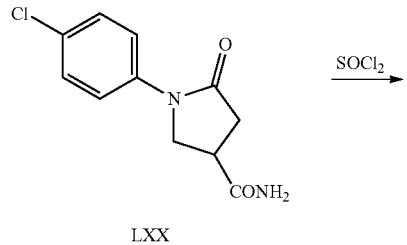

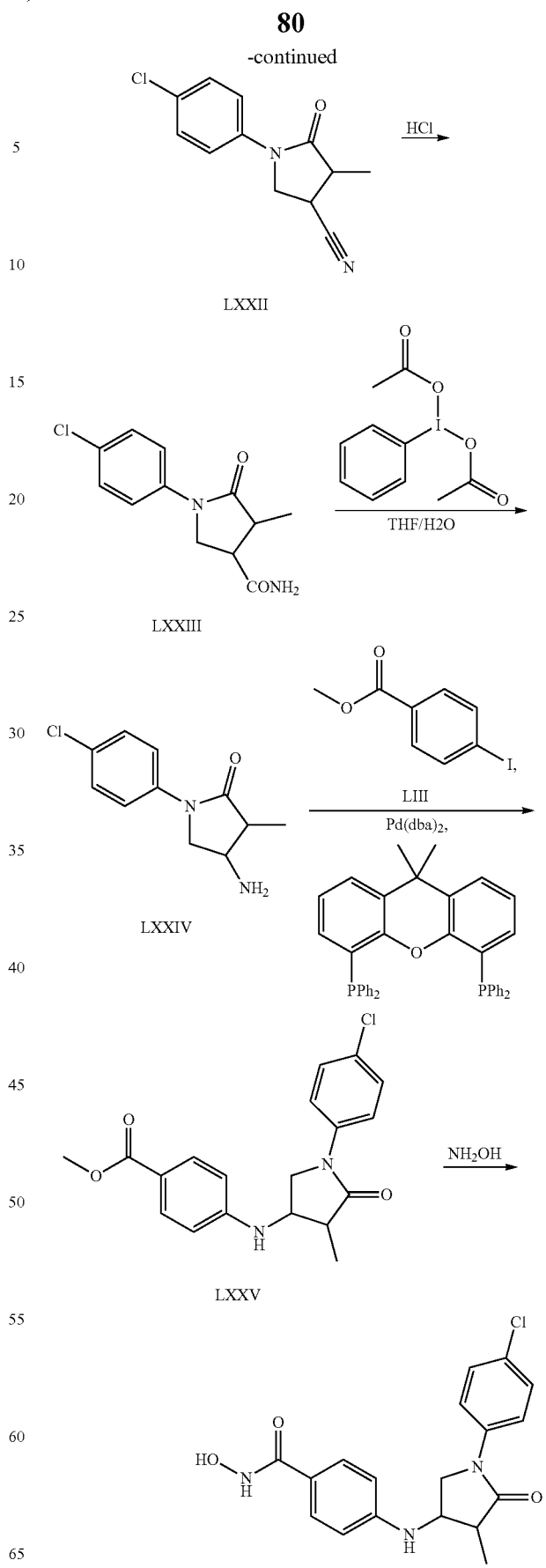

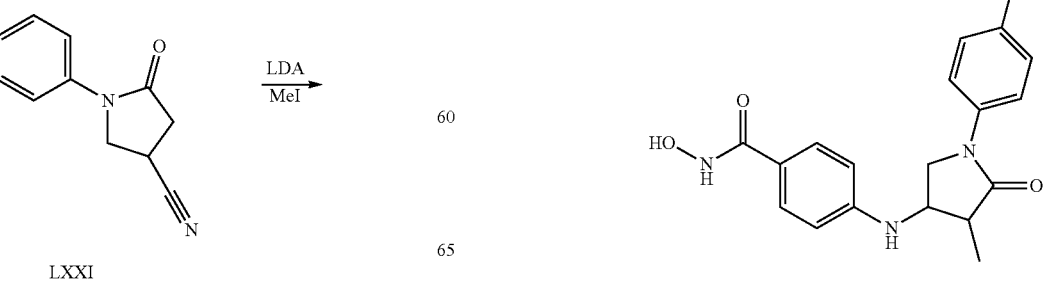

To a suspension solution of the amide LXX (from the intermediate Example 73) (900 mg, 3.78 mmol) in 1,2-dichloroethane (10 mL) was added thionyl chloride (2 mL). The mixture was heated at 80° C. for 3 hr, and became clear when the reaction was complete. After removal of 1,2-dichloroethane and excess thionyl chloride, the residue was dissolved in DCM (20 mL) and washed with aqueous sodium carbonate (10 mL). The organic layer was separated, dried, and concentrated to afford 810 mg of 1-(4-chloro-phenyl)-5-oxo-pyrrolidine-3-carbonitrile LXXI as light brown oil.

To a solution of LXXI (800 mg, 3.63 mmol) in THF (30 mL) was added dropwise LDA (1.8 M in toluene, 2 mL) at −78° C. After the mixture was stirred at −78° C. for 1 hr, MeI (1 mL) was added dropwise into the solution. When the mixture was brought to rt, it was quenched with aqueous NH$_4$Cl, and extracted with EtOAc (20 mL×2). The organic layer was separated, dried, and concentrated. The residue was purified by column chromatography to afford LXXII as light yellow oil (420 mg, yield 49%).

A suspension solution of 1-(4-chloro-phenyl)-4-methyl-5-oxo-pyrrolidine-3-carbonitrile LXXII (420 mg, 1.79 mmol) in HCl (6 N, 10 mL) was stirred overnight at rt. Concentration of the mixture afforded 1-(4-chloro-phenyl)-4-methyl-5-oxo-pyrrolidine-3-carboxylic acid amide LXXIII as light brown solid (420 mg).

To a refluxing solution of LXXIII (420 g, 1.72 mmol) in THF (20 mL) and water (20 mL) was added (diacetoxyiodo) benzene (1.9 g, 5.4 mmol) as one portion. And the mixture was stirred at refluxing for 3 hr. After removal of THF, the remaining aqueous solution was acidified by HCl to pH~2, and washed with EtOAc (15 mL×2). The aqueous phase was separated, concentrated and dried to afford 4-amino-1-(4-chloro-phenyl)-3-methyl-pyrrolidin-2-one hydrochloride salt LXXIV as light brown solid (186 mg, yield 48%).

A mixture of LXXIV (100 mg, 0.38 mmol), 4-iodo-benzoic acid methyl ester LIII (110 mg, 0.42 mmol), cesium carbonate (372 mg, 1.14 mmol), Pd(dba)$_2$ (17 mg, 0.02 mmol) and (3,5-4,5-bis-diphenylphosphanyl-9,9-dimethyl-9H-xanthene (22 mg, 0.04 mmol) in 1,4-dioxane (5 mL) was charged with nitrogen and heated at 110° C. overnight. Then the mixture was filtered and washed with EtOAc; the combined organic phase was concentrated, and the residue was purified by column chromatography (eluate: EtOAc/petroleum ether from 1/3 to 1/2) to afford LXXV as light yellow oil (73 mg, yield 54%).

To a solution of LXXV (73 mg) in MeOH (2 mL) was added hydroxylamine (1 mL, 50% aqueous solution) and KOH (10 mg), and the mixture was heated at 60° C. for 3 hr. The mixture was purified by preparative HPLC to afford Example 78 as white solid (28 mg). MS: calc'd (MH+) 327 exp (MH+) 327. $^1$H NMR (DMSO-d$_6$, 400 MHz), 10.83 (b, 1H), 8.71 (b, 1H), 7.74-7.35 (m, 2.28H), 7.58-7.55 (m, 2.28H), 7.44-7.42 (m, 2.28H), 6.69-6.66 (m, 2.28H), 6.59 (d, 1H, J=7.2 Hz), 6.52 (d, 0.14H, J=7.2 Hz), 4.41-4.39 (m, 0.14H), 4.28-4.24 (m, 1H), 4.16-4.4.31 (m, 0.14H), 3.99-3.92 (m, 1H), 3.64-3.61 (m, 0.14H), 3.51-3.47 (m, 1H), 3.08-3.04 (m, 0.14H), 2.71-2.67 (m, 1H), 1.25 (d, 3H, J=7.2 Hz), 1.07 (d, 0.42H, J=7.6 Hz).

Example 79

N-Hydroxy-4-(1-phenyl-pyrrolidin-3-ylamino)-benzamide

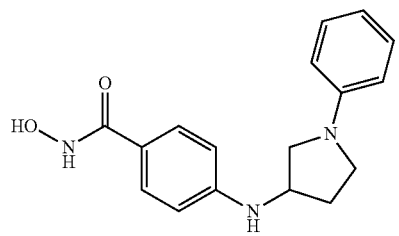 [SMILES: O=C(NO)c1ccc(NC2CCN(c3ccccc3)C2)cc1]

The title compound was prepared according to the general synthesis method shown in Scheme 6. And a detailed synthesis route was provided as shown in Scheme 16.

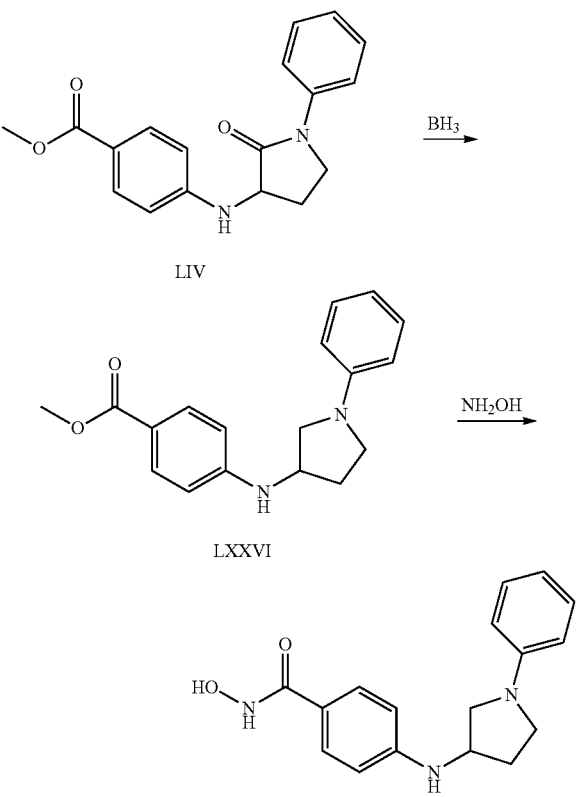

Borane-THF complex (2 mL) was added to a solution of 4-(2-oxo-1-phenyl-pyrrolidin-3-ylamino)-benzoic acid methyl ester LIV (189 mg) in THF (50 mL) and the mixture was refluxed overnight. The solvent was removed and the crude product LXXVI was used in the next step without further purification.

To a solution of LXXVI (crude product) in MeOH (5 mL) was added hydroxylamine (1 mL, 50% aqueous solution) and KOH (20 mg), and the reaction mixture was heated at 60° C. for 3 hr. The product was purified by preparative HPLC to afford Example 79 as white solid (63 mg). MS: calc'd 297 (MH+), exp 297 (MH+). ¹H NMR (d-MeOD, 400 MHz), 7.58-7.61 (m, 2H), 7.19-7.23 (m, 2H), 6.67-6.73 (m, 5H), 4.27-4.29 (m, 1H), 3.70-3.74 (m, 1H), 3.50-3.55 (m, 1H), 3.41-3.45 (m, 1H), 3.24-3.27 (m, 1H), 2.40-2.45 (m, 1H), 2.06-2.11 (m, 1H).

Example 80

4-[1-(4-Chloro-phenyl)-pyrrolidin-3-ylamino]-N-hydroxy-benzamide

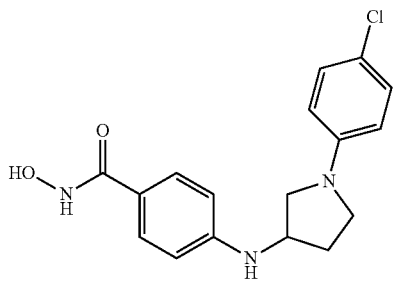 [SMILES: O=C(NO)c1ccc(NC2CCN(c3ccc(Cl)cc3)C2)cc1]

The title compound was prepared in analogy to Example 79 in scheme 16 by using 4-[1-(4-chloro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd (MH+) 332, exp (MH+) 332. ¹H NMR (CD₃OD, 400 MHz), 7.60 (d, 2H, J=9.6 Hz), 7.14 (d, 2H, J=10 Hz), 7.05 (d, 2H, J=9.6 Hz), 6.56 (d, 2H, J=10 Hz), 4.26 (m, 1H), 3.66 (m, 1H), 3.48 (m, 1H), 3.78 (m, 1H), 3.18 (m, 1H), 2.39 (m, 1H), 2.06 (m, 1H).

Example 81

4-[1-(2,6-Dichloro-phenyl)-pyrrolidin-3-ylamino]-N-hydroxy-benzamide

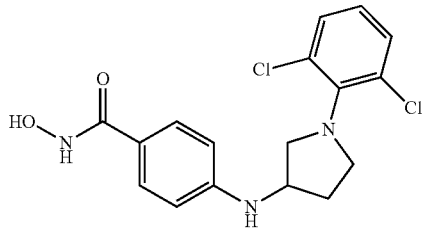 [SMILES: O=C(NO)c1ccc(NC2CCN(c3c(Cl)cccc3Cl)C2)cc1]

The title compound was prepared in analogy to Example 79 in scheme 16 by using 4-[1-(2,6-dichloro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd 365 (MH+), exp 365 (MH+). ¹H NMR (d-DMSO, 400 MHz), 10.78 (s, 1H), 7.55 (d, 2H, J=8.8 Hz), 7.45 (d, 2H, J=8 Hz), 7.22-7.18 (m, 1H), 6.62 (d, 2H, J=8.8 Hz), 4.16-4.19 (m, 1H), 3.54-3.65 (m, 1H), 3.42-3.46 (m, 1H), 3.31-3.37 (m, 1H), 3.11-3.14 (m, 1H), 2.34-2.40 (m, 1H), 1.93-1.95 (m, 1H).

Example 82

4-[1-(2,4-Dichloro-phenyl)-pyrrolidin-3-ylamino]-N-hydroxy-benzamide

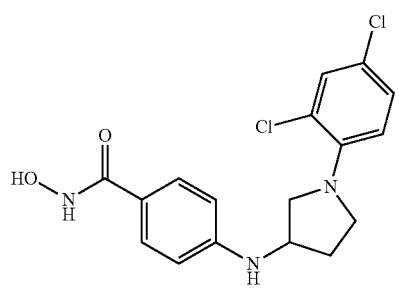 [SMILES: O=C(NO)c1ccc(NC2CCN(c3ccc(Cl)cc3Cl)C2)cc1]

The title compound was prepared in analogy to Example 79 in scheme 16 by using 4-[1-(2,4-dichloro-phenyl)-2-oxo-pyrrolidin-3-ylamino]-benzoic acid methyl ester instead of 4-(2-oxo-1-phenyl-pyrrolidin-3-ylamino)-benzoic acid methyl ester. MS: calc'd 365 (MH+), exp 365 (MH+). ¹H NMR (d-DMSO, 400 MHz), 8.67 (s, 1H), 7.54 (d, 2H, J=8.4 Hz), 7.40 (d, 1H, J=2.8 Hz), 7.24-7.27 (dd, 1H, J=2.8 Hz, J=8.8 Hz), 6.95 (d, 1H, J=8.8 Hz), 6.61 (d, 2H, J=8.8 Hz), 6.42 (d, 1H, J=6.8 Hz), 4.08-4.12 (m, 1H), 3.70-3.74 (m, 1H), 3.47-3.51 (m, 1H), 3.23-3.27 (m, 2H), 2.23-2.33 (m, 1H), 1.87-1.91 (m, 1H).

Example 83

N-Hydroxy-4-(1-pyrimidin-2-yl-pyrrolidin-3-ylamino)-benzamide

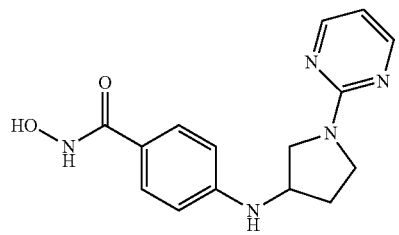 [SMILES: O=C(NO)c1ccc(NC2CCN(c3ncccn3)C2)cc1]

The detailed synthesis route of title compound was provided in Scheme 17.

scheme 17 (Ex. 83)

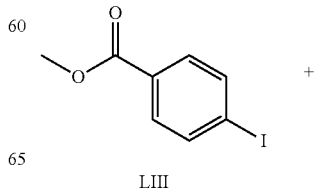

LIII

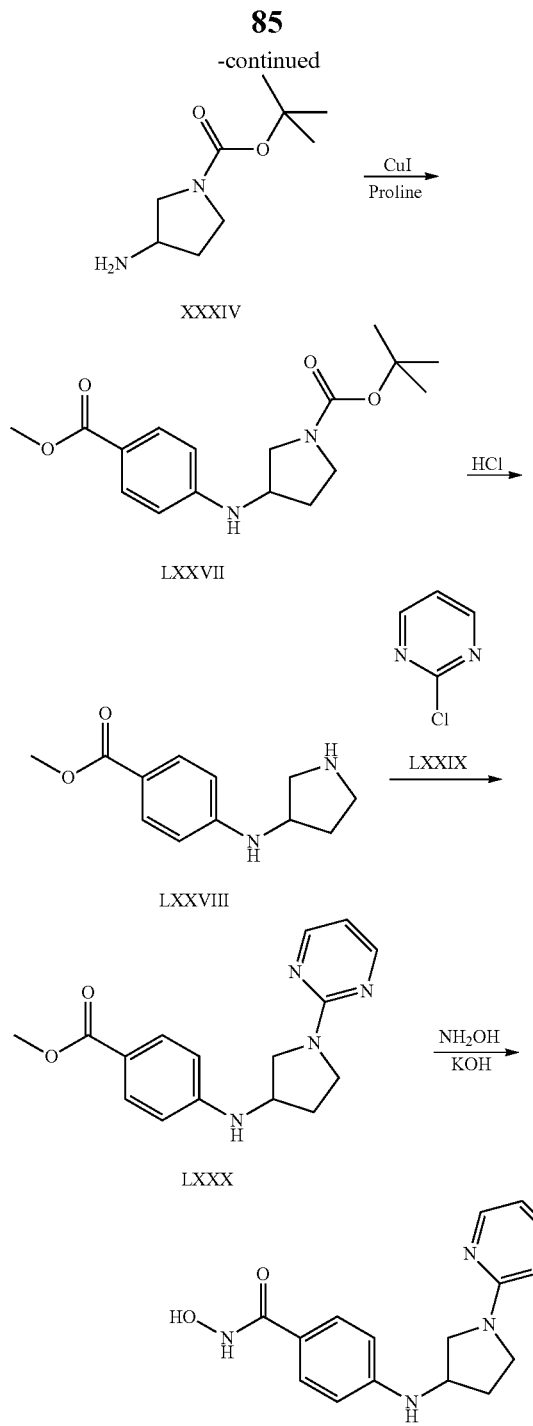

hr. The solvent was removed and the residue was dissolved in DMF (5 mL) and DIPEA (1 mL). LXXIX was added into the solution and the mixture was stirred at 110° C. overnight. The mixture was partitioned between water and EtOAc. The organic phase was dried and concentrated. The residue was purified by silica gel column to afford white solid LXXX (126 mg, 0.43 mmol).

To a solution of 4-(1-pyrimidin-2-yl-pyrrolidin-3-ylamino)-benzoic acid methyl ester LXXX (244 mg, 0.82 mmol) in MeOH (2 mL) was added hydroxylamine (1 mL, 50% aqueous solution) and KOH (10 mg). The reaction mixture was heated at 60° C. for 3 hr. Purification by preparative HPLC afforded Example 83 as white solid (29 mg, 0.1 mmol). MS: calc'd 299 (MH$^+$), exp 299 (MH$^+$). $^1$H NMR (d-MeOD, 400 MHz), 8.33 (d, 2H, J=4.8 Hz), 7.57-7.61 (m, 2H), 6.69-6.71 (m, 2H,) 6.60-6.63 (m, 1H), 4.24-4.27 (m, 1H), 3.88-3.93 (m, 1H), 3.69-3.75 (m, 2H), 3.51-3.55 (m, 1H), 2.35-2.39 (m, 1H), 2.08-2.11 (m, 1H).

Example 84

4-(1-Benzenesulfonyl-pyrrolidin-3-ylamino)-N-hydroxy-benzamide

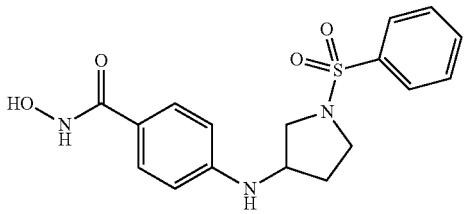 [SMILES: O=C(NO)c1ccc(NC2CCN(S(=O)(=O)c3ccccc3)C2)cc1]

The title compound was prepared according to the synthesis method shown in Scheme 7. And a detailed synthesis route was provided as shown in Scheme 18.

scheme 18 (Ex. 84)

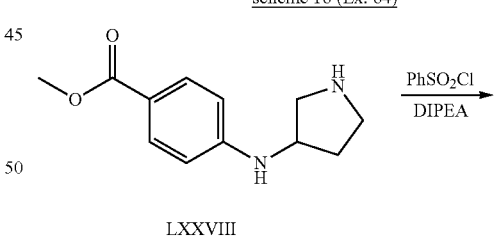

The mixture of 4-iodo-benzoic acid methyl ester LIII (524 mg, 2 mmol), 3-amino-pyrrolidine-1-carboxylic acid tert-butyl ester XXXIV (409 mg, 2.2 mmol), CuI (38 mg, 0.2 mmol), proline (46 mg, 0.4 mmol) and K$_2$CO$_3$ (552 mg, 4.0 mmol) in DMF (10 mL) was stirred at 110° C. overnight under nitrogen atmosphere. After LC-MS indicated that the reaction was completed, the mixture was partitioned between water and EtOAc. The organic phase was dried and concentrated. The residue was purified by silica gel column chromatography to afford white solid LXXVII (339 mg, 1.1 mmol).

3-(4-Methoxycarbonyl-phenylamino)-pyrrolidine-1-carboxylic acid tert-butyl ester LXXVII (339 mg, 1.1 mmol) was stirred in a solution of hydrochloride in MeOH (5 mL) for 2

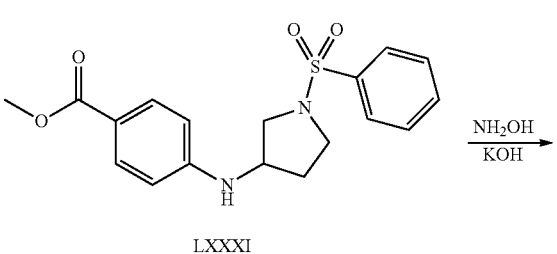

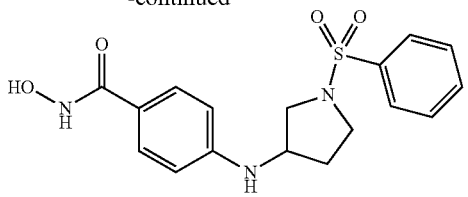

To a solution of LXXVIII (crude product) in CH$_2$Cl$_2$ (10 mL) was added benzenesulfonyl chloride (194 mg, 1.1 mmol) and DIPEA (0.5 mL), and the reaction mixture was stirred at rt for 2 hr. After solvent removal, the crude product LXXXI was dissolved in 3 mL of MeOH. To the MeOH solution was added 1 mL of 50% aqueous NH$_2$OH and KOH (150 mg), and the reaction mixture was stirred at rt for 1 h. Purification by preparative HPLC gave the title compound Example 84. MS: calc'd (MH+) 362 exp (MH+) 362. $^1$H NMR (MeOD, 400 MHz), 7.79-7.83 (m, 2H), 7.76-7.78 (m, 3H), 7.71-7.73 (m, 2H), 7.14-7.15 (d, 2H, J=4 Hz), 3.71-3.74 (m, 1H), 3.35-3.37 (m, 1H), 3.22-3.24 (m, 3H), 2.17-2.24 (m, 1H), 1.73-1.78 (m, 1H).

Example 85

4-[1-(4-Fluoro-benzenesulfonyl)-pyrrolidin-3-ylamino]-N-hydroxy-benzamide

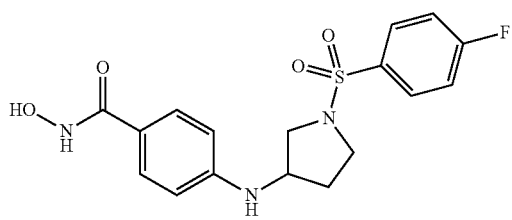 [SMILES: O=C(NO)c1ccc(NC2CCN(S(=O)(=O)c3ccc(F)cc3)C2)cc1]

The title compound was prepared in analogy to Example 84 in Scheme 18 by using 4-fluorobenzenesulfonyl chloride instead of benzenesulfonyl chloride. MS: calc'd (MH+) 380 exp (MH+) 380. $^1$H NMR (MeOD, 400 MHz), 7.83-7.84 (d, 2H, J=2 Hz), 7.54-7.57 (m, 2H), 7.24-7.28 (m, 2H), 6.46-6.49 (m, 2H), 3.97-3.99 (m, 1H), 3.50-3.54 (m, 1H), 3.40-3.45 (m, 2H), 3.22-3.25 (m, 1H), 2.16-2.22 (m, 1H), 1.81-1.88 (m, 1H).

Example 86

4-[1-(4-Chloro-benzenesulfonyl)-pyrrolidin-3-ylamino]-N-hydroxy-benzamide

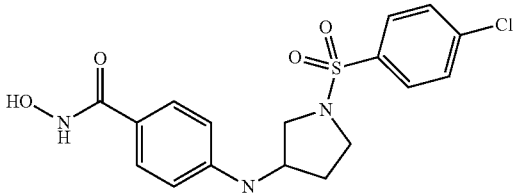

The title compound was prepared in analogy to Example 84 in Scheme 18 by using 4-chlorobenzenesulfonyl chloride instead of benzenesulfonyl chloride. MS: calc'd (MH+) 396 exp (MH+) 396. $^1$H NMR (MeOD, 400 MHz), 7.72-7.77 (m, 4H), 7.62-7.64 (d, 2H, J=8.8 Hz), 7.16-7.18 (d, 2H, J=6 Hz), 3.62-3.66 (m, 1H), 3.26-3.29 (m, 2H), 3.13-3.15 (m, 1H), 2.95-2.98 (m, 1H), 2.13-2.17 (m, 1H), 1.81-1.84 (m, 1H).

Example 87

4-[1-(Biphenyl-4-sulfonyl)-pyrrolidin-3-ylamino]-N-hydroxy-benzamide

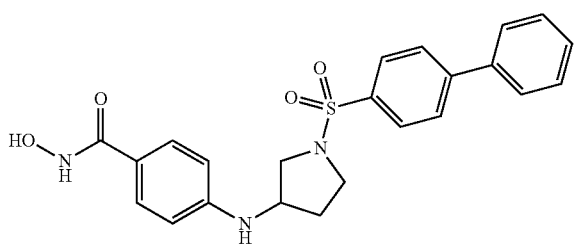 [SMILES: O=C(NO)c1ccc(NC2CCN(S(=O)(=O)c3ccc(-c4ccccc4)cc3)C2)cc1]

The title compound was prepared in analogy to Example 84 in Scheme 18 by using biphenyl-4-sulfonyl chloride instead of benzenesulfonyl chloride. MS: calc'd (MH+) 438 exp (MH+) 438. $^1$H NMR (MeOD, 400 MHz), 7.76-7.78 (d, 1H, J=7.6 Hz), 7.72-7.74 (d, 1H, J=7.2 Hz), 7.68-7.03 (m, 4H), 7.60-7.62 (d, 2H, J=6.8 Hz), 7.50-7.52 (m, 2H), 7.41-7.44 (m, 1H), 7.17-7.21 (m, 2H), 3.62-3.65 (m, 1H), 3.28-3.31 (m, 2H), 3.12-3.15 (m, 2H), 2.92-2.98 (m, 1H), 2.15-2.20 (m, 1H), 1.81-1.89 (m, 1H).

Example 88

4-(1-Benzoyl-pyrrolidin-3-ylamino)-N-hydroxy-benzamide

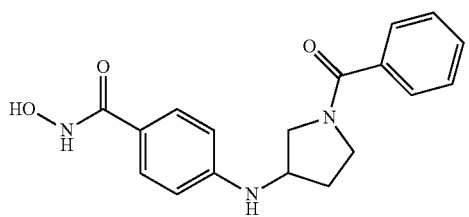 [SMILES: O=C(NO)c1ccc(NC2CCN(C(=O)c3ccccc3)C2)cc1]

The title compound was prepared according to the general synthesis method shown in Scheme 8. And a detailed synthesis route was provided as shown in Scheme 19.

Scheme 19 (Ex. 88)

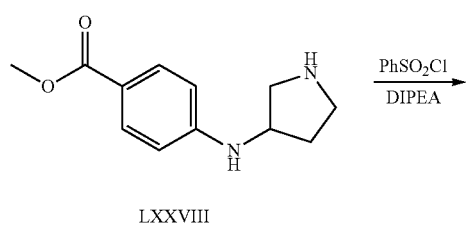

LXXVIII

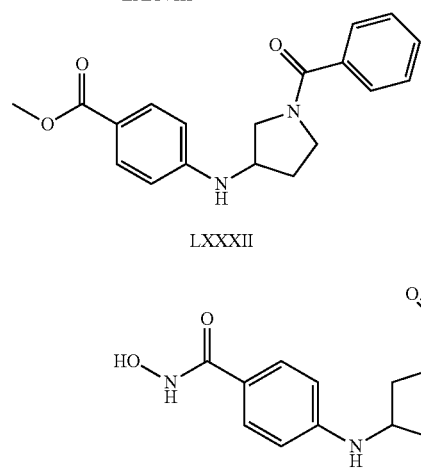

To a solution of LXXVIII (220 mg, 1 mmol) in CH$_2$Cl$_2$ (5 mL) was added benzoyl chloride (154 mg, 1.1 mmol) and DIPEA (0.5 mL), and the reaction mixture was stirred at rt for 2 hr. After solvent removal, the crude product DOOM was dissolved in 3 mL of MeOH. To this solution was added 1 mL of 50% aqueous NH$_2$OH and KOH (150 mg), and the reaction mixture was stirred at rt for 1 hr. Purification by preparative HPLC gave the title compound Example 88. MS: calc'd (MH+) 326 exp (MH+) 326. $^1$H NMR (MeOD, 400 MHz), 7.66-7.68 (d, 2H, J=8.4 Hz), 7.38-7.39 (m, 4H), 7.17-7.28 (m, 3H), 3.75-3.80 (m, 1H), 3.55-3.60 (m, 1H), 3.43-3.47 (m, 1H), 3.25-3.30 (m, 1H), 3.13-3.15 (m, 1H), 2.29-2.31 (m, 1H), 2.05-2.08 (m, 1H).

Example 89

4-[1-(4-Fluoro-benzoyl)-pyrrolidin-3-ylamino]-N-hydroxy-benzamide

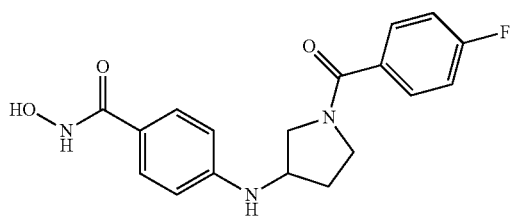 [SMILES: O=C(NO)c1ccc(NC2CCN(C(=O)c3ccc(F)cc3)C2)cc1]

The title compound was prepared in analogy to Example 88 in Scheme 19 by using 4-fluorobenzoyl chloride instead of benzoyl chloride. MS: calc'd (MH+) 344 exp (MH+) 344. $^1$H NMR (MeOD, 400 MHz), 7.53-7.63 (m, 4H), 3.15-3.24 (m, 2H), 6.71-6.73 (d, 2H, J=8.8 Hz), 6.61-6.63 (d, 2H, J=8.8 Hz), 7.38-7.39 (m, 4H), 7.17-7.28 (m, 3H), 4.14-4.18 (m, 1H), 3.82-3.87 (s, 3H), 3.76-3.80 (m, 1H), 3.68-3.74 (m, 1H), 3.54-3.65 (m, 1H), 3.31-3.37 (m, 1H), 2.26-2.28 (m, 1H), 2.01-2.04 (m, 1H).

Example 90

N-Hydroxy-4-[1-(4-methoxy-benzoyl)-pyrrolidin-3-ylamino]-benzamide

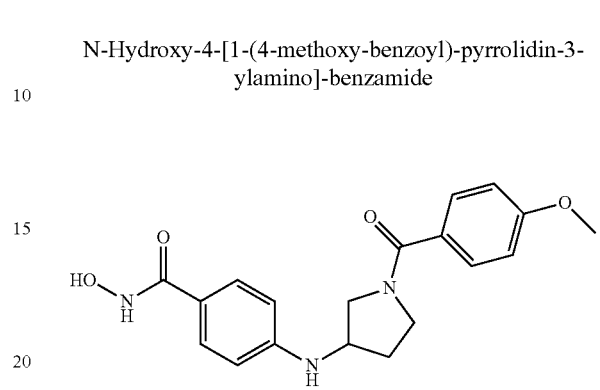

The title compound was prepared in analogy to Example 88 in Scheme 19 by using 4-methoxybenzoyl chloride instead of benzoyl chloride. MS: calc'd (MH+) 356 exp (MH+) 356. $^1$H NMR (MeOD, 400 MHz), 7.53-7.63 (m, 4H), 3.15-3.24 (m, 2H), 6.71-6.73 (d, 2H, J=8.8 Hz), 6.61-6.63 (d, 2H, J=8.8 Hz), 7.38-7.39 (m, 4H), 7.17-7.28 (m, 3H), 4.13-4.20 (m, 1H), 3.78-3.81 (m, 1H), 3.68-3.74 (m, 1H), 3.55-3.63 (m, 1H), 3.32-3.39 (m, 1H), 2.25-2.27 (m, 1H), 2.00-2.05 (m, 1H).

Example 91

4-(1-Benzyl-3-methyl-2-oxo-2,3-dihydro-1H-indol-3-ylamino)-N-hydroxy-benzamide

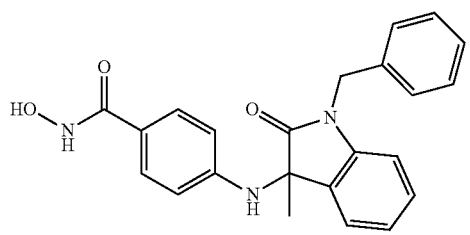 [SMILES: CC1(Nc2ccc(C(=O)NO)cc2)C(=O)N(Cc2ccccc2)c2ccccc21]

The title compound was prepared according to the general synthesis method shown in Scheme 9. A detailed synthesis route is provided in Scheme 20.

Scheme 20 (Ex. 91)

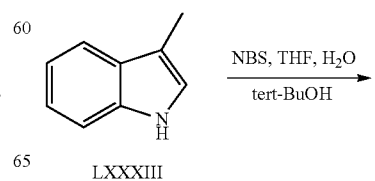

LXXXIII

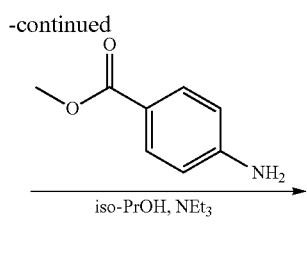

LXXXIV

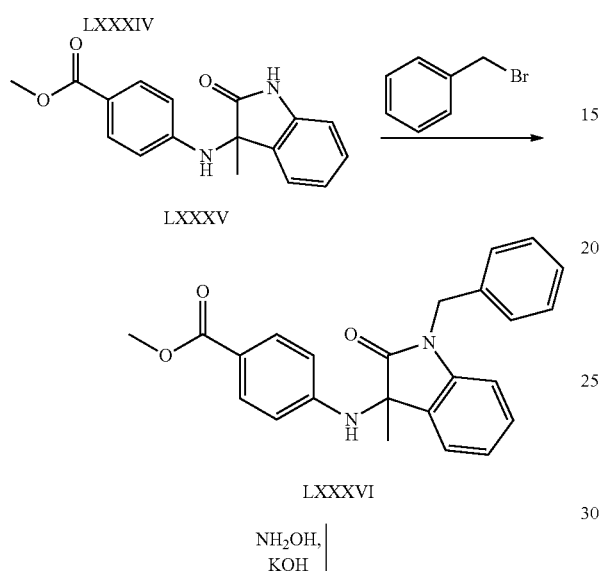

N-Bromosuccinimide (NBS) (5.42 g, 30.49 mmol) was dissolved in cold THF (100 mL) The resulting THF solution was then added dropwise via addition funnel to a stirring solution of 3-methylindole LXXXIII (2.00 g, 15.25 mmol) in mixed t-BuOH (100 mL) and H₂O (1 mL) at rt over a period of one hour. After stirred for an additional hour, the solution was concentrated under reduced pressure and the crude material was directly purified by silica gel column chromatography (EtOAc-hexanes 1:4) to give 3-bromo-3-methyl-2-indolinone as a pale yellow solid 3-bromo-3-methyl-2-indolinone LXXXIV (2.52 g, 73%).

To a solution of LXXXIV (2.5 g, 11.1 mmol), and NEt₃ (5 ml) in isopropanol (15 ml) was added 4-amino-benzoic methyl ester (1.68 g, 11.1 mmol) at rt under nitrogen. The reaction mixture was stirred at rt for 3 h. The solution was concentrated under reduced pressure and the crude material was directly purified by silica gel column chromatography to give 4-(3-methyl-2-oxo-2,3-dihydro-1H-indol-3-ylamino)-benzoic methyl ester LXXXV (2.68 g, 82%).

To a solution of LXXXV (148 mg, 0.5 mmol) in DMF (5 ml) was added benzyl bromide (85 mg, 0.5 mmol) and K₂CO₃ (1 mmol). The mixture was stirred at rt for 3 hr. The solvent was removed to give crude product LXXXVI which was directly used in next step without purification.

The mixture of LXXXVI, 50% aqueous NH₂OH (1 mL) and KOH (150 mg) in MeOH (2 mL) was stirred at rt for 1 hr. The reaction solution was purified by preparative HPLC to give target compound Example 91. MS: calc'd (MH+) 388.1, exp (MH+) 388.1. ¹H NMR (DMSO-d6, 400 MHz), 10.69 (s, 1H), 8.69 (s, 1H), 7.34 (m, 4H), 7.30 (s, 1H), 7.25 (m, 4H), 7.09 (m, 3H), 6.07 (d, 2H, J=8.8 Hz), 5.04 (q, 2H), 1.57 (s, 3H).

Example 92

4-[1-2-chloro-benzyl)-3-methyl-2-oxo-2,3-dihydro-1H-indol-3-ylamino)-N-hydroxy-benzamide

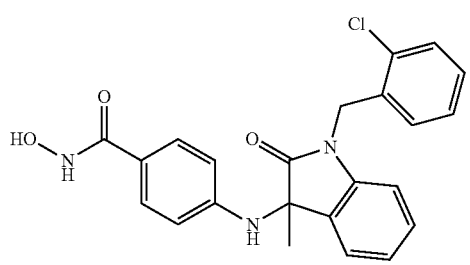 [SMILES: CC1(Nc2ccc(C(=O)NO)cc2)C(=O)N(Cc2ccccc2Cl)c2ccccc21]

The title compound was prepared in analogy to Example 91 in Scheme 20 by using 1-bromomethyl-2-chloro-benzene instead of benzyl bromide. MS: calc'd (MH+) 422.2, exp (MH+) 422.2. ¹H NMR (DMSO-d6, 400 MHz), 10.71 (s, 1H), 7.56 (m, 1H), 7.36 (m, 4H), 7.23 (m, 2H), 7.22 (m, 1H), 7.06 (m, 2H), 6.98 (d, 1H, 7.6 Hz), 6.15 (d, 2H, J=8.8 Hz), 5.09 (q, 2H), 1.57 (s, 3H).

Example 93

4-[1-(3-chloro-benzyl)-3-methyl-2-oxo-2,3-dihydro-1H-indol-3-ylamino)-N-hydroxy-benzamide

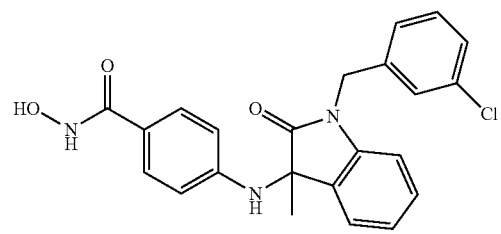 [SMILES: CC1(Nc2ccc(C(=O)NO)cc2)C(=O)N(Cc2cccc(Cl)c2)c2ccccc21]

The title compound was prepared in analogy to Example 91 in Scheme 20 by using 1-bromomethyl-3-chloro-benzene instead of benzyl bromide. MS: calc'd (MH+) 422.2, exp (MH+) 422.2. ¹H NMR (DMSO-d6, 400 MHz), 10.68 (s, 1H), 8.68 (s, 1H), 7.48 (s, 1H), 7.40 (m, 2H), 7.34 (m, 1H), 7.26 (m, 4H), 7.14 (d, 1H, J=7.6 Hz), 7.05 (m, 2H), 6.05 (d, 2H, J=8.8 Hz), 5.09 (q, 2H), 1.57 (s, 3H).

Example 94

N-hydroxy-4-(3-methyl-2-oxo-1-phenethyl-2,3-dihydro-1H-indol-3-ylamino)-benzamide

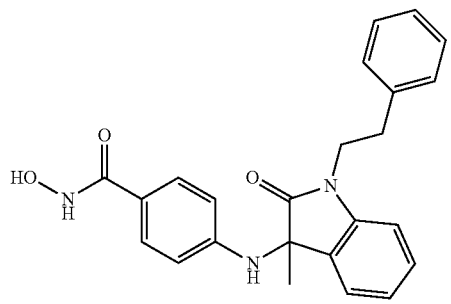 [SMILES: CC1(Nc2ccc(C(=O)NO)cc2)C(=O)N(CCc2ccccc2)c2ccccc21]

The title compound was prepared in analogy to Example 91 in Scheme 20 by using (2-bromo-ethyl)-benzene instead of benzyl bromide. MS: calc'd (MH+) 402.1, exp (MH+) 402.1. $^1$H NMR (DMSO-d6, 400 MHz), 10.68 (s, 1H), 7.24 (m, 7H), 7.20 (m, 3H), 7.01 (m, 2H), 6.05 (d, 2H, J=8.8 Hz), 4.02 (m, 2H), 3.02 (m, 2H), 1.57 (s, 3H).

Example 95

N-hydroxy-4-(3-methyl-2-oxo-1-phenyl-2,3-dihydro-1H-indol-3-ylamino)-benzamide

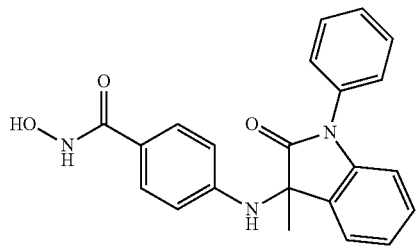 [SMILES: CC1(Nc2ccc(C(=O)NO)cc2)C(=O)N(c2ccccc2)c2ccccc21]

The title compound was prepared according to the synthesis method shown in Scheme 9. And a detailed synthesis route was provided as shown in Scheme 21.

Scheme 21

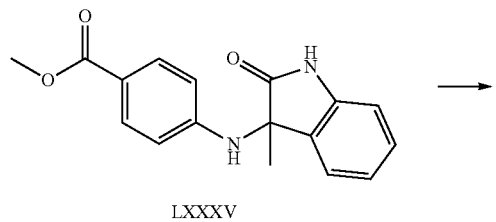

LXXXV

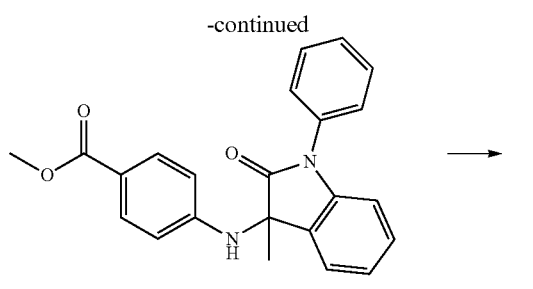

LXXXVII

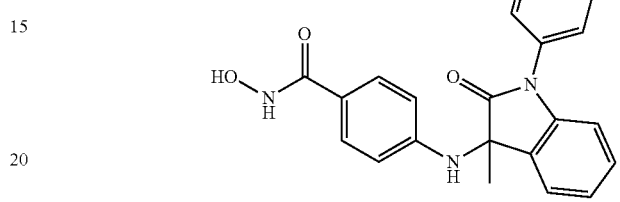

Example 95

To a solution of 4-(3-methyl-2-oxo-2,3-dihydro-1H-indol-3-ylamino)-benzoic methyl ester LXXXV (148 mg, 0.5 mmol) in dioxane (5 ml) was added iodobenzene (102 mg, 0.5 mmol), $K_2CO_3$ (138 mg, 1 mmol), CuI (9.5 mg, 0.05 mmol, 10%) and N,N'-dimethyl-cyclohexane-1,2-diamine (14.2, 0.1 mmol, 20%). The reaction mixture was stirred at 100° C. overnight under nitrogen before diluted with water and extracted with EtOAc. The combined organic phase was dried and concentrated to crude product 4-(3-methyl-2-oxo-1-phenyl-2,3-dihydro-1H-indol-3-ylamino)-benzoic acid methyl ester LXXXVII which was directly used to next step without purification.

The mixture of LXXXVII, 50% aqueous $NH_2OH$ (1 mL) and KOH (150 mg) in MeOH (2 mL) was stirred at rt for 1 hr. The reaction solution was purified by preparative HPLC to give target compound Example 95. MS: calc'd (MH+) 374.2, exp (MH+) 374.2. $^1$H NMR (DMSO-d6, 400 MHz), 10.72 (s, 1H), 7.62 (m, 2H), 7.50 (m, 3H), 7.40 (d, 2H, J=8.8 Hz), 7.30 (m, 2H), 7.12 (m, 2H), 6.99 (s, 1H), 6.24 (d, 2H, J=8.8 Hz), 1.57 (s, 3H).

Example 96

4-[1-(3-chloro-phenyl)-3-methyl-2-oxo-2,3-dihydro-1H-indol-3-ylamino)-N-hydroxy-benzamide

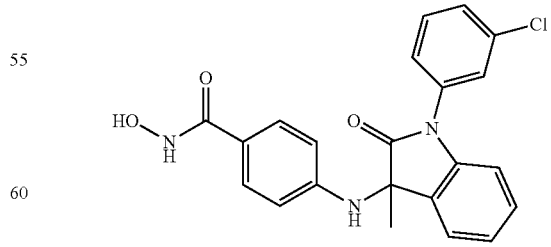

The title compound was prepared in analogy to Example 95 in Scheme 21 by using 1-chloro-3-iodo-benzene instead of iodobenzene. MS: calc'd (MH+) 408.2, exp (MH+) 408.2. $^1$H NMR (DMSO-d6, 400 MHz), 10.72 (s, 1H), 7.65 (m, 2H), 7.50 (d, 1H, J=7.6 Hz), 7.40 (d, 2H, J=8.8 Hz), 7.30 (m, 2H), 7.12 (m, 2H), 6.93 (d, 1H, J=7.6 Hz), 6.24 (d, 2H, J=8.8 Hz), 1.67 (s, 3H).

Example 97

4-[1-(4-Chloro-phenyl)-5-fluoro-3-methyl-2-oxo-2,3-dihydro-1H-indol-3-ylamino]-N-hydroxy-benzamide

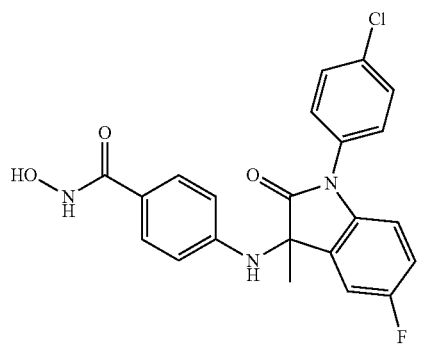 [SMILES: CC1(Nc2ccc(C(=O)NO)cc2)C(=O)N(c2ccc(Cl)cc2)c2ccc(F)cc21]

The title compound was prepared according to the general synthesis method shown in Scheme 10. A detailed synthesis route is provided in Scheme 22.

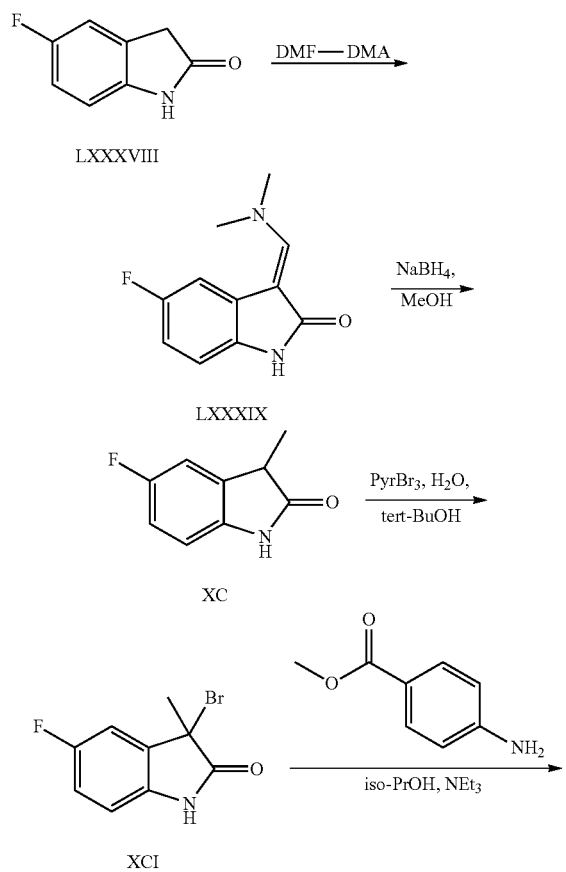

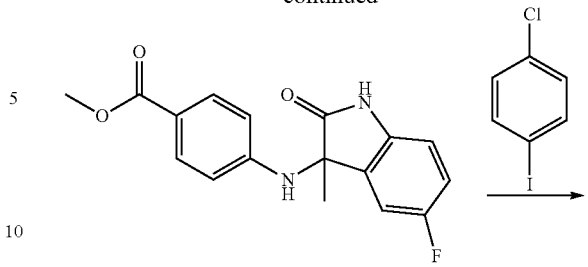

XCII

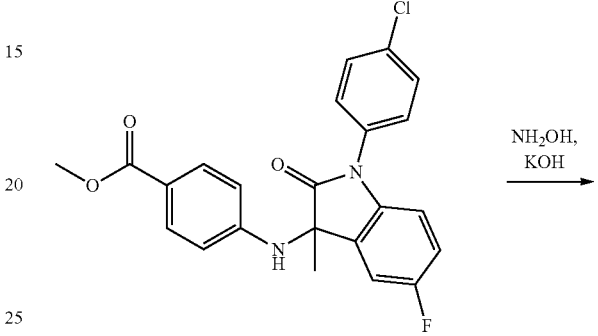

XCIII

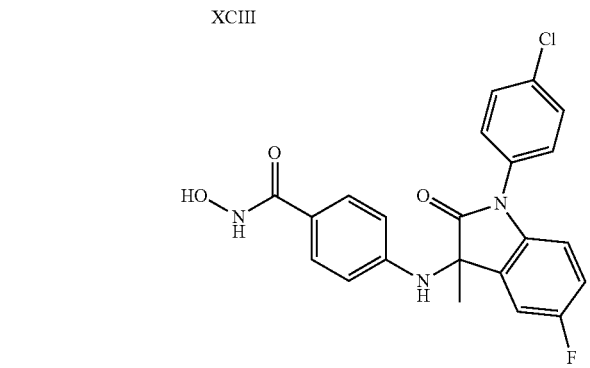

DMF-DMA (3.15 g, 26.4 mmol) was added into a solution of 5-fluoroindolin-2-one LXXXVIII (2.0 g, 13.2 mmol) in dry THF. The reaction mixture was stirred at rt for 4 hr before being poured into water and extracted by EtOAc. The organic layer was separated and dried by Na₂SO₄, and concentrated to give (E)-3-((dimethylamino)methylene)-5-fluoroindolin-2-one LXXXVIX.

To a solution of LXXXVIX (1.0 g, 4.8 mmol) in MeOH was added NaBH₄ (363 mg, 9.6 mmol) at 0° C. The reaction mixture was stirred at rt for 3 hr before being neutralized to pH 7 with 1N HCl and extracted with EtOAc. The organic layer was separated, dried by Na₂SO₄, and concentrated. The residue was purified by column chromatography to give 5-fluoro-3-methylindolin-2-one XC.

Pyridinium tribromide (3.83 g, 12 mmol) was added into a solution of XC (1.65 g, 10 mmol) in a mixed solvent of tert-BuOH and H₂O (volume ratio, 1:1). The reaction mixture was stirred at rt for 2 hr before water and EtOAc were added. The organic layer was collected, dried over Na₂SO₄, and concentrated to give the crude product 3-bromo-5-fluoro-3-methylindolin-2-one XCI, which was used in next step without further purification.

Et₃N (1.21 g, 12 mmol) was added into a solution of methyl 4-aminobenzoate (1.81 g, 12 mmol) and XCI (2.44 g, 10 mmol) in DMF. After stirred at rt for 2 hr, the mixture was poured into water and extracted with EtOAc. The organic layer was separated, dried over Na$_2$SO$_4$, and concentrated in vacuo. The residue was purified by column chromatography to give methyl 4-(5-fluoro-3-methyl-2-oxoindolin-3-ylamino)benzoate XCII.

CuI (30.5 mg, 0.16 mmol), (1R,2R)—N,N-dimethyl-cyclohexane-1,2-diamine (45.5 mg, 0.32 mmol) and K$_2$CO$_3$ (442.3 mg, 3.2 mmol) was added into a solution of XCII (500 mg, 1.6 mmol) and 1-chloro-4-iodo-benzene (458 mg, 1.92 mmol) in DMF. After stirred at 90° C. overnight, the mixture was poured into water and extracted with EtOAc. The organic layer was separated, dried over Na$_2$SO$_4$, and concentrated in vacuo. The residue was purified by column chromatography to give product 4-[1-(4-chloro-phenyl)-5-fluoro-3-methyl-2-oxo-2,3-dihydro-1H-indol-3-ylamino]-benzoic acid methyl ester XCIII.

To a solution of XCIII (424 mg, 1.0 mmol) in MeOH was added hydroxylamine (2 mL, 50% aqueous solution) and KOH (15 mg). The reaction mixture was stirred at rt for 3 hr before being purified by preparative HPLC to afford Example 97 as solid. MS: calc'd (MH$^+$) 426, exp (MH$^+$) 426. $^1$H NMR (CD3OD-d4, 400 MHz), 7.63 (d, 2H, J=8.8 Hz), 7.50-7.44 (m, 4H), 7.17-7.15 (m, 1H), 7.11-7.06 (m, 1H), 6.97-6.93 (m, 1H), 6.33 (d, 2H, J=8.8 Hz), 1.75 (s, 3H).

Example 98

4-[1-(3-Chloro-phenyl)-5-fluoro-3-methyl-2-oxo-2,3-dihydro-1H-indol-3-ylamino]-N-hydroxy-benzamide

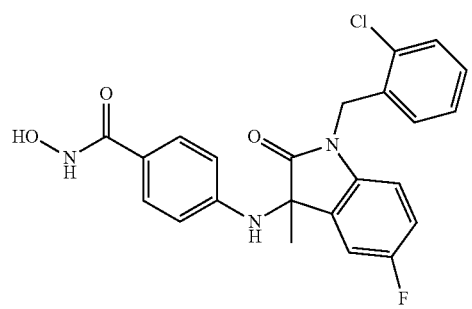 [SMILES: CC1(Nc2ccc(C(=O)NO)cc2)C(=O)N(Cc2ccccc2Cl)c2ccc(F)cc21]

The title compound was prepared in analogy to Example 97 in Scheme 22 by using 1-chloro-3-iodo-benzene instead of 1-chloro-4-iodo-benzene. MS: calc'd (MH$^+$) 426, exp (MH$^+$) 426. $^1$H NMR (CD3OD-d4, 400 MHz), 7.54-7.53 (m, 1H), 7.53 (s, 2H), 7.46 (d, 3H, J=8.8 Hz), 7.17 (dd, 1H, J=8.0 Hz), 7.13-7.08 (m, 1H), 6.99-6.96 (m, 1H), 6.33 (d, 2H, J=8.8 Hz), 1.76 (s, 3H).

Example 99

4-[1-(2-Chloro-benzyl)-5-fluoro-3-methyl-2-oxo-2,3-dihydro-1H-indol-3-ylamino]-N-hydroxy-benzamide The title compound was prepared according to the general synthesis method shown in Scheme 10. A detailed synthesis route is provided in Scheme 23.

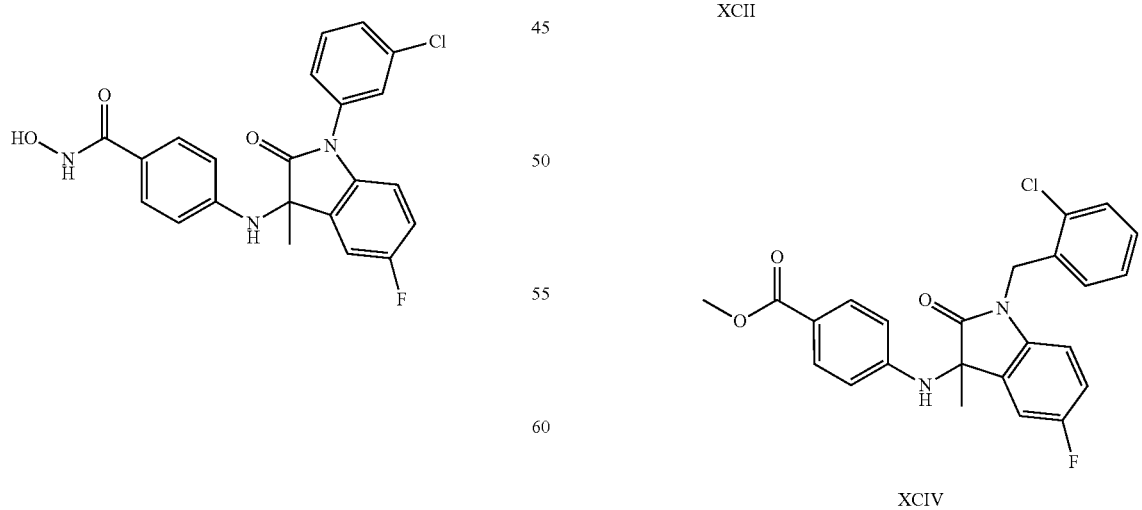

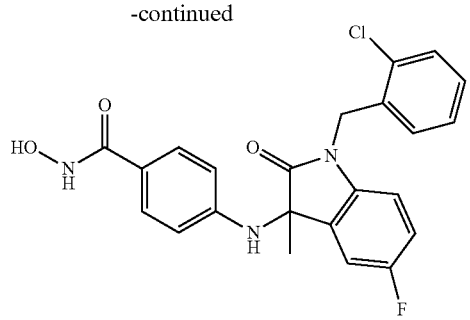

K$_2$CO$_3$ (442.3 mg, 3.2 mmol) was added into a solution of 4-(5-Fluoro-3-methyl-2-oxo-2,3-dihydro-1H-indol-3-ylamino)-benzoic acid methyl ester XCII (500 mg, 1.6 mmol) and 1-bromomethyl-2-chloro-benzene (329 mg, 1.6 mmol) in DMF. After stirred at rt for 2 hr, the reaction mixture was poured into water and extracted with EtOAc. The organic layer was separated, dried over Na$_2$SO$_4$, and concentrated in vacuo. The residue was purified by column chromatography to give 4-[1-(2-chloro-benzyl)-5-fluoro-3-methyl-2-oxo-2,3-dihydro-1H-indol-3-ylamino]-benzoic acid methyl ester XCIII.

To a solution of XCIII (438 mg, 1.0 mmol) in MeOH was added hydroxylamine (2 mL, 50% aqueous solution) and KOH (15 mg). The reaction mixture was stirred at rt for 3 hr before purification by preparative HPLC to afford Example 99 as solid. MS: calc'd (MH$^+$) 440, exp (MH$^+$) 440. $^1$H NMR (CD3OD-d4, 400 MHz), 7.50 (s, 1H), 7.34-7.26 (m, 5H), 7.11-7.01 (m, 2H), 6.97-6.94 (m, 1H), 6.24 (d, 2H, J=8.8 Hz), 5.21 (d, 1H, J=16.4 Hz), 5.11 (d, 2H, J=16.4 Hz), 1.70 (s, 3H).

Example 100

4-[1-(3-Chloro-phenyl)-3-methyl-2-oxo-2,3-dihydro-1H-pyrrolo[3,2-c]pyridin-3-ylamino]-N-hydroxy-benzamide

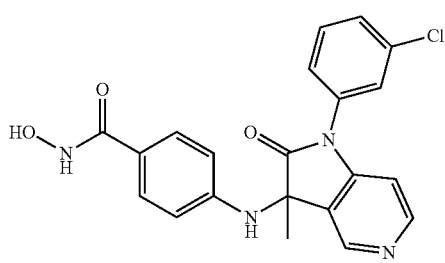 [SMILES: CC1(Nc2ccc(C(=O)NO)cc2)C(=O)N(c2cccc(Cl)c2)c2ccncc21]

The title compound was prepared in analogy to Example 97 in Scheme 22 by using 1,3-dihydro-pyrrolo[3,2-c]pyridin-2-one instead of 5-fluoro-1,3-dihydro-indol-2-one in the condensation reaction, and 1-chloro-3-iodo-benzene instead of 1-chloro-4-iodo-benzene in the copper catalyzed coupling reaction. MS: calc'd (MH$^+$) 409, exp (MH$^+$) 409. $^1$H NMR (CD3OD-d4, 400 MHz), 8.7-8.66 (m, 2H), 7.71-7.65 (m, 3H), 7.51 (d, 2H, J=8.8 Hz), 7.45 (d, 2H, J=6.4 Hz), 6.34 (d, 2H, J=8.8 Hz, 1.91 (s, 3H).

Example 101

Biological Activities

The compounds of the present invention demonstrated sub-micromolar to micromolar inhibition of HDAC6 or HDAC8 based on their in-cell tubulin acetylation activity and enzymatic inhibition of HDAC8. Compounds from the present invention are able to induce obvious NB cell differentiation. Compounds from the present invention also demonstrate synergy when combined with bortezomib in cell growth inhibition of MM cell lines.

HDAC8 Inhibition by Novel Compounds: Recombinant HDAC8 Fluorometric Assay.

A competitive inhibitory assay of HDAC8 was carried out by using recombinant HDAC8 and a commercial substrate Ac-Arg-His-Lys-Lys(ε-acetyl)-AMC. Examples in Table 1 of this invention demonstrated HDAC8 inhibitory activities with IC$_{50}$ values in the range of 0.2 μM to 3 μM as shown in Table 1.

Compounds were tested for their ability to inhibit histone deacetylase 8 using an in vitro deacetylation assay. The enzyme source for this assay was recombinant human HDAC8 protein expressed and purified from insect cells. The HDAC8 enzyme activity was validated by comparing with commercial HDAC8 (Cayman Chemical). The substrate consisted of a commercial product Ac-Arg-His-Lys-Lys(ε-acetyl)-AMC (substrate is available from Cayman Chemical). Using the substrate concentration at the K$_m$ for the HDAC8 enzyme, the deacetylation assay was performed in the presence of novel compounds from 0.01-30 μM using half-log dilutions. In a detailed procedure, 8 μl of HDAC8 enzyme solution (0.125 μg/μl) was transferred to assay plates (CORNING 3676). 1 μl of half-log diluted compounds were added into wells and incubated for 15 min at rt. After that, 8 μl of substrate solution was transferred to the wells and incubated for 30 min at rt. After deacetylation of the substrate by incubation with HDAC8 enzyme, subsequent exposure to a developing reagent produced a fluorophore that was directly proportional to the level of deacetylation. So 4 μl of developer regent (Cayman 10006394) was added into the wells in the assay plates and incubated for 15 min. The fluorescence signal was measured by a FlexStation3 plate reader (excitation wave length 340-360 nm; emission wave length 440-465 nm). The HDAC8 IC$_{50}$ was calculated after normalization and curve fitting using XLfit4.0 software. Inhibition %=[Mean (top)−signal(sample)]×100/[Mean(top)−Mean(bottom)].

TABLE 1

| HDAC8 inhibition by novel compounds: recombinant HDAC8 fluorometric assay. ||
|---|---|
| Example # | HDAC8 IC$_{50}$ (μM) |
| 1 | 0.81 |
| 2 | 0.84 |
| 3 | 1.09 |
| 4 | 0.89 |
| 5 | 0.37 |
| 6 | 0.72 |
| 7 | 0.55 |
| 8 | 0.59 |
| 9 | 1.30 |
| 10 | 1.80 |
| 11 | 2.23 |
| 12 | 0.99 |
| 13 | 0.74 |
| 14 | 3.18 |
| 16 | 1.87 |
| 17 | 1.19 |
| 18 | 1.62 |
| 19 | 1.05 |
| 20 | 1.21 |
| 21 | 1.01 |
| 22 | 1.93 |

TABLE 1-continued

HDAC8 inhibition by novel compounds:
recombinant HDAC8 fluorometric assay.

| Example # | HDAC8 IC$_{50}$ (μM) |
|---|---|
| 23 | 1.41 |
| 24 | 0.77 |
| 25 | 0.97 |
| 26 | 4.69 |
| 27 | 0.75 |
| 28 | 1.86 |
| 29 | 0.75 |
| 30 | 3.21 |
| 31 | 4.14 |
| 32 | 0.71 |
| 33 | 0.97 |
| 34 | 2.89 |
| 35 | 0.61 |
| 36 | 0.49 |
| 37 | 0.93 |
| 38 | 1.50 |
| 39 | 0.57 |
| 40 | 0.51 |
| 41 | 0.84 |
| 42 | 0.65 |
| 43 | 0.39 |
| 44 | 0.70 |
| 45 | 0.65 |
| 46 | 0.39 |
| 47 | 0.52 |
| 48 | 0.68 |
| 49 | 0.49 |
| 50 | 0.67 |
| 51 | 0.91 |
| 52 | 1.05 |
| 53 | 0.38 |
| 54 | 0.31 |
| 55 | 0.82 |
| 56 | 1.11 |
| 57 | 2.97 |
| 58 | 0.91 |
| 59 | 0.16 |
| 60 | 0.92 |
| 61 | 1.42 |
| 62 | 0.71 |
| 63 | 0.89 |
| 64 | 0.32 |
| 65 | 0.56 |
| 66 | 1.25 |
| 67 | 2.12 |
| 69 | 0.85 |
| 70 | 0.20 |
| 71 | 1.01 |
| 72 | 1.48 |
| 73 | 1.04 |
| 74 | 1.01 |
| 75 | 0.86 |
| 76 | 1.88 |
| 77 | 0.85 |
| 78 | 1.83 |
| 79 | 1.70 |
| 80 | 4.65 |
| 81 | 1.92 |
| 82 | 2.36 |
| 83 | 1.21 |
| 84 | 2.77 |
| 85 | 1.12 |
| 86 | 1.54 |
| 87 | 2.01 |
| 88 | 1.35 |
| 89 | 0.90 |
| 90 | 0.92 |
| 91 | 1.28 |
| 92 | 1.74 |
| 93 | 1.92 |
| 94 | 0.98 |
| 95 | 0.85 |
| 96 | 1.40 |
| 97 | 2.08 |
| 98 | 1.69 |
| 99 | 1.23 |
| 100 | 0.72 |

Tubulin Acetylation Induction by Novel Compounds: Tubulin Acetylation Cytoblot Assay.

Tubulin acetylation is a PD marker for HDAC6 inhibition. The extent of tubulin acetylation represents the inhibitory effect on HDAC6. Examples in Table 2 of this invention demonstrated tubulin acetylation activities with EC$_{50}$ values in the range of 0.1 μM to 10 μM as shown in Table 2.

Novel compounds were tested for their ability to inhibit HDAC6 using a cell-based deacetylation assay. Tubulin acetylation was detected by the anti-acetylated tubulin antibody (Sigma) and horse radish peroxidase (HRP) conjugated secondary antibody (KangChen Bio. Tech.). A549 cells were seeded into assay plates (CORNING 3912) at concentration of $1\times10^5$ cells/mL and incubated for 16-18 h at 37° C. with the presence of 5% CO$_2$. 20 μl of diluted compound solution was transferred to the cell culture plate and incubated for 17-18 h. After medium removal and fixation by formaldehyde (3.7% paraformaldehyde in TBS), the cells in the plates were treated with 180 μl of −20° C. MeOH and incubated for 5 min at rt. The cell lysis was incubated with 75 μl of primary anti-acetylated tubulin antibody and secondary HRP conjugated antibody solution (1:750 anti-acetylated tubulin, 1:750 HRP conjugated anti-mouse IgG in antibody dilution buffer not containing sodium azide) for 4 h at 4° C. By adding the HRP substrate, enhanced chemiluminescence (ECL) reagent (GE Healthcare) generated luminescence corresponding to the level of tubulin acetylation. So that 75 μl of ECL was added into the wells and the luminescence from each well was immediately quantified by the plate reader. Based on the luminescence reading, the Tub-Ac EC$_{50}$s against HDAC6 of the tested compounds were calculated by plotting the curve with XLfit4.0 software. Inhibition %=[signal(sample)−Mean(bottom)]×100/[Mean(top)−Mean(bottom)]

TABLE 2

Tubulin acetylation induction by novel compounds:
tubulin acetylation cytoblot assay.

| Example # | Tub-Ac EC$_{50}$ (μM) |
|---|---|
| 1 | 5.86 |
| 2 | 4.02 |
| 3 | 1.56 |
| 4 | 3.89 |
| 5 | 6.67 |
| 6 | 2.82 |
| 7 | 1.41 |
| 8 | 4.12 |
| 9 | 1.73 |
| 10 | 2.15 |
| 11 | 8.31 |
| 13 | 1.53 |
| 14 | 2.61 |
| 15 | 4.90 |
| 16 | 1.06 |
| 17 | 11.87 |
| 18 | 4.31 |
| 19 | 3.14 |

TABLE 2-continued

Tubulin acetylation induction by novel compounds:
tubulin acetylation cytoblot assay.

| Example # | Tub-Ac EC$_{50}$ (μM) |
|---|---|
| 20 | 0.96 |
| 21 | 4.69 |
| 22 | 1.32 |
| 24 | 2.48 |
| 25 | 4.33 |
| 26 | 4.94 |
| 27 | 2.38 |
| 28 | 4.11 |
| 29 | 13.82 |
| 30 | 2.28 |
| 31 | 9.78 |
| 32 | 0.70 |
| 33 | 0.68 |
| 34 | 10.60 |
| 35 | 2.04 |
| 36 | 2.05 |
| 37 | 2.16 |
| 38 | 1.06 |
| 39 | 13.07 |
| 40 | 1.31 |
| 41 | 5.15 |
| 42 | 11.36 |
| 44 | 6.31 |
| 45 | 8.30 |
| 47 | 3.02 |
| 48 | 4.60 |
| 49 | 9.86 |
| 50 | 8.62 |
| 51 | 8.99 |
| 52 | 2.82 |
| 53 | 3.32 |
| 55 | 4.75 |
| 56 | 2.82 |
| 57 | 2.64 |
| 58 | 1.00 |
| 59 | 0.30 |
| 60 | 0.53 |
| 61 | 8.25 |
| 62 | 1.93 |
| 63 | 0.36 |
| 64 | 10.23 |
| 66 | 2.42 |
| 67 | 6.23 |
| 68 | 6.67 |
| 69 | 8.23 |
| 70 | 1.71 |
| 71 | 0.81 |
| 72 | 2.34 |
| 73 | 1.47 |
| 74 | 1.84 |
| 75 | 4.56 |
| 76 | 3.02 |
| 77 | 1.25 |
| 78 | 1.81 |
| 79 | 4.54 |
| 80 | 4.26 |
| 81 | 0.72 |
| 82 | 1.43 |
| 83 | 1.11 |
| 85 | 7.31 |
| 91 | 5.23 |
| 92 | 0.33 |
| 93 | 0.41 |
| 94 | 0.15 |
| 95 | 0.08 |
| 96 | 0.32 |
| 97 | 0.20 |
| 98 | 0.19 |
| 99 | 0.15 |
| 100 | 0.71 | p21 Reporter Gene Induction by Novel Compounds

As a surrogate for in-cell HDAC1/2/3 inhibition, p21 induction was used as a counterscreen to evaluate the selectivity of the compounds in the present invention toward HDAC6 or HDAC8. In contrast to positive controls MS275 and SAHA, none of the compounds of the present invention showed comparable p21 induction activity at 3 μM, 10 μM, and 30 μM concentrations.

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37° C. in 5% CO$_2$ overnight. A transfection media was prepared prior to transfection according to the following procedure: (1) 5 μl serum-free DMEM, 0.15 μl Fugene 6 reagent, 40 ng p21-luc, 10 ng GFP were mixed gently and incubated at rt for 30 minutes; (2), then 98 μl DMEM (with 10% FBS, 1% penicillin and streptomycin) was added to the DNA: Fugene 6 reagent complex and mixed gently. For transfection, the medium was removed and replaced with 100 μl/well transfection media which was prepared according to the procedure above. After incubating the cells for 24 hours at 37° C. in 5% CO$_2$, fresh media and test compounds were added to the wells and the cells further incubated for 15 hours at 37° C. in 5% CO$_2$. Cells were lysed by adding 80 μl/well of a cell culture lysis reagent (Promega). 50 μl of each lysate was taken for GFP detection using an excitation wavelength of 486 nm and detection at 527 nm. 100 μl luciferase assay reagent (Promega) was then added to every 20 μl cell lysate for luminometer detection. The compounds of this invention described in the Examples and Tables above exhibit weak p21 induction activity in the range of about 0% to 50% relative to the known HDAC inhibitor (MS-275) at 1 μM 3 μM and 10 μM concentrations. Induction activity for specific representative compounds can be found in Table 3.

TABLE 3 p21 reporter gene induction by novel compounds in relative potency to MS-275

| Example # | p21 RP3 * | p21 RP10 * | p21 RP30 * |
|---|---|---|---|
| 1 | 0.08 | 0.08 | 0.15 |
| 2 | 0.33 | 0.26 | 0.46 |
| 3 | 0.18 | 0.06 | 0.08 |
| 4 | 0.43 | 0.31 | 0.48 |
| 5 | −0.01 | 0.06 | 0.08 |
| 6 | 0.03 | 0.15 | 0.15 |
| 7 | −0.08 | 0.12 | 0.16 |
| 8 | 0.09 | 0.15 | 0.29 |
| 9 | 0.24 | 0.13 | 0.23 |
| 10 | 0.07 | 0.05 | 0.05 |
| 11 | 0.39 | 0.08 | 0.04 |
| 12 | 0.01 | 0.10 | 0.14 |
| 13 | 0.29 | 0.19 | 0.09 |
| 14 | 0.13 | 0.07 | 0.06 |
| 15 | 0.09 | 0.06 | 0.04 |
| 16 | 0.17 | 0.12 | −0.03 |
| 17 | 0.00 | 0.02 | 0.02 |
| 18 | 0.61 | 0.02 | −0.01 |
| 19 | 0.46 | 0.00 | −0.03 |
| 20 | 0.37 | 0.10 | 0.12 |
| 21 | 1.56 | 0.48 | 0.28 |
| 22 | 0.42 | 0.28 | 0.39 |
| 23 | 0.10 | 0.04 | 0.03 |
| 24 | 0.11 | 0.02 | 0.02 |
| 25 | 0.00 | 0.14 | −0.03 |
| 26 | 0.42 | 0.06 | 0.04 |
| 27 | 0.11 | 0.03 | 0.04 |
| 28 | 0.04 | 0.01 | 0.01 |
| 29 | 0.55 | 0.10 | 0.12 |
| 30 | 0.13 | 0.09 | 0.05 |

TABLE 3-continued p21 reporter gene induction by novel compounds in relative potency to MS-275

| Example # | p21 RP3 * | p21 RP10 * | p21 RP30 * |
|---|---|---|---|
| 31 | 0.09 | 0.07 | 0.05 |
| 32 | 0.38 | 0.08 | 0.15 |
| 33 | 0.45 | 0.41 | 0.18 |
| 34 | 0.36 | 0.12 | 0.06 |
| 35 | 0.44 | 0.25 | 0.20 |
| 36 | 0.55 | 0.18 | 0.45 |
| 37 | 0.04 | 0.04 | 0.06 |
| 38 | 0.50 | 0.02 | −0.02 |
| 39 | 0.29 | 0.09 | 0.20 |
| 40 | 0.25 | 0.26 | 0.21 |
| 41 | 0.05 | 0.02 | 0.02 |
| 42 | 0.02 | 0.09 | 0.34 |
| 43 | −0.02 | 0.22 | 0.62 |
| 44 | −0.10 | 0.03 | 0.10 |
| 45 | −0.19 | 0.02 | 0.13 |
| 46 | 0.07 | 0.26 | 0.70 |
| 47 | 0.05 | 0.09 | 0.29 |
| 48 | 0.24 | 0.08 | 0.23 |
| 49 | 0.41 | 0.50 | 0.85 |
| 50 | 0.17 | 0.17 | 0.53 |
| 51 | −0.14 | 0.60 | 0.38 |
| 52 | 0.14 | 0.53 | 0.58 |
| 53 | 2.37 | 1.21 | 0.13 |
| 54 | 0.28 | 0.46 | 0.79 |
| 55 | 0.43 | 0.20 | 0.50 |
| 56 | 0.37 | 0.07 | 0.14 |
| 57 | 0.05 | 0.03 | 0.01 |
| 58 | 0.50 | 0.13 | 0.07 |
| 59 | 0.23 | 0.22 | 0.24 |
| 60 | 0.80 | 0.16 | 0.07 |
| 61 | 0.46 | 0.09 | 0.17 |
| 62 | 0.55 | 0.11 | 0.20 |
| 63 | 0.47 | 0.15 | 0.22 |
| 64 | 0.30 | 0.04 | 0.02 |
| 65 | 0.00 | 0.00 | 0.00 |
| 66 | 0.01 | 0.01 | 0.00 |
| 67 | 0.40 | 0.17 | 0.02 |
| 68 | −0.05 | 0.02 | 0.01 |
| 69 | 0.36 | 0.15 | −0.03 |
| 70 | −0.07 | 0.00 | 0.02 |
| 71 | 0.13 | 0.06 | 0.04 |
| 72 | 0.16 | 0.14 | 0.09 |
| 73 | 0.12 | 0.04 | 0.04 |
| 74 | −0.07 | 0.07 | 0.12 |
| 75 | 0.19 | 0.07 | 0.11 |
| 77 | 0.00 | 0.07 | 0.07 |
| 78 | 0.64 | 0.15 | 0.04 |
| 79 | 0.21 | 0.09 | 0.04 |
| 80 | 0.37 | 0.08 | −0.05 |
| 81 | 0.08 | −0.04 | −0.01 |
| 82 | 0.14 | −0.08 | −0.06 |
| 83 | 0.37 | 0.11 | 0.08 |
| 84 | 0.13 | 0.02 | 0.01 |
| 85 | 0.35 | 0.10 | 0.05 |
| 86 | 0.04 | 0.01 | 0.01 |
| 87 | 0.20 | 0.00 | −0.03 |
| 88 | 0.35 | 0.06 | 0.03 |
| 89 | 0.38 | 0.10 | 0.06 |
| 90 | 0.38 | 0.09 | 0.05 |
| 91 | 2.06 | 2.66 | 0.84 |
| 92 | 0.56 | 0.20 | 0.40 |
| 93 | 0.58 | 0.12 | 0.05 |
| 95 | 0.58 | 0.39 | 0.60 |
| 96 | 0.86 | 1.34 | 0.02 |
| 97 | 2.39 | 3.56 | 0.07 |
| 98 | 2.13 | 3.06 | 0.00 |
| 99 | 0.95 | 0.62 | 0.00 |
| 100 | 0.45 | 0.13 | 0.31 |

Note:
p21 RP3 represents the relative gene level of p21 induced by individual example compared to MS275 at 3 μM concentrations; p21 RP10 represents the relative level of p21 induced by individual example compared to MS275 at 10 μM concentrations; p21 RP30 represents the relative level of p21 induced by individual example compared to MS275 at 30 μM concentrations.

WST Anti-Proliferative Assay and Assessment of Growth Inhibitory of Novel Compounds in Multiple Myeloma Cell Lines.

| Example # | $IC_{50}$ (RPMI8226, μM) | $IC_{50}$ (OPM-2, μM) |
|---|---|---|
| 7 | 8.79 | 5.56 |
| 47 | 4.05 | 3.62 |
| 60 | 8.11 | 3.94 |
| 70 | 10.7 | 6.47 |
| 71 | 5.62 | 3.46 |
| 73 | 6.49 | 4.95 |

The novel compounds of the present invention were tested for their ability to inhibit growth of multiple myeloma cell lines (RPMI-8226 or OPM-2) using in vitro growth inhibition assays described below.

Cells were seeded in 96-well culture plates (200 μl/well at different seeding concentrations depending on cell type) and incubated overnight at 37° C. in 5% $CO_2$. After adding compound dilutions to the cells (DMSO concentration kept below 0.5%), the cells were incubated at 37° C. in 5% $CO_2$ for 72 hours. The effects on proliferation were determined by addition of CCK-8 reagent (Dojindo) according to the manufacturer's instruction, followed by incubation for 2 hours at 37° C. in 5% $CO_2$, and finally recording the absorbance at 450 nm using an ELISA plate reader.

It has been found that the compounds of the present invention are HDAC6 or HDAC8 inhibitors which have anti-proliferative and differentiation-inducing activity, which results in inhibition of tumor cell proliferation and induction of apoptosis. These compounds are therefore useful for the treatment of diseases such as neuroblastoma and multiple myeloma in humans or animals.

Compounds as described above have activities in one of the foregoing tests between 0.01 μM and 20 μM. Preferred compounds have activities in one of the foregoing tests between 0.01 μM and 10 μM. Particularly preferred compounds have activities in one of the foregoing tests between 0.01 μM and 1 μM.

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| Total | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| Total | 220.0 mg |

What is claimed is:

1. A compound of formula (I)

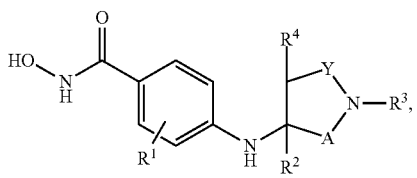

wherein $R^1$ is hydrogen, alkyl or halogen;

$R^2$ is hydrogen, alkyl, hydroxyalkyl, alkoxyalkyl, aminoalkyl, alkylaminoalkyl or dialkylaminoalkyl;

$R^3$ is phenyl, unsubstituted or substituted once, or twice or three times by halogen, alkyl, alkoxy, alkylsulfonyl, cyano, trifluoromethyl, phenyl, phenoxy, pyrrolyl, imidazonyl, oxazolyl or dialkylaminoalkoxy;

naphthalenyl, unsubstituted or once or twice substituted by halogen, alkyl, alkoxy, alkylsulfonyl, cyano, trifluoromethyl, dialkylamino or dialkylaminoalkyl;

quinolinyl, unsubstituted or once or twice substituted by alkyl, alkoxy, alkylsulfonyl, cyano, trifluoromethyl, dialkylamino or dialkylaminoalkyl;

cycloalkyl;

phenylalkyl, wherein phenyl can be unsubstituted or once or twice substituted by halogen, alkoxy, phenyl, alkyl, cyano, alkylsulfonyl, trifluoromethyl, phenoxy, pyrrolyl, imidazonyl, oxazolyl or dialkylaminoalkoxy;

naphthalenylalkyl, wherein naphthalenyl can be unsubstituted or once or twice substituted by halogen, alkoxy, phenyl, alkyl, cyano, alkylsulfonyl, trifluoromethyl, phenoxy, pyrrolyl, imidazonyl, oxazolyl or dialkylaminoalkoxy;

phenylcycloalkyl, wherein phenyl can be unsubstituted or once or twice substituted by halogen, alkoxy, phenyl, alkyl, cyano, alkylsulfonyl, trifluoromethyl, phenoxy, pyrrolyl, imidazonyl, oxazolyl or dialkylaminoalkoxy;

pyrimidinyl, wherein pyrimidinyl can be unsubstituted or once or twice substituted by alkoxy, phenyl, alkyl, cyano, alkylsulfonyl, trifluoromethyl, phenoxy, pyrrolyl, imidazonyl, oxazolyl or dialkylaminoalkoxy;

phenylsulfonyl, wherein phenyl can be unsubstituted or once or twice substituted by halogen, phenyl, alkoxy, alkyl, cyano, alkylsulfonyl, trifluoromethyl, phenoxy, pyrrolyl, imidazonyl, oxazolyl or dialkylaminoalkoxy; or phenylcarbonyl, wherein phenyl can be unsubstituted or once or twice substituted by halogen, alkoxy, phenyl, alkyl, cyano, alkylsulfonyl, trifluoromethyl, phenoxy, pyrrolyl, imidazonyl, oxazolyl or dialkylaminoalkoxy;

$R^4$ is hydrogen or alkyl;

Y is —$CH_2$— or —C=O;

or $R^4$ and Y, together with the carbon atom to which $R^4$ is attached, may form a phenyl ring or pyridinyl ring, which may be unsubstituted or further substituted by halogen; provided that $R^2$ is alkyl;

A is —C=O, —$CH_2$— or —CH-alkyl, provided that A and Y are not —C=O at the same time;

or a pharmaceutically acceptable salt, ester or stereoisomers thereof.

2. The compound of claim 1, wherein $R^1$ is hydrogen or halogen;

$R^2$ is hydrogen or alkyl;

$R^3$ is phenyl, unsubstituted or substituted once, or twice or three times by halogen, alkyl, alkoxy, alkylsulfonyl, cyano, trifluoromethyl, phenyl, phenoxy, pyrrolyl, imidazonyl, oxazolyl or dialkylaminoalkoxy;

naphthalenyl;

quinolinyl;

cycloalkyl;

phenylalkyl, wherein phenyl can be unsubstituted or once or twice substituted by halogen, alkoxy or phenyl;

naphthalenylalkyl;

phenylcycloalkyl;

pyrimidinyl;

phenylsulfonyl, wherein phenyl can be unsubstituted or once or twice substituted by halogen or phenyl; or phenylcarbonyl, wherein phenyl can be unsubstituted or once or twice substituted by halogen or alkoxy;

$R^4$ is hydrogen or alkyl;

and all remaining substituents have the significances given in claim 1.

3. The compound of claim 2, wherein $R^1$ is hydrogen, fluoro or chloro.

4. The compound of claim 3, wherein $R^2$ is hydrogen, methyl or ethyl.

5. The compound of claim 4, wherein $R^2$ is hydrogen or methyl.

6. The compound of claim 5, wherein $R^3$ is phenyl, which phenyl is unsubstituted or substituted once, or twice or three times by fluoro, chloro, methoxy, methyl, isopropyl, isopropoxy, butyl, tert-butyl, methylsulfonyl, cyano, trifluoromethyl, phenoxy, phenyl, pyrrolyl, imidazonyl, oxazolyl or dimethylaminoethoxy; or is naphthalenyl; quinolinyl; cyclohexyl; phenylmethyl; phenylethyl; phenylisopropyl; chlorophenylmethyl; methoxyphenylmethyl; chlorophenylisopropyl; phenylphenylisopropyl; naphthalenylisopropyl; phenylcyclobutyl; phenylcyclopentanyl; phenylcyclohexyl; pyrimidinyl; phenylsulfonyl; fluorophenylsulfonyl; chlorophenylsulfonyl; phenylphenylsulfonyl; phenylcarbonyl; fluorophenylcarbonyl or methoxyphenylcarbonyl.

7. The compound of claim 6, wherein $R^3$ is phenyl, unsubstituted or once substituted by dimethylaminoethoxy, once or twice substituted by fluoro, chloro or cyano; or is quinolinyl; phenylmethyl; phenylethyl; phenylisopropyl; chlorophenylisopropyl; phenylcyclobutyl; phenylcyclohexyl; pyrimidinyl; fluorophenylsulfonyl; fluorophenylcarbonyl or chlorophenylmethyl.

8. The compound of claim 7, wherein $R^4$ is hydrogen or methyl.

9. The compound of claim 8, wherein Y is —CH$_2$— or —C═O; or

R$^4$ and Y, together with the carbon atom to which R$^4$ is attached, form a phenyl ring or pyridinyl ring, which may be unsubstituted or substituted by fluoro provided that R$^2$ is alkyl.

10. The compound of claim 9, wherein A is —C═O, —CH$_2$— or —CH—CH$_3$; provided that A and Y are not —C═O at the same time.

11. A compound of claim 1 selected from the group consisting of

N-Hydroxy-4-(5-oxo-1-phenyl-pyrrolidin-3-ylamino)-benzamide;
4-[1-(2-Fluoro-phenyl)-2-oxo-pyrrolidin-3-ylamino]-N-hydroxy-benzamide;
4-[1-(3-Fluoro-phenyl)-2-oxo-pyrrolidin-3-ylamino]-N-hydroxy-benzamide;
4-[1-(4-Fluoro-phenyl)-2-oxo-pyrrolidin-3-ylamino]-N-hydroxy-benzamide;
4-[1-(2-Chloro-phenyl)-2-oxo-pyrrolidin-3-ylamino]-N-hydroxy-benzamide;
4-[1-(3-Chloro-phenyl)-2-oxo-pyrrolidin-3-ylamino]-N-hydroxy-benzamide;
4-[1-(4-Chloro-phenyl)-2-oxo-pyrrolidin-3-ylamino]-N-hydroxy-benzamide;
N-Hydroxy-4-[1-(3-methoxy-phenyl)-2-oxo-pyrrolidin-3-ylamino]-benzamide;
N-Hydroxy-4-[1-(3-isopropoxy-phenyl)-2-oxo-pyrrolidin-3-ylamino]-benzamide;
N-Hydroxy-4-[1-(4-isopropoxy-phenyl)-2-oxo-pyrrolidin-3-ylamino]-benzamide;
N-Hydroxy-4-[2-oxo-1-(3-trifluoromethyl-phenyl)-pyrrolidin-3-ylamino]-benzamide and
N-Hydroxy-4-[2-oxo-1-(4-trifluoromethyl-phenyl)-pyrrolidin-3-ylamino]-benzamide.

12. A compound of claim 1 selected from the group consisting of

N-Hydroxy-4-[1-(3-isopropyl-phenyl)-2-oxo-pyrrolidin-3-ylamino]-benzamide;
N-Hydroxy-4-[1-(4-isopropyl-phenyl)-2-oxo-pyrrolidin-3-ylamino]-benzamide;
4-[1-(4-Butyl-phenyl)-2-oxo-pyrrolidin-3-ylamino]-N-hydroxy-benzamide;
4-[1-(4-tert-Butyl-phenyl)-2-oxo-pyrrolidin-3-ylamino]-N-hydroxy-benzamide;
N-Hydroxy-4-[1-(4-methanesulfonyl-phenyl)-2-oxo-pyrrolidin-3-ylamino]-benzamide;
4-[1-(3-Cyano-phenyl)-2-oxo-pyrrolidin-3-ylamino]-N-hydroxy-benzamide;
4-[1-(4-Cyano-phenyl)-2-oxo-pyrrolidin-3-ylamino]-N-hydroxy-benzamide;
4-[1-(3-Chloro-4-fluoro-phenyl)-2-oxo-pyrrolidin-3-ylamino]-N-hydroxy-benzamide;
4-[1-(3-Chloro-5-fluoro-phenyl)-2-oxo-pyrrolidin-3-ylamino]-N-hydroxy-benzamide;
4-[1-(5-Chloro-2-fluoro-phenyl)-2-oxo-pyrrolidin-3-ylamino]-N-hydroxy-benzamide;
4-[1-(2,4-Dichloro-phenyl)-2-oxo-pyrrolidin-3-ylamino]-N-hydroxy-benzamide and
4-[1-(2,3-Dichloro-phenyl)-2-oxo-pyrrolidin-3-ylamino]-N-hydroxy-benzamide.

13. A compound of claim 1 selected from the group consisting of

4-[1-(3,4-Dichloro-phenyl)-2-oxo-pyrrolidin-3-ylamino]-N-hydroxy-benzamide;
4-[1-(3,5-Dichloro-phenyl)-2-oxo-pyrrolidin-3-ylamino]-N-hydroxy-benzamide;
4-[1-(2,6-Dichloro-phenyl)-2-oxo-pyrrolidin-3-ylamino]-N-hydroxy-benzamide;
4-[1-(4-Fluoro-2,6-dimethyl-phenyl)-2-oxo-pyrrolidin-3-ylamino]-N-hydroxy-benzamide;
4-[1-(4-Chloro-3-hydroxymethyl-phenyl)-2-oxo-pyrrolidin-3-ylamino]-N-hydroxy-benzamide;
N-Hydroxy-4-[2-oxo-1-(3-phenoxy-phenyl)-pyrrolidin-3-ylamino]-benzamide;
N-Hydroxy-4-[2-oxo-1-(4-phenoxy-phenyl)-pyrrolidin-3-ylamino]-benzamide;
4-(1-Biphenyl-3-yl-2-oxo-pyrrolidin-3-ylamino)-N-hydroxy-benzamide;
N-Hydroxy-4-[2-oxo-1-(3-pyrrol-1-yl-phenyl)-pyrrolidin-3-ylamino]-benzamide;
N-Hydroxy-4-[1-(4-imidazol-1-yl-phenyl)-2-oxo-pyrrolidin-3-ylamino]-benzamide;
N-Hydroxy-4-[1-(3-oxazol-5-yl-phenyl)-2-oxo-pyrrolidin-3-ylamino]-benzamide and
4-{1-[3-(2-Dimethylamino-ethoxy)-phenyl]-2-oxo-pyrrolidin-3-ylamino}-N-hydroxy-benzamide.

14. A compound of claim 1 selected from the group consisting of

N-Hydroxy-4-(1-naphthalen-1-yl-2-oxo-pyrrolidin-3-ylamino)-benzamide;
N-Hydroxy-4-(1-naphthalen-2-yl-2-oxo-pyrrolidin-3-ylamino)-benzamide;
N-Hydroxy-4-(2-oxo-1-quinolin-8-yl-pyrrolidin-3-ylamino)-benzamide;
N-Hydroxy-4-(2-oxo-1-quinolin-5-yl-pyrrolidin-3-ylamino)-benzamide;
4-(1-Cyclohexyl-2-oxo-pyrrolidin-3-ylamino)-N-hydroxy-benzamide;
4-(1-Benzyl-5-oxo-pyrrolidin-3-ylamino)-N-hydroxy-benzamide;
N-Hydroxy-4-(2-oxo-1-phenethyl-pyrrolidin-3-ylamino)-benzamide;
N-Hydroxy-4-[5-oxo-1-(R-1-phenyl-ethyl)-pyrrolidin-3-ylamino]-benzamide;
N-Hydroxy-4-[1-(4-methoxy-benzyl)-2-oxo-pyrrolidin-3-ylamino]-benzamide;
N-Hydroxy-4-[1-(1-methyl-1-phenyl-ethyl)-2-oxo-pyrrolidin-3-ylamino]-benzamide and
4-{1-[1-(2-Chloro-phenyl)-1-methyl-ethyl]-2-oxo-pyrrolidin-3-ylamino}-N-hydroxy-benzamide.

15. A compound of claim 1 selected from the group consisting of

4-{1-[1-(3-Chloro-phenyl)-1-methyl-ethyl]-2-oxo-pyrrolidin-3-ylamino}-N-hydroxy-benzamide;
4-{1-[1-(4-Chloro-phenyl)-1-methyl-ethyl]-2-oxo-pyrrolidin-3-ylamino}-N-hydroxy-benzamide;
4-[1-(1-Biphenyl-4-yl-1-methyl-ethyl)-2-oxo-pyrrolidin-3-ylamino]-N-hydroxy-benzamide;
N-Hydroxy-4-[1-(1-methyl-1-naphthalen-1-yl-ethyl)-2-oxo-pyrrolidin-3-ylamino]-benzamide;
N-Hydroxy-4-[1-(1-methyl-1-naphthalen-2-yl-ethyl)-2-oxo-pyrrolidin-3-ylamino]-benzamide;
N-Hydroxy-4-[2-oxo-1-(1-phenyl-cyclobutyl)-pyrrolidin-3-ylamino]-benzamide;
N-Hydroxy-4-[2-oxo-1-(1-phenyl-cyclopentyl)-pyrrolidin-3-ylamino]-benzamide;
N-Hydroxy-4-[2-oxo-1-(1-phenyl-cyclohexyl)-pyrrolidin-3-ylamino]-benzamide;
N-Hydroxy-4-(3-methyl-2-oxo-1-phenyl-pyrrolidin-3-ylamino)-benzamide;
4-[1-(3-Fluoro-phenyl)-3-methyl-2-oxo-pyrrolidin-3-ylamino]-N-hydroxy-benzamide;

4-[1-(3-Chloro-phenyl)-3-methyl-2-oxo-pyrrolidin-3-ylamino]-N-hydroxy-benzamide and
4-[1-(4-Chloro-phenyl)-3-methyl-2-oxo-pyrrolidin-3-ylamino]-N-hydroxy-benzamide.

16. A compound of claim 1 selected from the group consisting of
N-Hydroxy-4-(3-methyl-2-oxo-1-quinolin-3-yl-pyrrolidin-3-ylamino)-benzamide;
N-Hydroxy-4-(3-methyl-2-oxo-1-quinolin-8-yl-pyrrolidin-3-ylamino)-benzamide;
N-Hydroxy-4-(3-methyl-2-oxo-1-quinolin-6-yl-pyrrolidin-3-ylamino)-benzamide;
N-Hydroxy-4-[3-methyl-1-(1-methyl-1-phenyl-ethyl)-2-oxo-pyrrolidin-3-ylamino]-benzamide;
4-[3-Ethyl-1-(1-methyl-1-phenyl-ethyl)-2-oxo-pyrrolidin-3-ylamino]-N-hydroxy-benzamide;
2-Fluoro-N-hydroxy-4-(2-oxo-1-phenyl-pyrrolidin-3-ylamino)-benzamide;
4-[1-(3-Chloro-phenyl)-2-oxo-pyrrolidin-3-ylamino]-2-fluoro-N-hydroxy-benzamide;
4-[1-(3,4-Dichloro-phenyl)-2-oxo-pyrrolidin-3-ylamino]-2-fluoro-N-hydroxy-benzamide;
3-Chloro-N-hydroxy-4-(2-oxo-1-phenyl-pyrrolidin-3-ylamino)-benzamide;
4-[1-(4-Fluoro-phenyl)-5-oxo-pyrrolidin-3-ylamino]-N-hydroxy-benzamide;
4-[1-(2-Chloro-phenyl)-5-oxo-pyrrolidin-3-ylamino]-N-hydroxy-benzamide and
4-[1-(3-Chloro-phenyl)-5-oxo-pyrrolidin-3-ylamino]-N-hydroxy-benzamide.

17. A compound of claim 1 selected from the group consisting of
4-[1-(4-Chloro-phenyl)-5-oxo-pyrrolidin-3-ylamino]-N-hydroxy-benzamide;
N-Hydroxy-4-[1-(3-methoxy-phenyl)-5-oxo-pyrrolidin-3-ylamino]-benzamide;
4-(1-Benzyl-5-oxo-pyrrolidin-3-ylamino)-N-hydroxy-benzamide;
N-Hydroxy-4-[1-(1-methyl-1-phenyl-ethyl)-5-oxo-pyrrolidin-3-ylamino]-benzamide;
Trans-4-[1-(4-Chloro-phenyl)-2-methyl-5-oxo-pyrrolidin-3-ylamino]-N-hydroxy-benzamide;
4-[1-(4-Chloro-phenyl)-4-methyl-5-oxo-pyrrolidin-3-ylamino]-N-hydroxy-benzamide;
N-Hydroxy-4-(1-phenyl-pyrrolidin-3-ylamino)-benzamide;
4-[1-(4-Chloro-phenyl)-pyrrolidin-3-ylamino]-N-hydroxy-benzamide;
4-[1-(2,6-Dichloro-phenyl)-pyrrolidin-3-ylamino]-N-hydroxy-benzamide;
4-[1-(2,4-Dichloro-phenyl)-pyrrolidin-3-ylamino]-N-hydroxy-benzamide;
N-Hydroxy-4-(1-pyrimidin-2-yl-pyrrolidin-3-ylamino)-benzamide and
4-(1-Benzenesulfonyl-pyrrolidin-3-ylamino)-N-hydroxy-benzamide.

18. A compound of claim 1 selected from the group consisting of
4-[1-(4-Fluoro-benzenesulfonyl)-pyrrolidin-3-ylamino]-N-hydroxy-benzamide;
4-[1-(4-Chloro-benzenesulfonyl)-pyrrolidin-3-ylamino]-N-hydroxy-benzamide;
4-[1-(Biphenyl-4-sulfonyl)-pyrrolidin-3-ylamino]-N-hydroxy-benzamide;
4-(1-Benzoyl-pyrrolidin-3-ylamino)-N-hydroxy-benzamide;
4-[1-(4-Fluoro-benzoyl)-pyrrolidin-3-ylamino]-N-hydroxy-benzamide;
N-Hydroxy-4-[1-(4-methoxy-benzoyl)-pyrrolidin-3-ylamino]-benzamide;
4-(1-Benzyl-3-methyl-2-oxo-2,3-dihydro-1H-indol-3-ylamino)-N-hydroxy-benzamide;
4-[1-2-chloro-benzyl)-3-methyl-2-oxo-2,3-dihydro-1H-indol-3-ylamino)-N-hydroxy-benzamide;
4-[1-(3-chloro-benzyl)-3-methyl-2-oxo-2,3-dihydro-1H-indol-3-ylamino)-N-hydroxy-benzamide;
N-hydroxy-4-(3-methyl-2-oxo-1-phenethyl-2,3-dihydro-1H-indol-3-ylamino)-benzamide and
N-hydroxy-4-(3-methyl-2-oxo-1-phenyl-2,3-dihydro-1H-indol-3-ylamino)-benzamide.

19. A compound of claim 1 selected from the group consisting of
4-[1-(3-chloro-phenyl)-3-methyl-2-oxo-2,3-dihydro-1H-indol-3-ylamino)-N-hydroxy-benzamide;
4-[1-(4-Chloro-phenyl)-5-fluoro-3-methyl-2-oxo-2,3-dihydro-1H-indol-3-ylamino]-N-hydroxy-benzamide;
4-[1-(3-Chloro-phenyl)-5-fluoro-3-methyl-2-oxo-2,3-dihydro-1H-indol-3-ylamino]-N-hydroxy-benzamide;
4-[1-(2-Chloro-benzyl)-5-fluoro-3-methyl-2-oxo-2,3-dihydro-1H-indol-3-ylamino]-N-hydroxy-benzamide; and
4-[1-(3-Chloro-phenyl)-3-methyl-2-oxo-2,3-dihydro-1H-pyrrolo[3,2-c]pyridin-3-ylamino]-N-hydroxy-benzamide.

20. A process for preparing a compound of formula (I) which process comprises hydrolysis a compound of formula (A)

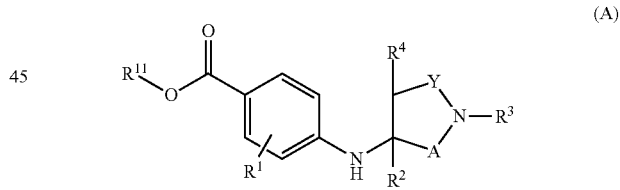

(A)

with hydroxyamine in the presence of a base;
wherein $R^1$, $R^2$, $R^3$, $R^4$, A and Y have the significances given in claim 1, and $R^{11}$ is alkyl.

21. A pharmaceutical composition comprising a compound of claim 1 together with therapeutically inert carriers or excipients.

* * * * *